(12) United States Patent
Duportet et al.

(10) Patent No.: US 11,617,773 B2
(45) Date of Patent: Apr. 4, 2023

(54) ELIMINATION OF COLONIC BACTERIAL DRIVING LETHAL INFLAMMATORY CARDIOMYOPATHY

(71) Applicants: Eligo Bioscience, Paris (FR); Kantonsspital St.Gallen, St.Gallen (CH)

(72) Inventors: Xavier Duportet, Paris (FR); Cristina del Carmen Gil-Cruz, St. Gallen (CH); Christian Ivan Pérez-Shibayama, St. Gallen (CH); Burkhard Ludewig, St. Gallen (CH)

(73) Assignees: Eligo Bioscience, Paris (FR); Kantonsspital St.Gallen, St.Gallen (CH)

( * ) Notice: Subject to any disclaimer, the term of this patent is extended or adjusted under 35 U.S.C. 154(b) by 0 days.

(21) Appl. No.: 17/225,854

(22) Filed: Apr. 8, 2021

(65) Prior Publication Data
US 2021/0315950 A1 Oct. 14, 2021

Related U.S. Application Data

(60) Provisional application No. 63/007,197, filed on Apr. 8, 2020.

(51) Int. Cl.
| | | |
|---|---|---|
| *A61K 48/00* | (2006.01) | |
| *A01N 63/00* | (2020.01) | |
| *C07H 21/04* | (2006.01) | |
| *A61K 35/76* | (2015.01) | |
| *C12N 9/22* | (2006.01) | |
| *A61K 31/7036* | (2006.01) | |
| *A61K 31/505* | (2006.01) | |
| *A61K 38/14* | (2006.01) | |
| *A61K 31/4164* | (2006.01) | |
| *A61K 31/635* | (2006.01) | |
| *A61K 31/7056* | (2006.01) | |

(52) U.S. Cl.
CPC .......... *A61K 35/76* (2013.01); *A61K 31/4164* (2013.01); *A61K 31/505* (2013.01); *A61K 31/635* (2013.01); *A61K 31/7036* (2013.01); *A61K 31/7056* (2013.01); *A61K 38/14* (2013.01); *C12N 9/22* (2013.01); *A61K 48/005* (2013.01); *C12N 2310/20* (2017.05)

(58) Field of Classification Search
CPC ...... A61K 48/005; A61K 35/76; C12N 15/86; C12N 2800/202; C12N 2310/20; C07H 21/02; C07H 21/04
See application file for complete search history.

(56) References Cited

U.S. PATENT DOCUMENTS

| | | |
|---|---|---|
| 5,863,560 A | 1/1999 | Osborne |
| 7,482,115 B2 | 1/2009 | Scott et al. |
| 10,113,163 B2 | 10/2018 | Liu et al. |
| 2011/0218216 A1 | 9/2011 | Vivek et al. |
| 2015/0166980 A1 | 6/2015 | Liu et al. |

FOREIGN PATENT DOCUMENTS

| | | |
|---|---|---|
| WO | WO2020181178 A1 | 9/2020 |
| WO | WO2020181180 A1 | 9/2020 |
| WO | WO2020181193 A1 | 9/2020 |
| WO | WO2020181195 A1 | 9/2020 |
| WO | WO20200181202 A1 | 9/2020 |

OTHER PUBLICATIONS

Kotterman et al., 2014, Nature Reviews, vol. 15, p. 445-451.*
Shim et al., 2017, Current Gene Therapy, vol. 17, No. 5, p. 1-18.*
Lenzi et al., 2014, NCBI Bookshelf, a Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16.*
Durymanov et al., 2018, Frontiers in Pharmacology, vol. 9, Article 971, p. 1-15.*
Voorhees et al., 2020, Journal of Controlled Release, vol. 326, p. 106-119.*
Bryan et al., 2013, http://www.elsevierblogs.com/currentcomments/?p=962, Implications of protein fold switching, p. 1-4.*
Maqbool et al., 2015, Biochemical Society Transactions, vol. 43, No. 5, p. 1011-1017.*
Cruz et al., 2017, Methods in Molecular Biology, vol. 1654, Chapter 5, pp. 55-75.*
Ribet et al., 2015, Microbes and Infection, 17: 173-183.*
Maisch et al., Treatment options in myocarditis and inflammatory cardiomyopathy, Herz 2018 • 43:423-430.
Mamantopoulos et al. Nlrp6- and ASC-Dependent Inflammasomes Do Not Shape the Commensal Gut Microbiota Composition, 2017, Immunity 47, 339-348, Aug. 15, 2017.
Miki et al., The Bactericidal Lectin RegIIIb Prolongs Gut Colonization and Enteropathy in the Streptomycin Mouse Model for *Salmonella* Diarrhea, 2017, Cell Host & Microbe 21, 195-207, Feb. 8, 2017.

(Continued)

*Primary Examiner* — Shin Lin Chen
(74) *Attorney, Agent, or Firm* — Arrigo, Lee, Guttman & Mouta-Bellum LLP

(57) ABSTRACT

The invention relates to methods, kits and compositions for reducing the level of or eliminating *Bacteroides* in situ. The invention encompasses methods of preventing myocarditis, treating myocarditis or dilated cardiomyopathy, or limiting progression of myocarditis toward dilated cardiomyopathy in a subject in need thereof, comprising reducing the amount of *Bacteroides* sp. in the subject. The invention further encompasses methods of diagnosis of a subject as having myocarditis or dilated cardiomyopathy. The invention also encompasses compositions preventing myocarditis, treating myocarditis or dilated cardiomyopathy, or limiting progression of myocarditis toward dilated cardiomyopathy in a subject in need thereof.

7 Claims, 17 Drawing Sheets

Specification includes a Sequence Listing.

(56) References Cited

OTHER PUBLICATIONS

Myers et al., Cardiac myosin-Th17 responses promote heart failure in human myocarditis, JCI Insight. 2016;1(9):e85851, 1-19.
Nindl et al., Cooperation of Th1 and Th17 cells determines transition from autoimmune myocarditis to dilated cardiomyopathy, Eur. J. Immunol. 2012. 42: 2311-2321.
Oldstone et al., Molecular cornice and Autoimmune Disease, Cell, vol. 50, 819-820, Sep. 11, 1987.
Portig et al., HLA-DQB1* polymorphism and associations with dilated cardiomyopathy, inflammatory dilated cardiomyopathy and myocarditis, Autoimmunity, Jan. 2009; 42(1): 33-40.
Pummerer et al., Identification of Cardiac Myosin Peptides Capable of Inducing Autoimmune Myocarditis in BALB/c Mice, J. Clin. Invest. vol. 97, No. 9, May 1996, 2057-2062.
Rangachari et al., T-bet negatively regulates autoimmune myocarditis by suppressing local production of interleukin 17, J. Exp. Med. vol. 203, No. 8, Aug. 7, 2006 2009-2019.
Rose et al., Learning from myocarditis: mimicry, chaos and black holes, F1000Prime Reports 2014, 6:25, 1-7.
Tai et al., Microbial antigen mimics activate diabetogenic CD8 T cells in NOD mice, J. Exp. Med. 2016 vol. 213 No. 10, 2129-2146.
Taylor et al., A Spontaneous Model for Autoimmune Myocarditis Using the Human MHC Molecule HLA-DQ8, The Journal of Immunology, 2004, 172: 2651-2658.
Teng et al., Gut Microbiota Drive Autoimmune Arthritis by Promoting Differentiation and Migration of Peyer's Patch T Follicular Helper Cells, Immunity. Apr. 19, 2016; 44(4): 875-888.
Trachtenberg et al., Inflammatory Cardiomyopathic Syndromes, Circ Res. 2017;121:803-818.
Vanderlugt et al., Epitope Spreading in Immunemediated Diseases: Implications for Immunotherapy, Nature Reviews | Immunology vol. 2 | Feb. 2002 | 85-95.
Vatanen et al., Variation in Microbiome LPS Immunogenicity Contributes to Autoimmunity in Humans, Cell. May 5, 2016; 165(4): 842-853.
Weintraub et al., Dilated cardiomyopathy, Lancet 2017; 390: 400-14.
Zhang et al., Cardiotoxicity of Immune Checkpoint Inhibitors, Curr Treat Options Cardio Med (2019) 21: 32, 1-17.
Lee et al., Proinflammatory T-cell responses to gut microbiota promote experimental autoimmune encephalomyelitis, PNAS, Mar. 15, 2011, vol. 108, suppl. 1, 4615-4622.
Abudayyeh ey al., RNA targeting with CRISPR-Cas13a, Nature. Oct. 12, 2017; 550(7675): 280-284.
Anzalone et al., Search-and-replace genome editing without double-strand breaks or donor DNA, Nature. Dec. 2019 ; 576(7785): 149-157.
Barin et al., Control of inflammatory heart disease by CD4+ T cells, Ann. N.Y. Acad. Sci. 1285 (2013) 80-96.
Bikard et al., CRISPR Interference Can Prevent Natural Transformation and Virulence Acquisition during In Vivo Bacterial Infection, Cell Host & Microbe 12, 177-186, Aug. 16, 2012.
Bikard et al., Development of sequence-specific antimicrobials based on programmable CRISPR-Cas nucleases, Nat Biotechnol. Nov. 2014 ; 32(11): 1146-1150.
Buggey et al., Myocarditis and cardiomyopathy, Current Opinion, vol. 33, 2018, 1-6.
Bunker et al., Innate and adaptive humoral responses coat distinct commensal bacteria with immunoglobulin A, Immunity. Sep. 15, 2015; 43(3): 541-553.
Caporaso et al., QIIME allows analysis of high-throughput community sequencing data, Nat Methods. May 2010 ; 7(5): 335-336.
Chen et al., Precise and programmable C:G to G:C base editing in genomic DNA, bioRxiv preprint doi: https://doi.org/10.1101/2020. 07.21.213827; this version posted Jul. 21, 2020, 1-19.
Chen et al., Programmable C:G to G:C genome editing with CRISPR-Cas9-directed base excision repair proteins, Nature Communications | (2021) 12:1384 | https://doi.org/10.1038/s41467-021-21559-9 | www.nature.com/naturecommunications, 1-7.
Cox et al., RNA Editing with CRISPR-Cas13, Science. Nov. 24, 2017; 358(6366): 1019-1027.
Farzadfard et al., Genomically Encoded Analog Memory with Precise In vivo DNA Writing in Living Cell Populations, Science. Nov. 14, 2014; 346(6211), 1-18.
Fonfara et al., Phylogeny of Cas9 determines functional exchangeability of dual-RNA and Cas9 among orthologous type II CRISPR-Cas systems, Nucleic Acids Research, 2014, vol. 42, No. 4 2577-2590.
Gaudelli et al., Programmable base editing of A•T to G•C in genomic DNA without DNA cleavage, Nature. Nov. 23, 2017; 551(7681): 464-471.
Gil-Cruz et al., Microbiota-derived peptide mimics drive lethal inflammatory cardiomyopathy, Science 366, 881-886 (2019).
Grunewald et al., A dual-deaminase CRISPR base editor enables concurrent adenine and cytosine editing, Nat Biotechnol. Jul. 2020 ; 38(7): 861-864.
Karberg et al., Group II introns as controllable gene targeting vectors for genetic amnipulation of bacteria, Nature Biotechnology, vol. 19, Dec. 2001, 1162-1167.
Komor et al., Programmable editing of a target base in genomic DNA without double-stranded DNA cleavage, Nature. ; 533(7603): 420-424, available in PMC Oct. 20, 2016.
Koonin et al., Diversity, classification and evolution of CRISPR-Cas systems, Curr Opin Microbiol. Jun. 2017 ; 37: 67-78.
Kurt et al., CRISPR C-to-G base editors for inducing targeted DNA transversions in human cells, Nat Biotechnol. Jan. 2021 ; 39(1): 41-46.
Li et al., Targeted, random mutagenesis of plant genes with dual cytosine and adenine base editors, Nature Biotechnology vol. 38, pp. 875-882 (2020).
Chen et al., Skin microbiota-host interactions, Nature. Jan. 24, 2018; 553(7689): 427-436.
Citorik et al., Sequence-specific antimicrobials using efficiently delivered RNA-guided nucleases, Nat Biotechnol. Nov. 2014 ; 32(11): 1141-1145.
Cossarizza et al., Guidelines for the use of flow cytometry and cell sorting in immunological studies, Eur. J. Immunol. 2017. 47: 1584-1797.
Davidson et al., Autoimmune Diseases, N Engl J Med, vol. 345, No. 5, Aug. 2, 2001, 340-350.
Deubner et al., Cardiac b1-adrenoceptor autoantibodies in human heart disease: rationale and design of the Etiology, Titre-Course, and Survival (ETiCS) Study, European Journal of Heart Failure (2010) 12, 753-762.
Generali et al., Lessons learned from twins in autoimmune and chronic inflammatory diseases, Journal of Autoimmunity vol. 83, Sep. 2017, pp. 51-61.
Gerstmans et al., From endolysins to Artilysin®s: novel, enzyme-based approaches to kill drug-resistant bacteria, Biochem. Soc. Trans. (2016) 44, 123-128.
Gil-Cruz et al., Fibroblastic reticular cells regulate intestinal inflammation via IL-15-mediated control of group 1 ILCs, nature immunology, vol. 17 No. 12 Dec. 2016, 1388-1398.
Gopalakrishnan et al., Gut microbiome modulates response to anti-PD-1 immunotherapy in melanoma patients, Science. Jan. 5, 2018; 359(6371): 97-103.
Greenbaum et al., Functional classification of class II human leukocyte antigen (HLA) molecules reveals seven different supertypes and a surprising degree of repertoire sharing across supertypes, Immunogenetics. Jun. 2011 ; 63(6): 325-335.
Hebbandi Nanjundappa et al., A Gut Microbial Mimic that Hijacks Diabetogenic Autoreactivity to Suppress Colitis, Cell 171, 655-667, Oct. 19, 2017.
Heymans et al., The Quest for New Approaches in Myocarditis and Inflammatory Cardiomyopathy, Journal of the American College of Cardiology, vol. 68, No. 21, 2016, 2348-64.
Hickey et al., Colitogenic Bacteroides thetaiotaomicron antigens access host immune cells in a sulfatase-dependent manner via outer membrane vesicles, Cell Host Microbe. May 13, 2015; 17(5): 672-680.
Honda et al., The microbiota in adaptive immune homeostasis and disease, Nature Jul. 7, 2016, vol. 535, 75-84.

(56) References Cited

OTHER PUBLICATIONS

Rees et al., Base editing: precision chemistry on the genome and transcriptome of living cells, Nat Rev Genet. Dec. 2018 ; 19(12): 770-788.
Sharon et al., Functional genetic variants revealed by massively parallel precise genome editing, Cell. Oct. 4, 2018; 175(2): 544-557.
Simon et al., Retrons and their applications in genome engineering, Nucleic Acids Research, 2019, vol. 47, No. 21 11007-11019, Published online Oct. 10, 2019.
Wannier et al., Improved bacterial recombineering by parallelized protein discovery, bioRxiv preprint doi: https://doi.org/10.1101/2020.01.14.906594, uploaded on Feb. 26, 2020.
Weigele et al., Biosynthesis and Function of Modified Bases in Bacteria and Their Viruses, Chem. Rev. 2016, 116, 12655-12687, Published: Jun. 20, 2016.
Yan et al., Cas13d is a compact RNA-targeting type VI CRISPR effector positively modulated by a WYL domain-containing accessory protein, Mol Cell. Apr. 19, 2018; 70(2): 327-339.
Zhao et al., New base editors change C to A in bacteria and C to G in mammalian cells, Nature Biotechnology vol. 39, pp. 35-40 (2021).
Horai et al., Microbiota-dependent activation of an autoreactive T cell receptor provokes autoimmunity in an immunologically privileged site, Immunity. Aug. 18, 2015; 43(2): 343-353.
Jiang et al., CRISPR-assisted editing of bacterial genomes, Nat Biotechnol. Mar. 2013 ; 31(3): 233-239.
Johnson et al., Fulminant Myocarditis with Combination Immune Checkpoint Blockade, N Engl J Med. Nov. 3, 2016; 375(18): 1749-1755.
Koropatkin et al., Starch catabolism by a prominent human gut symbiont is directed by the recognition of amylose helices, Structure. Jul. 2008 ; 16(7): 1105-1115.
Krebs et al., Molecular mapping of autoimmune B cell responses in experimental myocarditis, Journal of Autoimmunity 28 (2007) 224-233.
Krom et al., Engineered Phagemids for Nonlytic, Targeted Antibacterial Therapies, Nano Letters 2015, 15, 7, 4808-4813.
Liu et al., HLA-DQA1, -DQB1 Polymorphism and Genetic Susceptibility to Idiopathic Dilated Cardiomyopathy in Hans of Northern China, Annals of Human Genetics (2005) 69,382-388.
Lv et al., Impaired thymic tolerance to α-myosin directs autoimmunity to the heart in mice and humans, the Journal of Clinical Investigation, vol. 121, No. 4, Apr. 2011.

\* cited by examiner

ELIMINATION OF COLONIC BACTERIAL DRIVING LETHAL INFLAMMATORY CARDIOMYOPATHY

CROSS REFERENCE TO RELATED APPLICATIONS

This application claims the benefit of U.S. application 63/007,197 filed Apr. 8, 2020, which is herein incorporated by reference in its entirety.

The instant application contains a Sequence Listing which has been submitted electronically in ASCII format and is hereby incorporated by reference in its entirety. Said ASCII copy, created on Jun. 9, 2021, is named EB2020-03_USreg_Amended_Sequence.txt and is 17,810 bytes in size.

BACKGROUND OF THE INVENTION

The human microbiota comprises bacteria, archaea, viruses, and microbial eukaryotes living in our bodies. The taxonomic composition of these communities has been extensively studied and is significantly associated with a variety of diseases and traits. This microbiota indeed consists of thousands of different bacterial species that carry hundreds of billions of genes, which is called the microbiome. This microbiome encodes for a variety of molecules (proteins, lipids, sugars, RNA, etc.) and functions that are essential and beneficial for their host, for instance the enrichment of glycans metabolism, amino acids and xenobiotics but also the regulation of our immune system. It is also responsible for the synthesis of vitamins, isoprenoids and other nutrients which results in human overall metabolism representing an amalgamation of microbial and human attributes.

Interestingly, there is a growing body of recent studies based on metagenome sequencing that demonstrate that the presence of specific strains (and therefore of specific genetic signatures in the microbiome) can be directly linked to a number of pathologies, including auto-immunity, infections, inflammation or tumorigenesis.

Myocarditis is an inflammatory heart disease that develops into lethal inflammatory cardiomyopathy in 20-30% of the patients (1, 2). Myocarditis can develop into inflammatory cardiomyopathy through chronic stimulation of myosin heavy chain 6-specific Th1 and Th17 cells. However, the mechanisms that govern the cardiotoxicity programming of heart-specific T cells have remained elusive. It is well established that acute immune activation after infectious myocarditis is associated with the generation of autoimmune responses against myosin heavy chain 6 (MYH6) (3-5), while subsequent chronic stimulation of MYH6-specific Th1 and Th17 cells precipitates inflammatory cardiomyopathy (6-9). Nevertheless, it is still unclear which mechanisms mediate the initial activation and cardiotoxicity programming of heart-specific T cells. Likewise, therapeutic approaches that mitigate the activity of such pathogenic T cells and prevent the severe consequences of inflammatory cardiomyopathy are still limited (10, 11).

A cardinal challenge in deciphering the progressive nature of autoimmune and chronic inflammatory diseases is the deconvolution of their multifactorial nature, which is determined by different degrees of genetic susceptibility and a multitude of environmental conditions (12, 13). The quest for genetic determinants underlying susceptibility to myocarditis and dilated cardiomyopathy (DCM) has revealed associations with HLA-DQB1* polymorphisms (14, 15). Moreover, the development of progressive myocarditis in transgenic mice expressing the HLA-DQ8 haplotype (encoded by the DQA1*03:01/DQB1*03:02 alleles) (7, 16) indicates that antigen presentation via certain MHC class II molecules is a major determinant of myocarditis.

A variety of pathogens including enteroviruses, *Borrelia burgdorferi* and *Trypanosoma cruzi* can cause cardiac damage leading to myocarditis thereby predisposing affected patients for inflammatory cardiomyopathy (11). Still, the question whether and to which extent pathogen-induced death of cardiomyocytes results in the excessive presentation of self-antigens to MHC class II-restricted T cells or whether antigenic mimicry of microbial components drives the disease has remained unanswered (10, 11). The present invention fulfills this need.

BRIEF SUMMARY OF INVENTION

The invention relates to methods, kits and compositions for reducing the level of or eliminating a *Bacteroides* bacteria in situ. Preferably, the *Bacteroides* are killed.

The invention encompasses methods of preventing myocarditis, treating myocarditis or dilated cardiomyopathy (DCM), or limiting progression of myocarditis toward DCM in a subject in need thereof, comprising reducing the amount of *Bacteroides* sp. in the subject.

The invention encompasses methods of diagnosis of a subject as having myocarditis or DCM, comprising obtaining a biological sample of the subject, quantifying the amount of *Bacteroides* sp. in the biological sample relative to a control sample.

The invention also encompasses methods of treating myocarditis or DCM in a subject, comprising obtaining a biological sample of the subject, quantifying the amount of *Bacteroides* sp. in the biological sample relative to a control sample, and when the amount of *Bacteroides* sp. is higher in the biological sample relative to a control sample, reducing the amount of *Bacteroides* sp. in the subject.

The invention encompasses compositions preventing myocarditis, treating myocarditis or DCM, or limiting progression of myocarditis toward DCM in a subject in need thereof. Preferably, the compositions kill *Bacteroides* bacteria. Alternatively, the compositions may reduce the amount of *Bacteroides* sp. in the subject without killing *Bacteroides* bacteria.

In various embodiments, the method comprises administering to the subject an effective amount of an antibiotic, bacteria, engineered bacteria, phage, recombinant phage, packaged phagemid, wild-type or synthetic endolysin, wild-type or synthetic bacteriocin or any combination thereof.

In various embodiments, the composition comprises an effective amount of an antibiotic, engineered bacteria, phage, recombinant phage, packaged phagemid, endolysin, bacteriocin or any combination thereof.

In various embodiments, the antibiotic is selected from streptomycin, vancomycin, clindamycin, metronidazole, sulphadoxine, trimethoprim, or any combination of 1, 2, 3, 4, 5 or 6 of these antibiotics.

In various embodiments, the phage, recombinant phage or packaged phagemid encodes an endolysin.

In various embodiments, the phage, recombinant phage, packaged phagemid encodes a nuclease selected from CRISPR-Cas, TALENs and variants, zinc finger nuclease (ZFN) and ZFN variants, natural, evolved or engineered meganuclease or recombinase variants.

In various embodiments, the bacteria or engineered bacteria does not produce MYH6 mimic peptides (in particular mimics of $MYH6_{614-629}$ or $MYH6_{614-628}$ peptides, typically of sequence SEQ ID NO: 10, 16 or 17), more particularly which does not produce β-gal$_{11-25}$ peptide (typically of sequence SEQ ID NO: 11, 12, 18, 19, 20, 21 or 22), still particularly does not produce a β-galactosidase.

In various embodiments, the *Bacteroides* is *B. thetaiotaomicron* and/or *B. faecis*. Preferably, the *Bacteroides* is *B. thetaiotaomicron* and/or *B. faecis* which produce MYH6 mimic peptides (in particular mimics of MYH6$_{614-629}$ or MYH6$_{614-628}$ peptides, typically of sequence SEQ ID NO: 10, 16 or 17), more particularly which produce β-gal$_{11-25}$ peptide (typically of sequence SEQ ID NO: 11, 12, 18, 19, 20, 21 or 22).

The invention encompasses the following embodiments:

A method of preventing myocarditis in a subject in need thereof, comprising reducing the amount of *Bacteroides* sp. in a subject.

A method of treating myocarditis or DCM in a subject in need thereof, comprising reducing the amount of *Bacteroides* sp. in a subject.

A method of limiting progression of myocarditis toward DCM in a subject in need thereof, comprising reducing the amount of *Bacteroides* sp. in a subject.

A method of diagnosis a subject as having myocarditis or DCM, comprising obtaining a biological sample of the subject, quantifying the amount of *Bacteroides* sp. in the biological sample relative to a control sample.

Any of these methods, comprising administering to the subject an effective amount of an antibiotic, phage, recombinant phage, packaged phagemid, bacteria, engineered bacteria, bacteriocin or endolysin. In some embodiments, the antibiotic is selected from streptomycin, vancomycin, clindamycin, metronidazole, sulphadoxine, trimethoprim, or any combination of 1, 2, 3, 4, 5 or 6 of these antibiotics. In some embodiments, the phage, recombinant phage or packaged phagemid encodes a nuclease selected from CRISPR-Cas, TALENs and variants, zinc finger nuclease (ZFN) and ZFN variants, natural, evolved or engineered meganuclease or recombinase variants. In some embodiments, the *Bacteroides* is *B. thetaiotaomicron* and/or *B. faecis*.

A composition for preventing myocarditis in a subject in need thereof, comprising a pharmaceutical agent which reduces the amount of *Bacteroides* sp. in a subject.

A composition for treating myocarditis or DCM in a subject in need thereof, comprising a therapeutic agent which reduces the amount of *Bacteroides* sp. in a subject.

A composition for limiting progression of myocarditis toward DCM in a subject in need thereof, comprising a pharmaceutical agent which reduces the amount of *Bacteroides* sp. in a subject.

Any of these compositions, comprising an effective amount of an antibiotic, phage, recombinant phage, packaged phagemid, bacteria, engineered bacteria, bacteriocin or endolysin. In some embodiments, the antibiotic is selected from streptomycin, vancomycin, clindamycin, metronidazole, sulphadoxine, trimethoprim, or any combination of 1, 2, 3, 4, 5 or 6 of these antibiotics. In some embodiments, the phage, recombinant phage or packaged phagemid encodes a nuclease selected from CRISPR-Cas, TALENs and variants, zinc finger nuclease (ZFN) and ZFN variants, natural, evolved or engineered meganuclease or recombinase variants. In some embodiments, the *Bacteroides* is *B. thetaiotaomicron* and/or *B. faecis*.

BRIEF DESCRIPTION OF DRAWINGS

(FIG. 1A) Survival of TCRM mice under SPF or GF conditions. (FIG. 1H) Schematic representation of co-housing experiments. (FIG. 1I) Prospective survival analysis of TCRM mice, arrowheads indicate the age of transfer to SPF conditions. (FIG. 1J) Development of myocarditis in TCRM mice under SPF, GF and co-housing conditions; dots represent disease severity in individual mice; bar indicates mean disease severity. (FIG. 1O-R) Heart-infiltrating myeloid cell subsets from SPF, GF or 4 week cohoused TCRM mice analyzed by flow cytometry; dots represent values from individual mice, line indicates mean value. (FIG. 1O) Representative tSNE plots of myeloid cells in the heart of TCRM SPF mice. Enumeration of (FIG. 1P) inflammatory monocytes, (FIG. 1Q) MHCII$^{high}$ macrophages and (FIG. 1R) MERTK$^+$ macrophages in the heart (mean±SEM). Pooled data from 2 independent experiments n=5-6 mice (FIG. 1K, L, P-R) or three independent experiments with ≥15 mice (FIGS. 1A and I), ≥12 mice (FIGS. 1B, C and D), ≥6 mice (FIG. 1E-G), ≥11 mice (FIG. 1J) ≥7 mice (FIG. 1M) per group. Representative micrographs of hearts and heart sections from one out of at least 12 mice (FIG. 1A, B). Statistical analysis was performed using Student's t test (FIG. 1D) or one-way ANOVA with Dunnett's multiple comparison test (FIGS. 1E-G, J-N and P-R) with *, $p<0.05$; , $p<0.01$; *, $p<0.001$.

(FIG. 2A) Flow cytometric analysis of mucosal homing markers in heart-infiltrating MYH6 specific cells from SPF or GF TCRM mice. (FIG. 2B-C) Location and proliferation of CFSE-labelled TCRM cells after adoptive transfer to Rag1$^{-/-}$ mice. (FIG. 2B) Confocal microscopy analysis of colonic patches at day 3 post adoptive transfer, scale bar 100 μm (FIG. 2C) Proliferation of MYH6-specific cells flow cytometry-based quantification of CFSE dilution in the indicated organs and at the indicated time points (mean±SEM). (FIGS. 2D[-F]) Microbiome analysis of 12 week old transgene-negative littermate controls (Tg$^-$), SPF TCRM and GF TCRM mice co-housed at 4 weeks of age under SPF conditions. (FIG. 2E) Principal component analysis of the fecal bacterial composition. (FIG. 2F) Heat map of the relative abundance of the indicated bacterial classes and families in feces. (FIG. 2G-H) MYH6-specific CD4$^+$ T cell crossreactivity. (FIG. 2G) In vitro proliferation of CD4$^+$ T cells from TCRM mice after re-stimulation with MYH6, β-gal peptide from *Bacteroides* and cysteine hydrolase-derived peptide from *Enterobacter* determined by CFSE dilution assay. (FIG. 2H) Cytokine production of heart- and colon-infiltrating, Vβ8-expressing CD4+ T cells from TCRM mice under SPF conditions after ex vivo re-stimulation with MYH6 peptide and *Bacteroides* β-gal peptide (box and whiskers show mean±interquartile range). (FIG. 2I-M) GF TCRM mice were monocolonized with parental *B. thetaiotaomicron* (wild type, WT) or *B. thetaiotaomicron* lacking the β-galactosidase BT1626 (*B. thetaiotaomicron* Δβ-gal). (FIG. 2I) Schematic representation of the experimental setting. Flow cytometric analysis of (FIG. 2J) heart-infiltrating cells and (FIG. 2K) MYH6-specific cytokine producing cells in the heart and colon (box and whiskers show mean±interquartile range). (FIG. 2L) IgA bound fecal bacteria determined by bacterial flow cytometry and (FIG. 2M) pooled data shown as mean±SEM. Pooled data from n=6 (FIG. 2A-F, J-M), n=7 (FIG. 2G) and n=5 (FIG. 2H) mice from at least two independent experiments. Representative histograms from two independent experiments with duplicates (FIG. 2G). Statistical analysis was performed using Student's t test (FIG. 2A, H, J, K, M) or one-way ANOVA with Dunnett's multiple comparison test (FIG. 2F) with *, $p<0.05$; , $p<0.01$; *, $p<0.001$.

(FIG. 3A) Survival, (FIG. 3B) disease severity, and (FIG. 3C) histological analysis of hearts of TCRM mice after post-weaning oral treatment with a broad spectrum antibiotics combination comprising of Sulphadoxine, Trimethoprim and Metronidazole (S+T+M); disease severity was determined in 20 week old mice; dots represent values of individual mice; bar indicates mean disease severity. (FIG. 3D-J) Effect of antibiotics treatment regimen on myocarditis progression in the adoptive transfer myocarditis model. (FIG. 3D) Schematic representation of the experimental set up. (FIG. 3E) *B. thetaiotaomicron* quantification in feces of mice by qPCR in the indicated treatment groups. (FIG. 3F) Histopathological analysis of hearts from Rag1$^{-/-}$ mice treated with antibiotics at day 28; dots represent values of individual mice; bar indicates mean disease severity. Quantification of heart-infiltrating CD45+ cells (FIG. 3G) and Vβ8-expressing CD4+ T cells (FIG. 3H) in Rag1$^{-/-}$ mice at day 28. (FIG. 3I) Cytokine production of heart-infiltrating MYH6-specific Vβ8+CD4+ T cells (box and whiskers show mean±interquartile range). (FIG. 3J) Heat map representation of the specific IgG responses against *B. thetaiotaomicron, B distasonis, B. vulgatus* and *E. cloaceae* determined by ELISA. (FIG. 3K) *B. thetaiotaomicron*-specific IgG response in sera of BALB/c mice or BALB/c mice adoptively transferred with CD4+ TCRM T cells (box and whiskers show mean±interquartile range). Pooled data from two to three independent experiments with n=7-10 (FIG. 3A-C), n=5-13 mice (FIG. 3G-J) and n=5-7 (FIG. 3K). Representative sections from one out of 10 or 7 mice (FIG. 3C). Statistical analysis was performed using Student's t test (FIG. 3K) or Mann-Whitney test (FIG. 3B); one-way ANOVA with Dunnett's multiple comparison test (FIG. 3E-I) with *, $p<0.05$; , $p<0.01$; *, $p<0.001$.

(FIG. 4A) Analysis of *B. thetaiotaomicron*-specific IgG antibodies in sera of myocarditis patients from the AMITIS cohort at first admission and different time points post-diagnosis compared to sera from a cohort of healthy individuals, light grey and dark grey squares indicate patients with high or low anti-*B. thetaiotaomicron* antibody levels respectively, cut value was determined as the mean+2SD of the healthy group; dots represent individual antibody levels, bar indicates mean value. (FIG. 4B) Ejection fraction (EF) and (FIG. 4C) C-reactive protein (CRP) values in patients from the AMITIS cohort at the indicated time points; individual values are shown, bar represents mean value. (FIG. 4D) Composite clinical scores of myocarditis patients from the AMITIS cohort with low vs high IgG antibodies against *B. thetaiotaomicron* at the first visit (as indicated in A); dots represent individual clinical scores as the sum of positivity for anti-beta1-AR antibodies, CRP values ≥16 and proportion of EF ≤40. (FIG. 4E-F) Anti-bacterial IgG antibody responses in sera of myocarditis patients and healthy controls. (FIG. 4E) Heat map representation of specific IgG response against *B. thetaiotaomicron, B. distasonis, B. vulgatus* and *E. cloacae* in the AMITIS cohort. (FIG. 4F) *B. thetaiotaomicron*-specific IgG in serum of patients of the Micro-DCM cohort at admission (individual values are shown, bar indicates mean value) and (FIG. 4G) heat map representation of antibacterial IgG reactivity in the Micro-DCM cohort. (FIG. 4H) Heat maps representing the binding of the MYH6$_{614-629}$ peptide or the *B. thetaiotaomicron* β-gal$_{11-25}$ peptide. The in-silico analysis was done for molecules that cover the 99% of the HLA-DQ alleles in open population. (FIG. 4I) IFN-γ ELISPOT analysis of peripheral blood mononuclear cells of HLA-DQB1*03 healthy volunteers (n=10) or patients from the Micro-DCM cohort (HLA-DQB1*03 n=9; other HLA n=8) after stimulation with the human-MYH6$_{614-629}$ peptide or the *B. thetaiotaomicron* β-gal$_{11-25}$ peptides (violin plots show mean±interquartile range). (FIG. 4J) Schematic representation of fecal transplant experiment using stool from two myocarditis patients (HLA-DQB1*03:02 haplotype and *B. thetaiotaomicron* 16S rRNA-positive) to GF TCRM or transgene-negative (Tg$^-$) control mice. (FIG. 4K) *B. thetaiotaomicron* quantification in feces of TCRM or Tg$^-$ controls at the indicated times post fecal transplantation (box and whiskers show mean±interquartile range). (FIG. 4L-M) Enumeration of heart-infiltrating CD45+ immune (FIG. 4L) and CD4+ T cells (FIG. 4M) in recipient mice at 4 weeks after fecal transplantation (mean±SEM). Statistical analysis was performed using one-way ANOVA with Dunnett's multiple comparison test (FIGS. 4A-C and I) or Mann-Whitney U test (FIG. 4D) or Student's t test (FIGS. 4E-D and (L-M) with *, $p<0.05$; , $p<0.01$; *, $p<0.001$.

(FIG. 5A-C) Echocardiographic parameters in TCRM mice under SPF, GF and co-housing conditions with (FIG. 5A) ejection fraction, (FIG. 5B) systolic left ventricular internal diameter (LVID) and (FIG. 5C) fractional shortening determined in individual mice. (FIG. 5D-F) Flow cytometric analysis of heart-infiltrating myeloid cells. Representative dot plots showing CCR2 and Ly6C (FIG. 5D) and CD64 and MHCII expression (FIG. 5E) shown as percentage of CD11b+ Ly6G$^-$ cells depicted for each condition. (FIG. 5F) Enumeration of different subpopulations of myeloid cells in TCRM mice kept under the indicated conditions (mean values±SEM; n=5-8 mice per group). Statistical analysis was performed using one-way ANOVA with Dunnett's multiple comparison test with *, $p<0.05$; , $p<0.01$; *, $p<0.001$.

(FIG. 6A) Schematic representation of the experimental set up for the analysis of homing and early proliferation of CFSE-labelled TCRM cells in Rag$^{-/-}$ mice. (FIG. 6B-C) Histological analysis of colonic (FIG. 6B) and mesenteric (FIG. 6C) lymph nodes of Rag$^{-/-}$ mice 3 days after a.t. of CFSE labelled TCRM cells, scale bar=30 μm. (FIG. 6D) Flow cytometric analysis of the proliferation patterns of TCRM cells in the colonic lamina propria and heart at the indicated time points after a.t. to Rag$^{-/-}$ mice; percentages indicate CFSE$^{low/neg}$ MYH6-specific cells in the indicated organs. (FIG. 6E) Cytokine profiles of heart-infiltrating and colonic Vβ8-expressing CD4$^+$ T cells from TCRM mice at the indicated time points analyzed by flow cytometry (mean±SEM). (FIG. 6F) Flow cytometry-based cytokine profile analysis of Vβ8-expressing CD4$^+$ T cells from the colonic lamina propria of TCRM mice or transgene-negative littermates (Tg$^-$). (FIG. 6G) Production of IFN-© and IL-17 by colonic CD4$^+$ T cells from TCRM mice or DO11.10 mice after ex-vivo re-stimulation with MYH6$_{614-629}$; representative dot-plots are shown. (FIG. 6H) Bacterial α-diversity in feces of 12 week old TCRM mice and transgene-negative littermates (Tg–) under SPF conditions. (FIG. 6I) Relative abundance of *Bacteroides* and *Parabacteroides* in fecal samples of 12 weeks of age TCRM or Tg$^-$ mice under SPF or cohousing conditions (box and whiskers show mean±interquartile range). (n=5-13 mice per group from 2-3 independent experiments). Statistical analysis was performed using Student's t test or one-way ANOVA with Dunnett's multiple comparison test with *, p<0.05; , p<0.01; *, p<0.001.

(FIG. 7A) In vitro proliferation of CD4$^+$ T cells from TCRM mice or DO11.10 mice measured by CFSE dilution after re-stimulation with MYH6 or *Bacteroides* β-galactosidase peptide or ovalbumin peptide at indicated concentration (representative histograms from 1 out of 2 experiments) (FIG. 7B) Dendritic cells loaded with MYH6 or β-gal peptide from *Bacteroides* at the indicated concentration were co-cultured in vitro with CD4$^+$ T cells from TCRM mice. Maximum proliferation of CD4$^+$ T cells was analyzed by flow cytometry and effective concentration 50 (EC$_{50}$) for each peptide was determined. (FIG. 7C) CD4$^+$ T cells from TCRM mice were adoptively transferred into BALB/c mice. Proliferation of CD4$^+$ T cells from TCRM mice was determined ex vivo by CFSE dilution after injection of peptide loaded dendritic cells (n=3). (FIG. 7D-FIG. 7E) Colonization of GF TCRM mice with SPF microbiota or *B. thetaiotaomicron* or *E. coli*. Induction of IFN-© and IL-17 in Vβ8-expressing CD4$^+$ T cells in the colonic lamina propria of TCRM mice at 8 weeks after bacterial colonization. Fold increase values were calculated using the cytokine production in GF mice as baseline (mean±SEM). (FIG. 7F) Strategy for the generation of the β-galactosidase BT1626 deficient *B. thetaiotaomicron* strain. (FIG. 7G) Colonization efficiency of WT the parental *B. thetaiotaomicron* (ATCC29148$^{\Delta t dk}$) and the Δβ-gal *B. thetaiotaomicron* (ATCC29148$^{\Delta t dk}$ lacking the BT1626 β-galactosidase) in GF BALB/c mice (mean±SEM). (FIG. 7H-I) Bacterial flow of fecal IgA bound bacteria in TCRM and Tg$^-$ 12 weeks old mice. (FIG. 7H) experimental dosing, (FIG. 7I) representative dot plots left and quantification right of IgA bound bacteria; background was set using samples from Rag$^{-/-}$ mice (mean±SEM). (n=3-11 mice per group from 2-3 independent experiments). Statistical analysis was performed using Student's t test or one-way ANOVA with Dunnett's multiple comparison test with *, p<0.05; , p<0.01; *, p<0.001

(FIG. 8A) Microbiota composition analysis by 16S rRNA sequencing of mice treated with a broad spectrum antibiotics cocktail containing sulphadoxine, trimethoprim and metronidazole (S+T+M) compared to untreated TCRM mice. (FIG. 8B-F) Rag1$^{-/-}$ mice were adoptively transferred with 10$^6$ splenocytes from TCRM mice and treated with the indicated antibiotics. Flow cytometry-based enumeration of colonic (FIG. 8B) CD45$^+$ and (FIG. 8C) Vβ8-expressing CD4$^+$ T and (FIG. 8D) Vβ8-expressing CD4$^+$ T cells in spleens. (FIG. 8E) Cytokine production of heart infiltrating Vβ8-expressing CD4$^+$ T cells with representative dot plots. (FIG. 8F) IFN-© and IL-17 production in colonic Vβ8-expressing CD4$^+$ T cells. Box and whiskers show mean±interquartile range; n=6-8 mice from 2 or 3 independent experiments. Statistical analysis was performed using one-way ANOVA with Dunnett's multiple comparison test with *, p<0.05; , p<0.01; *, p<0.001.

(FIG. 9A-C) Clinical parameters at admission in *B. theta* high or low AMITIS patients. Antibody responses in patients from the AMITIS (FIG. 9D-F) and Micro-DCM (FIG. 9G-J) cohorts compared to healthy individuals. IgG antibodies against *E. cloacae* (FIG. 9D and FIG. 9G), *E. coli* (FIG. 9E and FIG. 9H), *B. distasonis* (FIG. 9I) and *B. vulgatus* (FIG. 9J) were determined by ELISA and total IgG concentrations (FIG. 9F) were determined by turbidimetry; dots represent individual patients, bar indicates mean values. (FIG. 9K) Correlation between MYH6- or β-gal IFN-γ-producing cells in myocarditis patients of the Micro-DCM cohort and healthy individuals with the indicated HLA-DQB1 alleles; dots represent individual values. (FIG. 9L) Graphical representation of the multiple risk factors that regulate the outcome of inflammatory cardiomyopathy. Statistical analysis was performed using Student's t test (FIG. 9G-J) or one-way ANOVA with Dunnett's multiple comparison test with (FIG. 9D-F) or Pearson correlation coefficient with two tailed P-value calculation.*, p<0.05.

DETAILED DESCRIPTION OF INVENTION

The present invention unveils the hitherto unknown connection between the microbiome and inflammatory cardiac disease in humans. The inventors show here that commensal bacteria such as *Bacteroides* can serve as a source of a mimic peptide that promotes the progression of myocarditis to inflammatory cardiomyopathy. The presented invention also shows that reducing the level of or eliminating *Bacteroides* in situ with treatment such as antibiotics can prevent lethal heart failure.

Figure 9A:
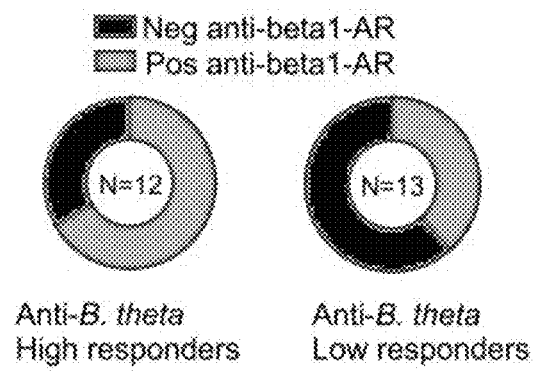
FIGS. 9A-L. B and T cell responses in myocarditis patients.
Figure 9B:
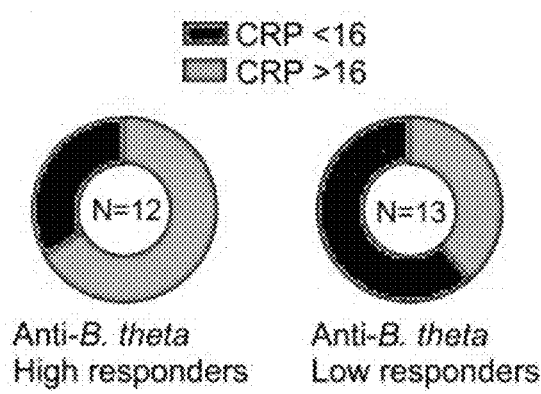
Figure 9C:
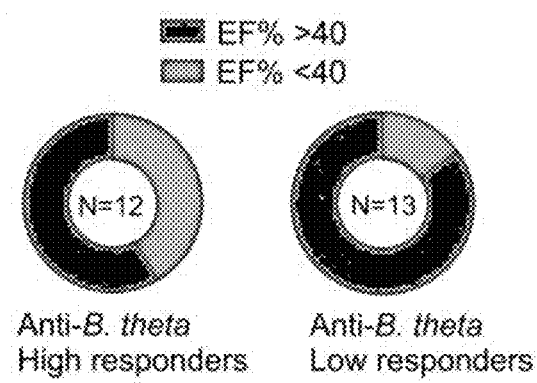
Figure 9D:
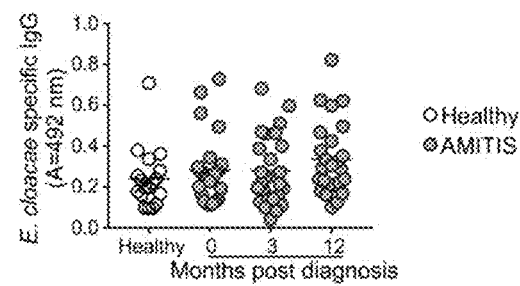
Figure 9E:
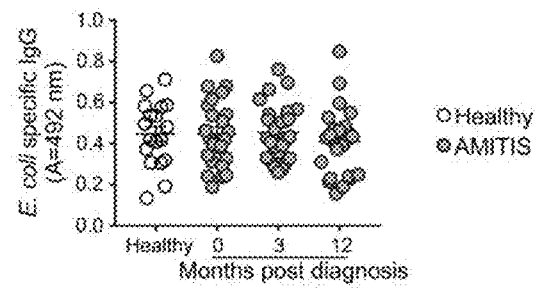
Figure 9F:
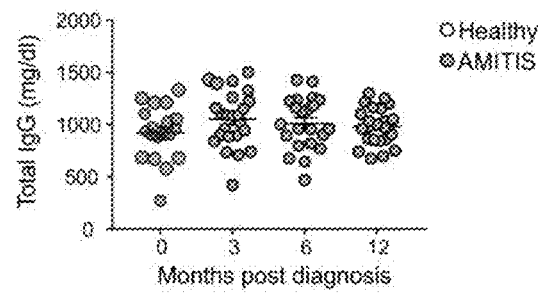
Figure 9G:
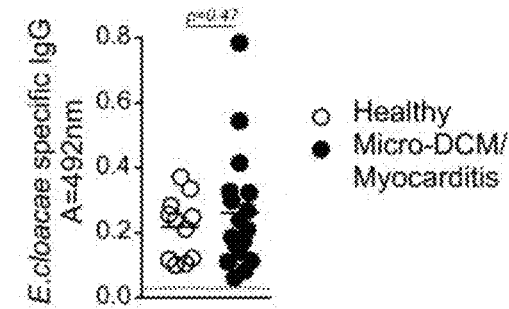
Figure 9H:
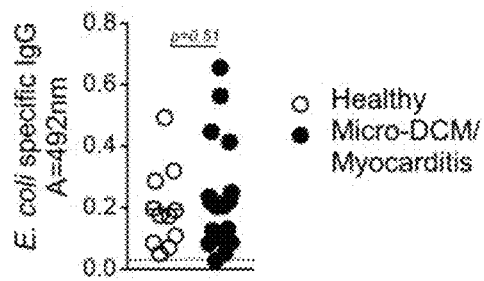
Figure 9J:
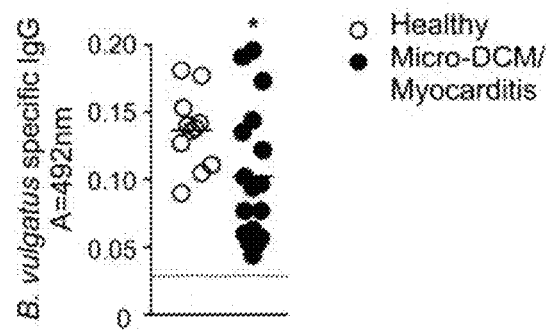
Figure 9I:
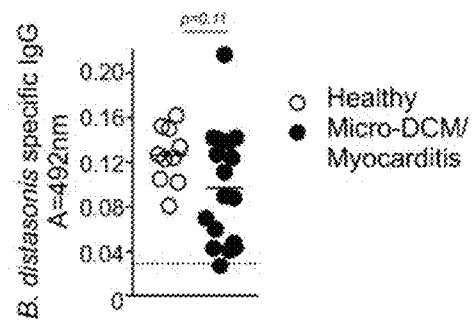
Figure 9K:
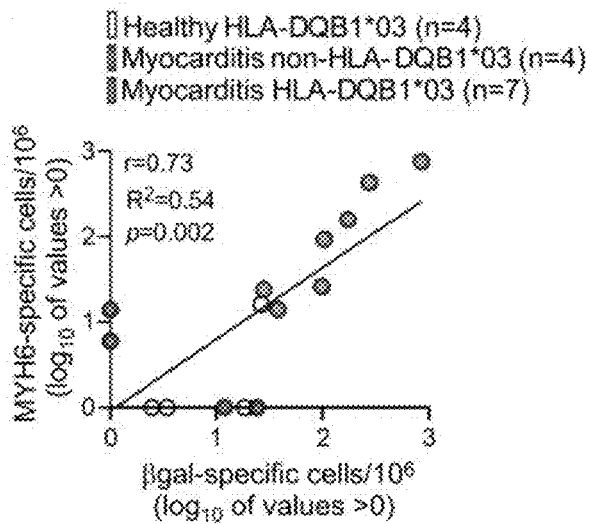
Figure 9L:
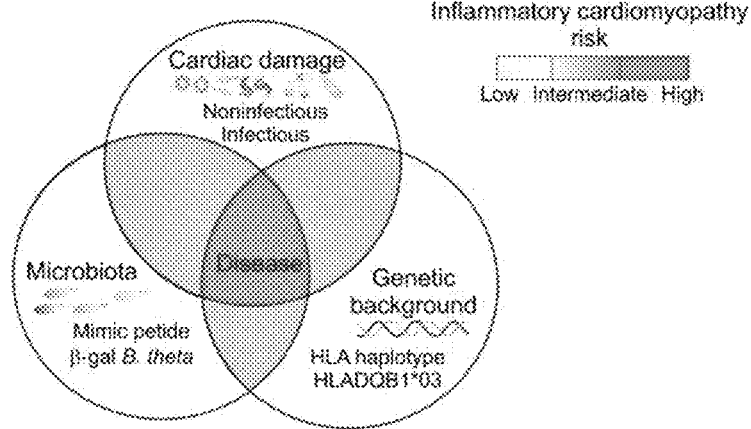

In at least a substantial proportion of myocarditis patients, the presence of specific bacteria in the intestinal microbiome that produce MYH6 mimic peptides and the genetic background with the particular set of HLADQB1*03 alleles determine the risk for the development of inflammatory myocarditis (FIG. 9L). In this scenario, cross-reactive CD4$^+$ T cells primed in intestinal microenvironments can enter the myocardium and exacerbate the damage caused by noxious agents or processes such as infection by cardiotropic viruses or subclinical myocardial infarction (FIG. 9L). Likewise, unleashing control over self- and cross-reactive T cells during immune checkpoint inhibitor therapy might be a reason for potentially lethal cardiac inflammation (30). Indeed, fulminant myocarditis during combination immune checkpoint blockade was found to affect patients who shared the HLADQB1*03:01 allele (31). Thus, the invention provides the rationale for extended prospective clinical trials to further dissect the connection between the microbiome-driven activation of cross-reactive CD4$^+$ T cells, HLA-dependent genetic predisposition and inflammatory cardiomyopathy. Targeting of the microbiome of genetically predisposed myocarditis patients or susceptible patients undergoing checkpoint inhibitor treatment through antibiotics may alleviate disease severity and can therefore contribute to the prevention of the potentially lethal sequelae of inflammatory cardiomyopathy.

To treat microbiome-associated diseases or disorders, unwanted *Bacteroides*, typically unwanted *Bacteroides* producing MYH6 mimic peptides, can be eliminated by using subtractive methods such as antibiotics, phages, recombinant phages, packaged phagemids, wild-type of synthetic endolysins, wild-type of synthetic bacteriocins (such as colicins, pyocins and/or tailocins) which result in the killing of deleterious *Bacteroides* bacteria or by using competitive methods such as bacteria or engineered bacteria which do not produce said MYH6 mimic peptides and preferably present a competitive advantage over unwanted *Bacteroides*, which results in the replacement of deleterious *Bacteroides* bacteria by said non-deleterious bacteria or engineered bacteria. Such strategies can significantly reduce the load of *Bacteroides* populations.

The invention encompasses compositions, kits and methods for eliminating a *Bacteroides* bacteria in situ. The compositions, kits and methods of the invention eliminate deleterious *Bacteroides* bacteria, in particular *Bacteroides* bacteria producing MYH6 mimic peptides (in particular mimics of $MYH6_{614-629}$ or $MYH6_{614-628}$ peptides, typically of sequence SEQ ID NO: 10, 16 or 17), more particularly *Bacteroides* bacteria producing $\beta$-$gal_{11-25}$ peptide (typically of sequence SEQ ID NO: 11, 12, 18, 19, 20, 21 or 22), within the host microbiome by killing or reducing the growth of these *Bacteroides*.

The invention encompasses the use of a vector that can transfer with high efficiency a nucleic acid, preferably a plasmid, into a bacterial population within the microbiome that allows the expression of an exogenous enzyme that will modify a gene sequence or directly kill the *Bacteroides* bacteria. The invention further includes methods for screening for elimination of the *Bacteroides*, for determining the efficiency of vectors at eliminating these *Bacteroides*, and for determining the effects of these vectors. Preferably, the elimination of *Bacteroides* bacteria in situ involves the use of antibiotics, of wild-type of synthetic bacteriocins, the use of phages, recombinant phage, packaged phagemid, wild-type of synthetic endolysins, introducing a double strand break in the DNA sequence, or any combination thereof. In an embodiment, the elimination of *Bacteroides* bacteria in situ involves the use of bacteria or engineered bacteria, in particular engineered *Bacteroides* bacteria, which do not produce MYH6 mimic peptides (in particular mimics of $MYH6_{614-629}$ or $MYH6_{614-628}$ peptides, typically of sequence SEQ ID NO: 10, 16 or 17), more particularly which do not produce $\beta$-$gal_{11-25}$ peptide (typically of sequence SEQ ID NO: 11, 12, 18, 19, 20, 21 or 22).

The invention further includes methods for pre-treatment screening of patient to assess the relevancy to treat a patient based on the presence of specific bacteria in the patient intestinal microbiome that produce MYH6 mimic peptides, the genetic background of the patient with the identification of particular set of HLADQB1*03 alleles and inflammatory myocarditis symptoms of the patient. The invention further includes a pre-treatment screening of effective antibiotics, effective bacteriocins, effective phages, effective recombinant phages, effective packaged phagemids, effective endolysins, effective bacteria or engineered bacteria or any combination thereof against the targeted *Bacteroides* bacteria.

Provided herein are compositions, kits and methods of treating, preventing or curing myocarditis or DCM by killing or reducing the growth of a *Bacteroides* sp.

The invention encompasses the use of a vector that can transfer with high efficiency a nucleic acid, preferably a plasmid, into a bacterial population within the microbiome that allows the expression of an exogenous enzyme that will modify a gene sequence or directly kill the *Bacteroides* bacteria.

Methods of Treatment

The invention encompasses methods of preventing myocarditis, treating myocarditis or DCM, or limiting progression of myocarditis toward DCM in a subject in need thereof, comprising reducing the amount of *Bacteroides* sp. in the subject.

The invention encompasses methods of reducing or eliminating a *Bacteroides* sp. in situ.

In one embodiment, the *Bacteroides* sp. is reduced or eliminated by contacting it with an antibiotic, for example, as described Gil-Cruz et al., Science 366, 881-886 (2019), which is hereby incorporated by reference.

In one embodiment, the *Bacteroides* sp. is reduced or eliminated by a genetic modification that leads to the death or reduction in growth of a *Bacteroides* sp. bacteria, for example, as described in Bikard et al., Cell Host Microbe, Vol. 12, 177-186 (2012) and Bikard et al., Nature Biotechnology Vol. 32 (11) 1146-51 (2014).

In one embodiment, the *Bacteroides* sp. is reduced or eliminated by contacting it with an endolysin, for example, as described in Gerstmans et al., Biochem Soc Trans. 2016 February; 44(1):123-8, which is hereby incorporated by reference.

In one embodiment, the *Bacteroides* sp. is reduced or eliminated by contacting it with a bacteriocin (such as a colicin, a pyocin and/or a tailocin).

In one embodiment, the *Bacteroides* sp. is reduced or eliminated by administering an bacteria or an engineered bacteria, in particular engineered *Bacteroides* sp. which do not produce MYH6 mimic peptides (in particular mimics of $MYH6_{614-629}$ or $MYH6_{614-628}$ peptides, typically of sequence SEQ ID NO: 10, 16 or 17), more particularly which do not produce $\beta$-$gal_{11-25}$ peptide (typically of sequence SEQ ID NO: 11, 12, 18, 19, 20, 21 or 22), and preferably present a competitive advantage over *Bacteroides* sp. to be reduced or eliminated, for example which comprise an heterologous gene or gene circuit required to import and/or metabolize a particular exogenous food source, such as an exogenous sugar.

By "engineered bacteria" is meant herein a bacteria which has been genetically modified, compared to the wild-type strain, in particular to express proteins of interest and/or to stop expressing unwanted proteins.

In a particular embodiment, when said engineered bacteria comprise an heterologous gene or gene circuit required to import and/or metabolize a particular exogenous food source, such as an exogenous sugar, said engineered bacteria are used in combination with said exogenous food source.

In one embodiment, the method comprises contacting the unwanted bacteria with an effective amount of an antibiotic, phage, recombinant phage, packaged phagemid, wild-type or synthetic bacteriocin wild-type or synthetic endolysin or any combination thereof.

In one embodiment, the antibiotic is selected from streptomycin, vancomycin, clindamycin, metronidazole, sulphadoxine, trimethoprim, or any combination of 1, 2, 3, 4, 5 or 6 of these antibiotics.

In one embodiment, the phage, recombinant phage, packaged phagemid encodes a wild-type or synthetic endolysin and/or a wild-type or synthetic bacteriocin In one embodiment, the phage, recombinant phage, packaged phagemid encodes a nuclease selected from the group consisting of CRISPR-Cas and variants, TALENs and variants, zinc finger nuclease (ZFN) and ZFN variants, natural, evolved or engineered meganuclease or recombinase variants.

In one embodiment, the *Bacteroides* is *B. thetaiotaomicron* or *B. faecis*.

In a preferred embodiment, the *Bacteroides* sp. are contacted in situ with a vector that can transfer with high efficiency a nucleic acid into the bacteria to express an exogenous enzyme (such as Cas9 or Cpf1 also known as Cas12a) in the bacteria that results in bacterial cell death or reduced growth.

In a preferred embodiment, the exogenous enzyme can result in a genetic modification where Cas9 nuclease is used to make the desired modification. Thus, the invention contemplates introducing a double strand break in the DNA of the bacterial DNA at a specific sequence, for example with a CRISPR/Cas system, together with non-homologous end joining (NHEJ) or homologous recombination (HR) to generate the desired genetic modification. Preferably, the double strand break is generated in the presence of an editing template comprising homologous region with DNA regions located around the specific sequence located in the bacterial DNA.

The genetic modification can be a point mutation(s), a deletion(s), insertion(s) or any combination thereof. Preferably, the genetic modification is a point mutation, an insertion or a deletion inside a coding sequence leading to a frameshift mutation or a deletion mutation. The genetic modification preferably eliminates, reduces, or increases the expression of a gene. The genetic modification can be in the translated or untranslated regions of a gene. The genetic modification can be in the promoter region of a gene or within any other region involved in gene regulation. In one embodiment, the genetic modification integrates a phage genome or exogenous DNA into the host bacterial chromosome or endogenous plasmid(s). In one embodiment, the genetic modification results in expression of an exogenous protein from an integrated exogenous DNA in the host bacterial chromosome or endogenous plasmid(s). Most preferably, the genetic modification involves either NHEJ or HR endogenous repair mechanism of the host bacteria.

In some embodiments, the genetic modification results in the change in at least 1, 2, 3, 4, 5, 6, 7, 8, 9, 10, 11, 12, 13, 14, 15, 20, 25, 30, 35, 40, 45, 50, 100, 200, 500, etc. amino acids to a different amino acid. In some embodiments, the genetic modification introduces a stop codon. In some embodiments, the genetic modification is outside protein coding sequences, within RNA, or within regulatory sequences.

In some embodiments, the genetic modification is within a β-galactosidase gene, particularly in the coding or non-coding sequence of the β-galactosidase gene, more particularly in the coding or non-coding sequence of the BT-1626 gene, more particularly in the gene encoding the protein of sequence SEQ ID NO: 1, in particular in the nucleic acid sequence SEQ ID NO: 2.

Bacterial Elimination with Antibiotics

Particular bacteria or groups of bacteria such as *Bacteroides* sp. can be eliminated by treatment with antibiotic(s). Thus, the invention encompasses methods of treating a subject with an antibiotic. Preferably, the level of *Bacteroides* sp. is measured before and after the treatment.

In one embodiment, the invention encompasses a method comprising measuring the level of a *Bacteroides* sp., subsequently administering an antibiotic, and measuring the level of the *Bacteroides* sp. after the treatment.

In some embodiments, the antibiotic is streptomycin, vancomycin, clindamycin, or metronidazole, alone or in any possible combination. In some embodiments, the antibiotic is sulphadoxine, trimethoprim, or metronidazole, alone or in any possible combination, such as described in Gil-Cruz et al., Science 366, 881-886 (2019), which is hereby incorporated by reference. In some embodiments, the antibiotic is selected from streptomycin, vancomycin, clindamycin, metronidazole, sulphadoxine, trimethoprim, or any combination of 1, 2, 3, 4, 5 or 6 of these antibiotics.

In some embodiments, the antibiotic is selected from the group consisting of penicillins such as penicillin G, penicillin K, penicillin N, penicillin O, penicillin V, methicillin, benzylpenicillin, nafcillin, oxacillin, cloxacillin, dicloxacillin, ampicillin, amoxicillin, pivampicillin, hetacillin, bacampicillin, metampicillin, talampicillin, epicillin, carbenicillin, ticarcillin, temocillin, mezlocillin, and piperacillin; cephalosporins such as cefacetrile, cefadroxil, cephalexin, cephaloglycin, cefalonium, cefaloridine, cefalotin, cefapirin, cefatrizine, cefazaflur, cefazedone, cefazolin, cefradine, cefroxadine, ceftezole, cefaclor, cefonicid, cefprozil, cefuroxime, cefuzonam, cefmetazole, cefotetan, cefoxitin, loracarbef, cefbuperazone, cefminox, cefotetan, cefoxitin, cefotiam, cefcapene, cefdaloxime, cefdinir, cefditoren, cefetamet, cefixime, cefmenoxime, cefodizime, cefotaxime, cefovecin, cefpimizole, cefpodoxime, cefteram, ceftamere, ceftibuten, ceftiofur, ceftiolene, ceftizoxime, ceftriaxone, cefoperazone, ceftazidime, latamoxef, cefclidine, cefepime, cefluprenam, cefoselis, cefozopran, cefpirome, cefquinome, flomoxef, ceftobiprole, ceftaroline, ceftolozane, cefaloram, cefaparole, cefcanel, cefedrolor, cefempidone, cefetrizole, cefivitril, cefmatilen, cefmepidium, cefoxazole, cefrotil, cefsumide, ceftioxide, cefuracetime, and nitrocefin; polymyxins such as polysporin, neosporin, polymyxin B, and polymyxin E, rifampicins such as rifampicin, rifapentine, and rifaximin; Fidaxomicin; quinolones such as cinoxacin, nalidixic acid, oxolinic acid, piromidic acid, pipemidic acid, rosoxacin, ciprofloxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, temafloxacin, tosufloxacin, clinafloxacin, gatifloxacin, gemifloxacin, moxifloxacin, sitafloxacin, trovafloxacin, prulifloxacin, delafloxacin, nemonoxacin, and zabofloxacin; sulfonamides such as sulfafurazole, sulfacetamide, sulfadiazine, sulfadimidine, sulfafurazole, sulfisomidine, sulfadoxine, sulfamethoxazole, sulfamoxole, sulfanitran, sulfadimethoxine, sulfametho-xypyridazine, sulfametoxydiazine, sulfadoxine, sulfametopyrazine, and terephtyl; macrolides such as azithromycin, clarithromycin, erythromycin, fidaxomicin, telithromycin, carbomycin A, josamycin, kitasamycin, midecamycin, oleandomycin, solithromycin, spiramycin, troleandomycin, tylosin, and roxithromycin; ketolides such as telithromycin, and cethromycin; fluoroketolides such as solithromycin; lincosamides such as lincomycin, clindamycin, and pirlimycin; tetracyclines such as demeclocycline, doxycycline, minocycline, oxytetracycline, and tetracycline; aminoglycosides such as amikacin, dibekacin, gentamicin, kanamycin, neomycin, netilmicin, sisomicin, tobramycin, paromomycin, and streptomycin; ansamycins such as geldanamycin, herbimycin, and rifaximin; carbacephems such as loracarbef; carbapenems such as ertapenem, doripenem, imipenem (or cilastatin), and meropenem; glycopeptides such as teicoplanin, vancomycin, telavancin, dalbavancin, and oritavancin; lincosamides such as clindamycin and lincomycin; lipopeptides such as daptomycin; monobactams such as aztreonam; nitrofurans such as furazolidone, and nitrofurantoin; oxazolidinones such as linezolid, posizolid, radezolid, and torezolid; teixobactin, clofazimine, dapsone, capreomycin, cycloserine, ethambutol, ethionamide, isoniazid, pyrazinamide, rifabutin, arsphenamine, chloramphenicol, fosfomycin, fusidic acid, metronidazole, mupirocin, platensimycin, quinupristin (or dalfopristin), thiamphenicol, tigecycline, tinidazole, trimethoprim, alatrofloxacin, fidaxomicin, nalidixic acid, rifampin, derivatives and combination thereof.

In some embodiments, the *Bacteroides* is resistant to an antibiotic, such as R-lactams, aminoglycosides, erythromycin or tetracycline. In these cases, the gene encoding the resistance gene for that antibiotic within the *Bacteroides* can be modified to make the *Bacteroides* susceptible to the antibiotic. In a further embodiment, the modified *Bacteroides* is then treated with the specific antibiotic.

Measurement of Bacterial Elimination

The elimination of bacteria can be assessed by comparison with and without (control sample) the antibacterial treatment either in vitro or in vivo. Untreated samples can serve as control samples. The comparison is preferably performed by assessing the percentage of bacteria before and after the antibacterial treatment at at least two timepoints and determining a reduced amount of the targeted bacteria at later timepoint, for example, as described in the examples.

Comparison in vitro can be performed by growing the bacteria in solid or liquid culture and determining the percentages or levels of a bacteria over time. The percentages or levels can be determined by routine diagnostic procedures including ELISA, PCR, High Resolution Melting, and nucleic acid sequencing.

Comparison in vivo can be performed by collecting samples (e.g., stool or swab) overtime and determining the percentages or levels of a bacteria over time. The percentages can be determined by routine diagnostic procedures employing immunodetection (e.g. ELISA), nucleic acid amplification (e.g., PCR), High Resolution Melting, and nucleic acid sequencing.

Preferred levels of elimination of bacteria are at least 70%, 80%, 90%, 95%, 97%, 98%, 99%, 99.9%, 99.99%, and 100% of the starting levels of a bacteria.

Enzymes/Systems for Inducing Modifications

In some embodiments, the genetic modification is made with one or more of the following enzymes/systems:

A) Cytosine base editors (CBE) and Adenosine base editors (ABE), for example as described in Rees et al., Nat Rev Genet. 2018 December; 19(12): 770-788, which is hereby incorporated by reference.

So far there are seven types of DNA base editors described:

Cytosine Base Editor (CBE) that convert C:G into T:A (Komor, A et al. Nature 533:420-4. (2016))
Adenine Base Editor (ABE) that convert A:T into G:C (Gaudelli, N. M. et al. Nature 551(7681) 464-471 (2017))
Cytosine Guanine Base Editor (CGBE) that convert C:G into G:C (Chen, L et al. Precise and programmable C:G to G:C base editing in genomic DNA. Biorxiv (2020); Kurt, I et al. Nature Biotechnology 39: 41-46(2021))
Cytosine Adenine Base Editor (CABE) that convert C:G into A:T (Zhao, D et al. Nature Biotechnology 39:35-40 (2021))
Adenine Cytosine Base Editor (ACBE) that convert A:T into C:G (WO2020181180)
Adenine Thymine Base Editor (ATBE) that convert A:T into T:A (WO2020181202)
Thymine Adenine Base Editor (TABE) that convert T:A into A:T (WO2020181193; WO2020181178; WO2020181195)

Base editors differ in the base modification enzymes. CBE rely on ssDNA cytidine deaminase among which: APOBEC1, rAPOBEC1, APOBEC1 mutant or evolved version (evoAPOBEC1), and APOBEC homologs (APOBEC3A (eA3A), Anc689), Cytidine deaminase 1 (CDA1), evoCDA1, FERNY, evoFERNY.

ABE rely on deoxyadenosine deaminase activity of a tandem fusion TadA-TadA* where TadA* is an evolved version of TadA, an *E. coli* tRNA adenosine deaminase enzyme, able to convert adenosine into Inosine on ssDNA. TadA* include TadA-8a-e and TadA-7.10.

Except from base modification enzyme there has been also modifications implemented to base editor to increase editing efficacy, precision and modularity:
  the addition of one or two uracil DNA glycosylase inhibitor domain (UGI) to prevent base excision repair mechanism to revert base edition
  the addition of Mu-GAM that decrease insertion-deletion rate by inhibiting Non-homologous end joining mechanism in the cell (NHEJ)
  the use of nickase active Cas9 (nCas9 D10A) that, by creating nicks on the non-edited strand favors its repair and consequently the fixation of the edited base.
  the use of diverse Cas proteins from for example different organisms, mutants with different PAM motifs or different fidelity or different family (e.g. Cas12a).

Non-limiting examples of DNA-based editor proteins include BE1, BE2, BE3, BE4, BE4-GAM, HF-BE3, Sniper-BE3, Target-AID, Target-AID-NG, ABE, EE-BE3, YE1-BE3, YE2-BE3, YEE-BE3, BE-PLUS, SaBE3, SaBE4, SaBE4-GAM, Sa(KKH)-BE3, VQR-BE3, VRER-BE3, EQR-BE3, xBE3, Cas12a-BE, Ea3A-BE3, A3A-BE3, TAM, CRISPR-X, ABE7.9, ABE7.10, ABE7.10*, xABE, ABESa, VQR-ABE, VRER-ABE, Sa(KKH)-ABE, ABE8e, SpRY-ABE, SpRY-CBE, SpG-CBE4, SpG-ABE, SpRY-CBE4, SpCas9-NG-ABE, SpCas9-NG-CBE4, enAsBE1.1, enAsBE1.2, enAsBE1.3, enAsBE1.4, AsBE1.1, AsBE1.4, CRISPR-Abest, CRISPR-Cbest, eA3A-BE3, AncBE4.

Cytosine Guanine Base Editors (CGBE) consist of a nickase CRISPR fused to:
a. A cytosine deaminase (rAPOBEC) and base excision repair proteins (e.g. rXRCC1). (Chen, L et al. Precise and programmable C:G to G:C base editing in genomic DNA. Biorxiv (2020); Chen et al. Programmable C:G to G:C genome editing with CRISPR-Cas9-directed base excision repair proteins. Nature Communications 12:1384 (2021)).
b. A rat APOBEC1 variant (R33A) protein and an *E. coli*-derived uracil DNA N-glycosylase (eUNG) (Kurt, I et al. Nature Biotechnology 39: 41-46(2021)).

Cytosine Adenine Base Editors (CABE) consist of a Cas9 nickase, a cytidine deaminase (e.g. AID), and a uracil-DNA glycosylase (Ung) (Zhao, D et al. Nature Biotechnology 39:35-40(2021)).

ACBE include a nucleic acid programmable DNA-binding protein and an adenine oxidase (WO2020181180).

ATBE consist of a Cas9 nickase and one or more adenosine deaminase or an oxidase domain (WO2020181202).

TABE consist of a Cas9 nickase and an adenosine methyltransferase, a thymine alkyltransferase, or an adenosine deaminase domain (WO2020181193; WO2020181178; WO2020181195).

Base editor molecules can also consist of two or more of the above listed editor enzymes fused to a Cas protein (e.g. combination of an ABE and CBE). These biomolecules are named dual base editors and enable the editing of two different bases (Grunewald, J et al. Nature Biotechnology 38:861-864(2020); Li, C et al. Nature Biotechnology 38:875-882(2020)).

B) Prime editors (PE), as described in Anzalone et al. Nature 576:149-157 (2019) which is hereby incorporated by reference, consist of a nCas9 fused to a reverse transcriptase used in combination with a prime editing RNA (pegRNA; a guide RNA that includes a template region for reverse transcription).

Prime Editing allows introduction of insertions, deletions (indels), and 12 base-to-base conversions. Prime editing relies on the ability of a reverse transcriptase (RT), fused to a Cas nickase variant, to convert RNA sequence brought by a prime editing guide RNA (pegRNA) into DNA at the nick site generated by the Cas protein. The DNA flap generated from this process is then included or not in the targeted DNA sequence.

Prime editing systems include:
a Cas nickase variant such as Cas9-H840A fused to a reverse transcriptase domain such as M-MLV RT or its mutant version (M-MLV RT(D200N), M-MLV RT(D200N/L603W), M-MLV RT(D200N/L603W/T330P/T306K/W313F)
a prime editing guide RNA (pegRNA)

To favor editing, the prime editing system can include the expression of an additional sgRNA targeting the Cas nickase activity towards the non-edited DNA strand ideally only after the resolution of the edited strand flap by designing the sgRNA to anneal with the edited strand but not with the original strand.

Non-limiting examples of prime editing systems include PE1, PE1-M1, PE1-M2, PE1-M3, PE1-M6, PE1-M15, PE1-M3inv, PE2, PE3, PE3b.

C) Cas9 Retron preclSe Parallel Editing via homologY ('CRISPEY'), a retron RNA fused to the sgRNA and expressed together with Cas9 and the retron proteins including at least the reverse transcriptase (Sharon, E. et al. Cell 175, 544-557.e16 (2018)).

D) The SCRIBE strategy: a retron system expressed in combination with a recombinase promoting the recombination of single stranded DNA, also known as single stranded annealing proteins (SSAPs) (Farzadfard, F. & Lu, T. K. Science 346, 1256272 (2014)). Such recombinases include but are not limited to phage recombinases such as lambda red, recET, Sak, Sak4, and newly described SSAPs described in Wannier, T. M. et al. (Improved bacterial recombineering by parallelized protein discovery. Biorxiv 2020.01.14.906594 (2020) doi:10.1101/2020.01.14.906594), which is hereby incorporated by reference.

E) The targetron system based on group II introns described in Karberg, M. et al. *Nat Biotechnol* 19, 1162-7 (2001), which is hereby incorporated by reference, and which has been adapted to many bacterial species.

F) Other retron based gene targeting approaches are described in Simon et al. *Nucleic Acids Res* 47, 11007-11019 (2019) which is hereby incorporated by reference.

G) CRISPR-Cas. The CRISPR system contains two distinct elements, i.e. i) an endonuclease, in this case the CRISPR associated nuclease (Cas or "CRISPR associated protein") and ii) a guide RNA. Depending on the type of CRISPR system, the guide RNA may be in the form of a chimeric RNA which consists of the combination of a CRISPR (crRNA) bacterial RNA and a tracrRNA (trans-activating RNA CRISPR)[16]. The guide RNA combines the targeting specificity of the crRNA corresponding to the "spacing sequences" that serve as guides to the Cas proteins, and the conformational properties of the tracrRNA in a single transcript. When the guide RNA and the Cas protein are expressed simultaneously in the cell, the target genomic sequence can be permanently interrupted (and causing disappearance of the targeted and surrounding sequences and/or cell death, depending on the location) or modified. The modification may be guided by a repair matrix.

The CRISPR system includes two main classes depending on the nuclease mechanism of action:
Class 1 is made of multi-subunit effector complexes and includes type I, III and IV
Class 2 is made of single-unit effector modules, like Cas9 nuclease, and includes type II (II-A, II-B, II-C, II-C variant), V (V-A,V-B,V-C,V-D,V-E,V-U1,V-U2,V-U3, V-U4,V-U5) and VI (VI-A,VI-B1,VI-B2,VI-C,VI-D)

The sequence of interest according to the present invention comprises a nucleic acid sequence encoding Cas protein. A variety of CRISPR enzymes are available for use as a sequence of interest on the plasmid according to the present invention. In some embodiments, the CRISPR enzyme is a Type II CRISPR enzyme, a Type II-A or Type II-B CRISPR enzyme. In another embodiment, the CRISPR enzyme is a Type I CRISPR enzyme or a Type III CRISPR enzyme. In some embodiments, the CRISPR enzyme catalyzes DNA modification. In some other embodiments, the CRISPR enzyme catalyzes RNA modification. For instance, Cas13-deaminase fusions have been used for RNA base editing thus modifying RNA (David BT Cox et al, Science, 358 (6366) p. 1019-1027, 2017 Nov. 24). In one embodiment, the CRISPR enzymes may be coupled to a guide RNA or single guide RNA (sgRNA). In certain embodiments, the guide RNA or sgRNA targets a gene selected from the group consisting of an antibiotic resistance gene, virulence protein or factor gene, toxin protein or factor gene, a bacterial receptor gene, a membrane protein gene, a structural protein gene, a secreted protein gene, a gene expressing resistance to a drug in general and a gene causing a deleterious effect to the host. Preferably, the CRISPR enzyme makes a double strand break. In some embodiments, the CRISPR enzyme makes a single strand break or nicks. In some embodiments, the CRISPR enzyme does not make any break in the DNA or RNA. In one embodiment, a Cas13-deaminase fusion is used to base edit an RNA.

The sequence of interest may comprise a nucleic acid sequence encoding a guide RNA or sgRNA to guide the Cas protein endogenous to the targeted bacteria, alone or in combination with a Cas protein and/or a guide RNA encoded by the payload.

Non-limiting examples of Cas proteins as part of a multi-subunit effector or as a single-unit effector include Cas1, Cas1B, Cas2, Cas3, Cas4, Cas5, Cas6, Cas7, Cas8, Cas9 (also known as Csn1 and Csx12), Cas10, Cas11 (SS), Cas12a (Cpf1), Cas12b (C2c1), Cas12c (C2c3), Cas12d (CasY), Cas12e (CasX), C2c4, C2c8, C2c5, C2c10, C2c9, Cas13a (C2c2), Cas13b (C2c6), Cas13c (C2c7), Cas13d, Csa5, Csc1, Csc2, Cse1, Cse2, Csy1, Csy2, Csy3, Csf1, Csf2, Csf3, Csf4, Csm1, Csm2, Csm3, Csm4, Csm5, Csm6, Cmr1, Cmr3, Cmr4, Cmr5, Cmr6, Csn2, Csb1, Csb2, Csb3, Csx17, Csx14, Csx10, Csx16, CsaX, Csx13, Csx1, Csx15, SdCpf1, CmtCpf1, TsCpf1, CmaCpf1, PcCpf1, ErCpf1, FbCpf1, UbcCpf1, AsCpf1, LbCpf1, homologues thereof, orthologues thereof, variants thereof, or modified versions thereof. In some embodiments, the CRISPR enzyme cleaves both strands of the target nucleic acid at the Protospacer Adjacent Motif (PAM) site.

In various embodiments, the invention encompasses fusion proteins comprising a Cas9 (e.g., a Cas9 nickase) domain and a deaminase domain. In some embodiments, the fusion protein comprises Cas9 and a cytosine deaminase enzyme, such as APOBEC enzymes, or adenosine deaminase enzymes, such as ADAT enzymes, for example as disclosed in U.S. Patent Publ. 2015/0166980, which is hereby incorporated by reference. In one embodiment, the deaminase is an ACF1/ASE deaminase.

In various embodiments, the APOBEC deaminase is selected from the group consisting of APOBEC1 deaminase, APOBEC2 deaminase, APOBEC3A deaminase, APOBEC3B deaminase, APOBEC3C deaminase, APOBEC3D deaminase, APOBEC3F deaminase, APOBEC3G deaminase, and APOBEC3H deaminase. In various embodiments, the fusion protein comprises a Cas9 domain, a cytosine deaminase domain, and a uracil glycosylase inhibitor (UGI) domain.

In one embodiment, the deaminase is an adenosine deaminase that deaminate adenosine in DNA, for example as disclosed in U.S. Pat. No. 10,113,163, which is hereby incorporated by reference. In some embodiments, the fusion proteins further comprise a nuclear localization sequence (NLS), and/or an inhibitor of base repair, such as, a nuclease dead inosine specific nuclease (dISN), for example as disclosed in U.S. Pat. No. 10,113,163. In various embodiments, the invention encompasses fusion proteins comprising a catalytically impaired Cas9 endonuclease fused to an engineered reverse transcriptase, programmed with a prime editing guide RNA (pegRNA) that both specifies the target site and encodes the desired edit, for example as described in Anzalone et al., Nature, Vol. 576, pages 149-157 (2019), which is hereby incorporated by reference.

In a particular embodiment, the CRISPR enzyme is any Cas9 protein, for instance any naturally-occurring bacterial Cas9 as well as any variants, homologs or orthologs thereof.

By "Cas9" is meant a protein Cas9 (also called Csn1 or Csx12) or a functional protein, peptide or polypeptide fragment thereof, i.e. capable of interacting with the guide RNA(s) and of exerting the enzymatic activity (nuclease) which allows it to perform the double-strand cleavage of the DNA of the target genome. "Cas9" can thus denote a modified protein, for example truncated to remove domains of the protein that are not essential for the predefined functions of the protein, in particular the domains that are not necessary for interaction with the gRNA (s). In some embodiments, the CAS9 is a dCas9 (dead-Cas9) or nCas9 (nickase Cas9) lacking double stranded DNA cleavage activity.

The sequence encoding Cas9 (the entire protein or a fragment thereof) as used in the context of the invention can be obtained from any known Cas9 protein (Fonfara et al., Nucleic Acids Research 42, 2577-2590 (2014); Koonin et al., Current Opinion in Microbiology 37, 67-78 (2017)). Examples of Cas9 proteins useful in the present invention include, but are not limited to, Cas9 proteins of Streptococcus pyogenes (SpCas9), Streptococcus thermophiles (St1Cas9, St3Cas9), Streptococcus mutans, Staphylococcus aureus (SaCas9), Campylobacter jejuni (CjCas9), Francisella novicida (FnCas9) and Neisseria meningitides (NmCas9).

The sequence encoding Cpf1 (Cas12a) (the entire protein or a fragment thereof) as used in the context of the invention can be obtained from any known Cpf1 (Cas12a) protein (Koonin et al., Current Opinion in Microbiology 37, 67-78 (2017)). Examples of Cpf1 (Cas12a) proteins useful in the present invention include, but are not limited to, Cpf1 (Cas12a) proteins of Acidaminococcus sp, Lachnospiraceae bacteriu and Francisella novicida.

The sequence encoding Cas13a (the entire protein or a fragment thereof) as used in the context of the invention can be obtained from any known Cas13a (C2c2) protein (Abudayyeh et al., Nature 550, 280 (2017)). Examples of Cas13a (C2c2) proteins useful in the present invention include, but are not limited to, Cas13a (C2c2) proteins of Leptotrichia wadei (LwaCas13a).

The sequence encoding Cas13d (the entire protein or a fragment thereof) as used in the context of the invention can be obtained from any known Cas13d protein (Yan et al. (2018) Mol Cell 70(2):327-339). Examples of Cas13d proteins useful in the present invention include, but are not limited to, Cas13d proteins of Eubacterium siraeum and Ruminococcus sp.

In some embodiments, other programmable nucleases can be used. These include an engineered TALEN (Transcription Activator-Like Effector Nuclease) and variants, engineered zinc finger nuclease (ZFN) variants, natural, evolved or engineered meganuclease or recombinase variants, and any combination or hybrids of programmable nucleases. Thus, the programmable nucleases provided herein may be used to selectively modify a Bacteroides sp. DNA encoding a gene of interest.

In some embodiments, the genetic modification is made at the RNA level. RNA base editing is based on the same principle as DNA base editing: an enzyme catalyzing the conversion of a RNA base into another must be brought close to the target base to perform its conversion locally. In one embodiment, the enzyme used for RNA editing is an adenosine deaminase from ADAR family that converts Adenosine into Inosine in dsRNA structure. Several seminal studies used this specificity for dsRNA and fused the ADAR deaminase domain (ADAR$_{DD}$) to an antisense oligo in order to program local RNA base editing. More recently the ability of some CRISPR-Cas systems to bind RNA molecules was repurposed into RNA editing. Using catalytically dead Cas13b enzyme (dPspCas13b) fused to a hyperactive mutant of ADAR2 deaminase domain (ADAR2$_{DD}$-E488Q for REPAIRv1 and ADAR2$_{DD}$-E488Q-T375G for REPAIRv2) Cox et al improved specificity and efficiency compare to previous RNA editing strategies.

Non-limiting examples of RNA based editor proteins include REPAIRv1, REPAIRv2.

Vectors for Inducing Modifications

In various embodiments, one or more of the following vectors can be used to eliminate or reduce deleterious Bacteroides sp., in particular to introduce the exogenous enzyme that results in a genetic modification or to introduce an endolysin:
  engineered phages,
  engineered bacteria,
  plasmid (eg, a conjugative plasmid capable of transfer into a host cell), phage, phagemid or prophage.
  Each vector may be as described above, eg, a phage capable of infecting a host cell or conjugative plasmid capable of introduction into a host cell, which can be introduced either by a phage particle (engineered or wild-type phage) via injection or by a donor bacteria via conjugation. In an example, the vectors are in combination with an antibiotic agent (eg, a beta-lactam antibiotic) and/or with any other agent.

A bacteriophage for modifying a naturally occurring bacteria in situ comprising a nucleic acid encoding a gene editing enzyme/system for transformation of a target bacteria in a mixed bacterial population wherein said gene editing enzyme/system modifies the genome of said target bacteria, but does not lead to the death of the target bacteria.

The invention encompasses the use of these vectors wherein the gene editing enzyme/system targets a gene within the target bacteria encoding a protein which is directly or indirectly responsible for a disease or disorder, in particular myocarditis or DCM. In a particular embodiment, the gene editing enzyme/system targets a β-galactosidase gene.

Bacterial viruses (also called bacteriophages or phages) are small viruses displaying the ability to infect and kill bacteria while they do not affect cells from other organisms. Initially described almost a century ago by William Twort, and independently discovered shortly thereafter by Félix d'Herelle, more than 6000 different bacterial viruses have been discovered so far and described morphologically. The vast majority of these viruses are tailed while a small proportion, are polyhedral, filamentous or pleomorphic. They may be classified according to their morphology, their genetic content (DNA vs. RNA), their specific host, the place where they live (marine virus vs. other habitats), and their life cycle. As intracellular parasites of bacterial cells, phages display different life cycles within the bacterial host: lytic, lysogenic, pseudo-lysogenic, and chronic infection. Lytic phages, once their DNA injected into their host, replicate their own genome and produce new viral particles at the expense of the host. Indeed, they cause lysis of the host bacterial cell as a normal part of the final stage of their life cycles to liberate viral particles. Temperate phages can either replicate by means of the lytic life cycle and cause lysis of the host bacterium, or they can incorporate their DNA into the host bacterial DNA and become non-infectious prophages (lysogenic cycle). In some embodiments, lytic phages are used.

Unlike classical chemically-based antibiotics that are active against a broad spectrum of bacterial species, a bacteriophage can infect and kill only a small number of different closely-related bacteria.

The use of packaged phagemids) allows to have a defined and controlled way of killing the host. Example of packaged phagemids encoding CRISPR-Cas9 or toxins have shown promising results in killing targeted bacterial population (Bikard et al., 2012, *Cell Host & Microbe* 12, 177-186; Jiang et al., 2013, *Nat Biotechnol* 31, 233-239; Krom et al., 2015, *Nano Letters* 15, 4808-4813; Bikard et al, 2014, *Nat Biotech* 11, Vol. 32, Citorik, R et al, 2014, *Nat Biotech* 11, Vol. 32).

Sequence of Interest Under the Control of the Promoter

The vector can comprise a sequence of interest under the control of a promoter.

In one embodiment, the sequence of interest is a programmable nuclease circuit to be delivered to the targeted bacteria. This programmable nuclease circuit may be able to mediate in vivo sequence-specific elimination of bacteria that contain a target gene of interest. Some embodiments of the present disclosure relate to engineered variants of the Type II CRISPR-Cas (Clustered Regularly Interspaced Short Palindromic Repeats-CRISPR-associated) system of *Streptococcus pyogenes*. Other programmable nucleases that can be used include other CRISPR-Cas systems, engineered TALEN (Transcription Activator-Like Effector Nuclease) variants, engineered zinc finger nuclease (ZFN) variants, natural, evolved or engineered meganuclease or recombinase variants, and any combination or hybrids of programmable nucleases.

Other sequences of interest, preferably programmable, can be added to the payload so as to be delivered to targeted bacteria.

Preferably, the sequence of interest circuit added to the payload leads to bacteria death. The sequence of interest may comprise proteins and enzymes achieving a useful function such as modifying the metabolism of the bacteria, the composition of its environment or affecting the host.

In a particular embodiment, the nucleic acid sequence of interest is selected from the group consisting of a Cas nuclease, a type I nuclease, a type II nuclease, a type V nuclease, a Cas9 nuclease, a Cpf1 nuclease, a Cas3 nuclease, a Cms1 nuclease, a MAD nuclease, a guide RNA, a single guide RNA (sgRNA), a CRISPR locus, a gene expressing an enzyme such as a nuclease or a kinase, a TALEN, a ZFN, a meganuclease, a recombinase, a bacterial receptor, a membrane protein, a structural protein, a secreted protein, a gene expressing resistance to an antibiotic or to a drug in general, a gene expressing a toxic protein or a toxic factor and a gene expressing a virulence protein or a virulence factor, a bacterial secretory protein or transporter, a bacterial pore or any of their combination. These proteins can also be modified or engineered to include extra features, like the addition or removal of a function (e.g. dCas9), the addition of a secretion signal to a protein not normally secreted, the addition of an exogenous peptide in a loop as non-limiting examples.

Targeted Bacteria

The *Bacteroides* targeted by a composition of the invention can be present in vivo, in a mammalian organism, or in vitro, for example in liquid or solid culture.

A microbiome may comprise a variety of endogenous *Bacteroides* species, any of which may be targeted in accordance with the present disclosure. In some embodiments, the species of targeted *Bacteroides* bacterial cells may depend on the type of bacteriophages being used for preparing the bacterial virus particles. For example, some bacteriophages exhibit tropism for, or preferentially target, specific host species of bacteria. Other bacteriophages do not exhibit such tropism and may be used to target a number of different genus and/or species of endogenous bacterial cells.

Examples of *Bacteroides* species include, without limitation, *B. acidifaciens, B. barnesiaes, B. caccae, B. caecicola, B. caecigallinarum, B. cellulosilyticus, B. cellulosolvens, B. clarus, B. coagulans, B. coprocola, B. coprophilus, B. coprosuis, B. distasonis, B. eggerthii, B. gracilis, B. faecichinchillae, B. faecis, B. finegoldii, B. fluxus, B. fragilis, B. galacturonicus, B. gallinaceumi, B. gallinarum, B. goldsteinii, B. graminisolvens, B. helcogene, B. intestinalis, B. luti, B. massiliensis, B. melaninogenicus, B. nordii, B. oleiciplenus, B. oris, B. ovatus, B. paurosaccharolyticus, B. plebeius, B. polypragmatus, B. propionicifaciens, B. putredinis, B. pyogenes, B. reticulotermitis, B. rodentium, B. salanitronis, B. salyersiae, B. sartorii, B. sedimenti, B. stercoris, B. suis, B. tectus, B. thetaiotaomicron, B. uniformis, B. vulgatus, B. xylanisolvens,* and *B. xylanolyticus.*

Thus, bacterial virus particles may target (e.g., specifically target) a bacterial cell from any one or more of the foregoing species of bacteria to specifically deliver the plasmid according to the invention.

In preferred embodiments, the targeted bacterial cells are, without limitation, *Bacteroides* faecis, *Bacteroides* thetaiotaomicron, *Bacteroides fragilis, Bacteroides distasonis, Bacteroides vulgatus,* and *Bacteroides fragilis.*

In particular embodiments, the targeted bacterial cells are, without limitation, *Bacteroides* sp. bacterial which produce MYH6 mimic peptides (in particular mimics of MYH6$_{614-629}$ or MYH6$_{614-628}$ peptides, typically of sequence SEQ ID NO: 10, 16 or 17), more particularly which produce β-galactosidase (typically of sequence SEQ ID NO: 1), more particularly which produce β-gal$_{11-25}$ peptide (typically of sequence SEQ ID NO: 11, 12, 18, 19, 20, 21 or 22).

Bacterial Viruses

The bacterial virus particles are prepared from bacterial virus. The bacterial viruses can be chosen in order to be able to introduce the plasmid into the targeted bacteria.

Bacterial viruses are preferably bacteriophages. Bacteriophages are obligate intracellular parasites that multiply inside bacteria by co-opting some or all of the host biosynthetic machinery. Phage genomes come in a variety of sizes and shapes (e.g., linear or circular). Most phages range in size from 24-200 nm in diameter. Phages contain nucleic acid (i.e., genome) and proteins, and may be enveloped by a lipid membrane. Depending upon the phage, the nucleic acid genome can be either DNA or RNA, and can exist in either circular or linear forms. The size of the phage genome varies depending upon the phage. The simplest phages have genomes that are only a few thousand nucleotides in size, while the more complex phages may contain more than 100,000 nucleotides in their genome, and in rare instances more than 1,000,000. The number and amount of individual types of protein in phage particles will vary depending upon the phage.

A non-exhaustive listing of known *Bacteroides*-specific bacteria viruses is presented in the following paragraphs. Synonyms and spelling variants are indicated in parentheses. Homonyms are repeated as often as they occur (e.g., D, D, d). Unnamed phages are indicated by "NN" beside their genus and their numbers are given in parentheses.

Bacteria of the genus *Bacteroides* can be infected by the following phages: crAss-phage, ad 12, Baf-44, Baf-48B, Baf-64, Bf-I, Bf-52, B40-8, FI, βI, φAI, φBrOI, φBrO2, 11, 67.1, 67.3, 68.1, mt-*Bacteroides* (3), Bf42, Bf71, HN-Bdellovibrio (1) and BF-41.

In some embodiment the vectors disclosed herein may be used in combination with prebiotics. Prebiotics include, but are not limited to, amino acids, biotin, fructo-oligosaccharide, galacto-oligosaccharides, hemicelluloses (e.g., arabinoxylan, xylan, xyloglucan, and glucomannan), inulin, chitin, lactulose, mannan oligosaccharides, oligofructose-enriched inulin, gums (e.g., guar gum, gum arabic and carrageenan), oligofructose, oligodextrose, tagatose, resistant maltodextrins (e.g., resistant starch), trans-galactooligosaccharide, pectins (e.g., xylogalacturonan, citrus pectin, apple pectin, and rhamnogalacturonan-1), dietary fibers (e.g., soy fiber, sugarbeet fiber, pea fiber, corn bran, and oat fiber) and xylooligosaccharides.

In other embodiment, the vectors, antibiotics, bacteriocins and/or endolysins disclosed herein may be used in combination with bacteria and/or engineered bacteria and/or probiotics. Probiotics include, but are not limited to lactobacilli, bifidobacteria, streptococci, enterococci, propionibacteria, saccharomycetes, lactobacilli, bifidobacteria, or proteobacteria.

In one embodiment, said bacteria and/or engineered bacteria, in particular engineered *Bacteroides* sp. and/or probiotics do not produce MYH6 mimic peptides (in particular mimics of MYH6$_{614-629}$ or MYH6$_{614-628}$ peptides, typically of sequence SEQ ID NO: 10, 16 or 17), more particularly do not produce β-gal$_{11-25}$ peptide (typically of sequence SEQ ID NO: 11, 12, 18, 19, 20, 21 or 22), and preferably present a competitive advantage over *Bacteroides* sp. to be reduced or eliminated.

In a particular embodiment, said probiotic is an engineered probiotic.

In a particular embodiment, said engineered bacteria and/or probiotics further comprise an heterologous gene or gene circuit required to import and/or metabolize a particular exogenous food source, such as an exogenous sugar.

In a particular embodiment, said engineered bacteria and/or probiotics may further be engineered to be insensitive to the vectors, phages, antibiotics, bacteriocins and/or endolysins used herein.

In a particular embodiment, the vector, phage, antibiotic, bacteriocin and/or endolysin disclosed herein is used in combination with (i) an engineered bacteria and/or probiotic further comprising an heterologous gene or gene circuit required to import and/or metabolize a particular exogenous food source and (ii) said exogenous food source.

The combined use of the vector disclosed herein and the herein disclosed engineered bacteria and/or probiotic and the corresponding exogenous food source typically enables said engineered bacteria and/or probiotic to fill the niche left empty by the bacteria, in particular the *Bacteroides* bacteria killed by the use of the vector of the invention.

Said bacteria and/or engineered bacteria and/or probiotic can typically be administered before, simultaneously with or after said vector, phage, antibiotic, bacteriocin and/or endolysin.

Screening Methods

The invention encompasses methods for screening for genetic modifications in *Bacteroides* sp. In one embodiment, the method comprises administering a vector designed to genetically modify at least one base of a DNA of interest in a gene of a *Bacteroides* sp., to a subject, subsequently collecting a bacterial sample from the subject, quantitating the level of bacteria containing a genetic modification in said at least one base of a DNA of interest in said bacterial sample. The genetic modification can be the insertion of an exogenous DNA, for example, encoding an endolysin. The method can further comprise quantitating the level of bacteria not containing a genetic modification in said at least one base of a DNA of interest.

In one embodiment, the proportion of *Bacteroides* sp. modified vs non-modified bacteria is quantified. Preferred percentages of bacteria with the genetic modification are at least 20%, 30%, 40%, 50%, 60%, 70%, 80%, 90%, 95%, 97%, 98%, 99%, 99.9%, 99.99%, and 100%.

In one embodiment, the number of non-modified endogenous bacteria is quantified prior to administering a vector. The patient can also be pre-screened to determine the genetic signature of the strains the patient carries. This will allow selection of an appropriate capsid to deliver the therapeutic payload based on the genetic signature of the strains the patient carries.

In preferred embodiments, the vector is in a pharmaceutical or veterinary composition. Preferably the vector is a bacteriophage.

The vector can be administered to the subject by any administration technique known in the art, depending on the vector and the target bacteria's expected location in or on the subject.

The bacterial sample can be collected by any means known in the art, such as biopsy, blood draw, urine sample, stool sample, or oral/nasal swab, etc.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

The invention encompasses methods for determining the efficiency of a vector at inducing genetic mutations in situ. In one embodiment, the method comprises administering a vector designed to genetically modify at least one base of a DNA of interest in a gene of a naturally occurring bacteria, to a subject, subsequently collecting a bacterial sample from the subject, quantitating the level of bacteria containing a genetic modification in said at least one base of a DNA of interest and quantitating the level of bacteria not containing a genetic modification in said at least one base of a DNA of interest in said bacterial sample.

In preferred embodiments, the vector is in a pharmaceutical or veterinary composition. Preferably the vector is a bacteriophage.

The vector can be administered to the subject by any administration technique known in the art, depending on the vector and the target bacteria's expected location in or on the subject.

The bacterial sample can be collected by any means known in the art, such as biopsy, blood draw, urine sample, stool sample, or oral/nasal swab, etc.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

The invention encompasses methods for determining the effect of a genetic mutation on bacterial growth. In one embodiment, the method comprises administering a vector designed to genetically modify at least one base of a DNA of interest in a gene of a *Bacteroides* sp., to a subject, subsequently collecting at least two sequential bacterial samples from the subject, quantitating the level of bacteria containing a genetic modification in said at least one base of a DNA of interest and quantitating the level of bacteria not containing a genetic modification in said at least one base of a DNA of interest in said bacterial samples.

In preferred embodiments, the vector is in a pharmaceutical or veterinary composition. Preferably the vector is a bacteriophage.

The vector can be administered to the subject by any administration technique known in the art, depending on the vector and the target bacteria's expected location in or on the subject.

The bacterial samples can be collected by any means known in the art, such as biopsy, blood draw, urine sample, stool sample, or oral/nasal swab, etc. The samples can be collected at any sequential time points. Preferably, the time between these collections is at least 3, 6, 12, 24, 48, 72, 96 hours or 7, 14, 30, 60, 120, or 365 days.

The level of bacteria containing or not containing a genetic modification in a base of a DNA of interest can be determined by any technique known to the skilled artisan, such as routine diagnostic procedures including ELISA, PCR, High Resolution Melting, and nucleic acid sequencing.

All of the screening methods of the invention can use any of the vectors and enzymes/systems of the invention to screen for any of the genetic modification of the invention.

All of the screening methods of the invention can further include a step of comparing the level of bacteria containing a genetic modification in a base of a DNA of interest with the level of bacteria not containing a genetic modification the base of a DNA of interest in a bacterial sample.

All of the screening methods of the invention can further include a step of contacting the vector with bacteria in liquid or solid culture and quantitating the level of bacteria containing a genetic modification in said at least one base of a DNA of interest in said bacterial sample. The method can further comprise quantitating the level of bacteria not containing a genetic modification in said at least one base of a DNA of interest.

In one embodiment, the method comprises providing a vector designed to genetically modify at least one base of a DNA of interest in a gene of a *Bacteroides* sp. The method can further comprise contacting the vector with a *Bacteroides* sp. in liquid or solid culture and quantitating the level of *Bacteroides* sp. containing a genetic modification in said at least one base of a DNA of interest in said bacterial sample. The method can further comprise quantitating the level of bacteria not containing a genetic modification in said at least one base of a DNA of interest. The levels of bacteria containing a genetic modification in a base of a DNA of interest can be compared with the level of bacteria not containing a genetic modification the base of a DNA of interest over time in the culture. Preferably, the time between these comparisons is at least 1, 2, 3, 4, 5, 6, 12, 24, 48, 72, or 96 hours.

The invention encompasses methods for determining the efficiency of a bacteria, engineered bacteria, antibiotic, bacteriocin or endolysin at reducing or killing *Bacteroides* sp. in situ. In one embodiment, the method comprises providing a bacteria, engineered bacteria, antibiotic, bacteriocin or endolysin, contacting the bacteria, engineered bacteria, antibiotic, bacteriocin or endolysin with a *Bacteroides* sp. in situ, and quantitating the level of *Bacteroides* sp. killed or reduced by the bacteria, engineered bacteria, antibiotic, bacteriocin or endolysin. In some embodiments, the endolysin or bacteriocin is encoded by a vector, such as a bacteriophage. The method can further comprise quantitating the level of *Bacteroides* not killed or reduced by the bacteria, engineered bacteria, antibiotic, bacteriocin or endolysin. The levels of bacteria can be compared over time. Preferably, the time between these comparisons is at least 1, 2, 3, 4, 5, 6, 12, 24, 48, 72, or 96 hours.

Pharmaceutical and Veterinary Compositions and In situ Administration Methods

The invention encompasses pharmaceutical and veterinary compositions comprising the vectors, bacteria, engineered bacteria, antibiotics, bacteriocins and/or endolysins of the invention.

The invention encompasses a pharmaceutical agent which reduces the amount of *Bacteroides* sp. in a subject.

The invention encompasses in situ administration of the pharmaceutical or veterinary composition to the bacteria in a subject. Any method known to the skilled artisan can be used to contact the composition with the bacterial target in situ.

In one embodiment, the composition comprises an effective amount of an antibiotic, phage, recombinant phage, packaged phagemid, bacteria, engineered bacteria, bacteriocin or endolysin.

In one embodiment, the antibiotic is selected from streptomycin, vancomycin, clindamycin, metronidazole, sulphadoxine, trimethoprim, or any combination of 1, 2, 3, 4, 5 or 6 of these antibiotics.

In one embodiment, the phage, recombinant phage, packaged phagemid encodes an endolysin or a bacteriocin.

In one embodiment, the phage, recombinant phage, packaged phagemid encodes a nuclease selected from CRISPR-Cas, TALENs and variants, zinc finger nuclease (ZFN) and ZFN variants, natural, evolved or engineered meganuclease or recombinase variants.

In one embodiment, the *Bacteroides* is *B. thetaiotaomicron* or *B. faecis*.

The pharmaceutical or veterinary composition according to the invention may further comprise a pharmaceutically acceptable vehicle. A solid pharmaceutically acceptable vehicle may include one or more substances which may also act as flavoring agents, lubricants, solubilizers, suspending agents, dyes, fillers, glidants, compression aids, inert binders, sweeteners, preservatives, dyes, coatings, or tablet-disintegrating agents. Suitable solid vehicles include, for example calcium phosphate, magnesium stearate, talc, sugars, lactose, dextrin, starch, gelatin, cellulose, polyvinylpyrrolidone, low melting waxes and ion exchange resins.

The pharmaceutical or veterinary composition may be prepared as a sterile solid composition that may be suspended at the time of administration using sterile water, saline, or other appropriate sterile injectable medium. The pharmaceutical or veterinary compositions of the invention may be administered orally in the form of a sterile solution or suspension containing other solutes or suspending agents (for example, enough saline or glucose to make the solution isotonic), bile salts, acacia, gelatin, sorbitan monooleate, polysorbate 80 (oleate esters of sorbitol and its anhydrides copolymerized with ethylene oxide) and the like. The particles according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for enteral administration include sterile solutions, emulsions, and suspensions.

The bacterial virus particles according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid vehicles for oral and enteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the vehicle can also be an oily ester such as ethyl oleate and isopropyl myristate. Sterile liquid vehicles are useful in sterile liquid form compositions for enteral administration. The liquid vehicle for pressurized compositions can be a halogenated hydrocarbon or other pharmaceutically acceptable propellant.

In some embodiments, the invention encompasses pharmaceutical or veterinary composition formulated for delayed or gradual enteric release. In preferred embodiments, formulations or pharmaceutical preparations of the invention are formulated for delivery of the vector into the distal small bowel and/or the colon. The formulation can allow the vector to pass through stomach acid and pancreatic enzymes and bile, and reach undamaged to be viable in the distal small bowel and colon.

In some embodiments, the pharmaceutical or veterinary composition is micro-encapsulated, formed into tablets and/or placed into capsules, preferably enteric-coated capsules.

In some embodiments, the pharmaceutical or veterinary compositions are formulated for delayed or gradual enteric release, using cellulose acetate (CA) and polyethylene glycol (PEG). In some embodiments, the pharmaceutical or veterinary compositions are formulated for delayed or gradual enteric release using a hydroxypropylmethylcellulose (HPMC), a microcrystalline cellulose (MCC) and magnesium stearate. the pharmaceutical or veterinary compositions are formulated for delayed or gradual enteric release using e.g., a poly(meth)acrylate, e.g. a methacrylic acid copolymer B, a methyl methacrylate and/or a methacrylic acid ester, or a polyvinylpyrrolidone (PVP).

In some embodiments, the pharmaceutical or veterinary compositions are formulated for delayed or gradual enteric release using a release-retarding matrix material such as: an acrylic polymer, a cellulose, a wax, a fatty acid, shellac, zein, hydrogenated vegetable oil, hydrogenated castor oil, polyvinylpyrrolidone, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinyl-alcohol copolymers, polyethylene glycols, non-crosslinked polyvinylpyrrolidone, polyvinyl acetates, polyvinylacetate copolymers or any combination thereof.

In some embodiments, the pharmaceutical or veterinary compositions are formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candelilla wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In some embodiments, the pharmaceutical or veterinary compositions are a powder that can be included into a tablet or a suppository. In alternative embodiments, a formulation or pharmaceutical preparation of the invention can be a 'powder for reconstitution' as a liquid to be drunk or otherwise administered.

In some embodiments, the pharmaceutical or veterinary compositions can be administered in a cream, gel, lotion, liquid, feed, or aerosol spray. In some embodiments, a bacteriophage is immobilized to a solid surface using any substance known in the art and any technology known in the art, for example, but not limited to immobilization of bacteriophages onto polymeric beads using technology as outlined in U.S. Pat. No. 7,482,115, which is incorporated herein by reference. Phages may be immobilized onto appropriately sized polymeric beads so that the coated beads may be added to aerosols, creams, gels or liquids. The size of the polymeric beads may be from about 0.1 μm to 500 μm, for example 50 μm to 100 μm. The coated polymeric beads may be incorporated into animal feed, including pelleted feed and feed in any other format, incorporated into any other edible device used to present phage to the animals, added to water offered to animals in a bowl, presented to animals through water feeding systems. In some embodiments, the compositions are used for treatment of surface wounds and other surface infections using creams, gels, aerosol sprays and the like.

In some embodiments, the pharmaceutical or veterinary compositions can be administered by inhalation, in the form of a suppository or pessary, topically (e.g., in the form of a lotion, solution, cream, ointment or dusting powder), epi- or transdermally (e.g., by use of a skin patch), orally (e.g., as a tablet, which may contain excipients such as starch or lactose), as a capsule, ovule, elixirs, solutions, or suspensions (each optionally containing flavoring, coloring agents and/or excipients), or they can be injected parenterally (e.g., intravenously, intramuscularly or subcutaneously). For parenteral administration, the compositions may be used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner. In a preferred embodiment, a bacteriophage and/or polypeptide of the present invention is administered topically, either as a single agent, or in combination with other antibiotic treatments, as described herein or known in the art.

In some embodiments, the pharmaceutical or veterinary compositions can also be dermally or transdermally administered. For topical application to the skin, the pharmaceutical or veterinary composition can be combined with one or a combination of carriers, which can include but are not limited to, an aqueous liquid, an alcohol base liquid, a water soluble gel, a lotion, an ointment, a nonaqueous liquid base, a mineral oil base, a blend of mineral oil and petrolatum, lanolin, liposomes, proteins carriers such as serum albumin or gelatin, powdered cellulose carmel, and combinations thereof. A topical mode of delivery may include a smear, a spray, a bandage, a time-release patch, a liquid-absorbed wipe, and combinations thereof. The pharmaceutical or veterinary composition can be applied to a patch, wipe, bandage, etc., either directly or in a carrier(s). The patches, wipes, bandages, etc., may be damp or dry, wherein the phage and/or polypeptide (e.g., a lysin) is in a lyophilized form on the patch. The carriers of topical compositions may comprise semi-solid and gel-like vehicles that include a polymer thickener, water, preservatives, active surfactants, or emulsifiers, antioxidants, sun screens, and a solvent or mixed solvent system. U.S. Pat. No. 5,863,560 discloses a number of different carrier combinations that can aid in the exposure of skin to a medicament, and its contents are incorporated herein.

For intranasal or administration by inhalation, the pharmaceutical or veterinary composition is conveniently delivered in the form of a dry powder inhaler or an aerosol spray presentation from a pressurized container, pump, spray, or nebuliser with the use of a suitable propellant, e.g., dichlorodifluoromethane, trichlorofluoromethane, dichlorotetrafluoroethane, a hydrofluoroalkane such as 1,1,1,2-tetrafluoroethane or 1,1,1,2,3,3,3-heptafluoropropane, carbon dioxide, or other suitable gas. In the case of a pressurized aerosol, the dosage unit may be determined by providing a valve to deliver a metered amount. The pressurized container, pump, spray, or nebuliser may contain a solution or suspension of the active compound, e.g., using a mixture of ethanol and the propellant as the solvent, which may additionally contain a lubricant, e.g., sorbitan trioleate. Capsules and cartridges (made, for example, from gelatin) for use in an inhaler or insufflator may be formulated to contain a powder mix of the bacteriophage and/or polypeptide of the invention and a suitable powder base such as lactose or starch.

For administration in the form of a suppository or pessary, the pharmaceutical or veterinary composition can be applied topically in the form of a gel, hydrogel, lotion, solution, cream, ointment, or dusting powder. Compositions of the invention may also be administered by the ocular route. For ophthalmic use, the compositions of the invention can be formulated as micronized suspensions in isotonic, pH adjusted, sterile saline, or, preferably, as solutions in isotonic, pH adjusted, sterile saline, optionally in combination with a preservative such as a benzalkonium chloride. Alternatively, they may be formulated in an ointment such as petrolatum.

Dosages and desired drug concentrations of the pharmaceutical and veterinary composition compositions of the present invention may vary depending on the particular use. The determination of the appropriate dosage or route of administration is within the skill of an ordinary physician. Animal experiments can provide reliable guidance for the determination of effective doses in human therapy.

For transdermal administration, the pharmaceutical or veterinary composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compounds can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Subject, Regimen and Administration

The subject according to the invention is an animal, preferably a mammal, even more preferably a human. However, the term "subject" can also refer to non-human animals, in particular mammals such as dogs, cats, horses, cows, pigs, sheep, donkeys, rabbits, ferrets, gerbils, hamsters, chinchillas, rats, mice, guinea pigs and non-human primates, among others, or non-mammals such as poultry, that are in need of treatment.

The human subject according to the invention may be a human at the prenatal stage, a new-born, a child, an infant, an adolescent or an adult at any age.

In a particular embodiment, the subject is carrying a HLA-DQ haplotype which binds to human $MYH6_{614-629}$ (typically of sequence SEQ ID NO: 17); more particularly (i) a HLA-DQB1*03 variant (in particular encoded by DQB1*03:01, DQB1*03:02, DQB1*03:03, DQB1*03:04, or DQB1*03:05 alleles) and/or (ii) a HLA-DQA1*01:02 or a HLA-DQA1*05:01 variant; still particularly a HLA-DQ7 (for example encoded by DQA1*02:01/DQB1*03:01, DQA1*03:01/DQB1*03:01, DQA1*03:03/DQB1*03:01, DQA1*03:01/DQB1*03:04, DQA1*03:02/DQB1*03:04, DQA1*04:01/DQB1*03:01, DQA1*05:05/DQB1*03:01, or DQA1*06:01/DQB1*03:01 alleles), HLA-DQ8 (for example encoded by DQA1*03:01/DQB1*03:02 or DQA1*03:02/DQB1*03:02 alleles) or HLA-DQ9 (for example encoded by DQA1*02:01/DQB1*03:03 or DQA1*03:02/DQB1*03:03 alleles) haplotype.

In a preferred embodiment, the subject has been diagnosed with, or is at risk of developing myocarditis or DCM. Diagnostic methods of determining *Bacteroides* sp. infection are well known by the man skilled in the art.

In a particular embodiment, the subject has never received any treatment prior to the administration of the vectors, delivery vehicles, bacteria, engineered bacteria, antibiotics, bacteriocins or endolysins according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention.

In a particular embodiment, the subject has already received at least one line of treatment, preferably several lines of treatment, prior to the administration of the vectors, delivery vehicles, bacteria, engineered bacteria, antibiotics, bacteriocins or endolysins according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention.

In a particular embodiment, the subject suffers from cancer. In a more particular embodiment, the subject has already received an immune-checkpoint inhibitor treatment, more particularly a combination of anti-CTLA-4 and anti-PD-1 therapy, in particular to treat cancer.

In a particular embodiment, the subject suffers from an auto-immune disease, in particular from sarcoidosis, rheumatoid arthritis, dermatomyositis, systemic lupus erythematosus (SLE) or giant cell myocarditis.

In a more particular embodiment, the subject suffers from systemic lupus erythematosus (SLE). More particularly, the subject carries a mutation in the gene encoding the 3'-5' DNA exonuclease TREX1.

In a particular embodiment, the subject suffers from a bacterial, viral, parasital, protozoan or fungal infection, which may cause myocarditis.

In a particular embodiment, the subject has already received an antiretroviral treatment, an antipsychotic treatment, an anticancer treatment and/or anti-parasite treatment, such as an anti-malaria treatment.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with vectors, delivery vehicles, bacteria, engineered bacteria, antibiotics, bacteriocins or endolysins according to the invention, preferably a payload according to the invention, particularly a payload packaged into a delivery vehicle according to the invention, preferably a packaged plasmid or phagemid into a bacterial virus particle according to the invention, or with a pharmaceutical or veterinary composition according to the invention, is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the infection, disorder and/or disease persists.

The form of the pharmaceutical or veterinary compositions, the route of administration and the dose of administration of vectors, delivery vehicles, bacteria, engineered bacteria, antibiotics, bacteriocins or endolysins according to the invention, preferably of a payload according to the invention, particularly of a payload packaged into a delivery vehicle according to the invention, preferably of a packaged plasmid or phagemid into a bacterial virus particle according to the invention, or of a pharmaceutical or veterinary composition according to the invention can be adjusted by the man skilled in the art according to the type and severity of the infection (e.g. depending on the bacteria species involved in the disease, disorder and/or infection and its localization in the patient's or subject's body), and to the patient or subject, in particular its age, weight, sex, and general physical condition.

Particularly, the amount of vectors, delivery vehicles, bacteria, engineered bacteria, antibiotics, bacteriocins or endolysins according to the invention, preferably a payload according to the invention, particularly a payload packaged into a delivery vehicle according to the invention, preferably a packaged plasmid or phagemid into a bacterial virus particle according to the invention, or of a pharmaceutical or veterinary composition according to the invention, to be administered has to be determined by standard procedure well known by those of ordinary skills in the art. Physiological data of the patient or subject (e.g. age, size, and weight) and the routes of administration have to be taken into account to determine the appropriate dosage, so as a therapeutically effective amount will be administered to the patient or subject.

For example, the total amount of delivery vehicles, particularly a payload packaged into a delivery vehicle according to the invention, preferably a plasmid or phagemid packaged into a bacterial virus particle according to the invention, for each administration is comprised between $10^4$ and $10^{15}$ delivery vehicles.

Definitions

«Vector»

As used herein, the term "vector" refers to any construct of sequences that are capable of expression of a polypeptide in a given host cell. If a vector is used then the choice of vector is dependent upon the method that will be used to transform host bacteria as is well known to those skilled in the art. Vectors can include, without limitation, plasmid vectors and recombinant phage vectors, or any other vector known in that art suitable for delivering a polypeptide of the invention to target bacteria. The skilled artisan is well aware of the genetic elements that must be present on the vector in order to successfully transform, select and propagate host cells comprising any of the isolated nucleotides or nucleic acid sequences of the invention.

«Delivery Vehicle»

As used herein, the term «delivery vehicle» refers to any vehicle that allows the transfer of a payload into a bacterium.

There are several types of delivery vehicle encompassed by the present invention including, without limitation, bacteriophage scaffold, virus scaffold, bacterial virus particle, chemical based delivery vehicle (e.g., cyclodextrin, calcium phosphate, cationic polymers, cationic liposomes), protein-based or peptide-based delivery vehicle, lipid-based delivery vehicle, nanoparticle-based delivery vehicles, non-chemical-based delivery vehicles (e.g., transformation, electroporation, sonoporation, optical transfection), particle-based delivery vehicles (e.g., gene gun, magnetofection, impalefection, particle bombardment, cell-penetrating peptides) or donor bacteria (conjugation).

Any combination of delivery vehicles is also encompassed by the present invention.

The delivery vehicle can refer to a bacteriophage derived scaffold and can be obtained from a natural, evolved or engineered capsid.

In some embodiment, the delivery vehicle is the payload as bacteria are naturally competent to take up a payload from the environment on their own.

In a particular embodiment, the delivery vehicle is a bacterial virus particle, in particular a packaged phagemid.

In a particular embodiment, the delivery vehicle, in particular the bacteriophage, bacterial virus particle or packaged phagemid, comprising the vector of the invention is incapable of self-reproduction.

In the context of the present invention, "self-reproduction" is different from "self-replication", "self-replication" referring to the capability of replicating a nucleic acid, whereas "self-reproduction" refers to the capability of having a progeny, in particular of producing new delivery vehicles, said delivery vehicles being either produced empty or with a nucleic acid of interest packaged.

By "delivery vehicle incapable of self-reproduction" is meant herein that at least one, several or all functional gene(s) necessary to produce said delivery vehicle is(are) absent from said delivery vehicle (and from said vector included in said delivery vehicle). In a preferred embodiment, said at least one, several or all functional gene(s) necessary to produce said delivery vehicle is(are) present in the donor cell as defined above, preferably in a plasmid or in a helper phage present in the donor cell as defined above, enabling the production of said delivery vehicle in said donor cell.

In the context of the invention, said functional gene necessary to produce delivery vehicle may be absent through (i) the absence of the corresponding gene or (ii) the presence of the corresponding gene but in a non-functional form.

In an embodiment, the sequence of said gene necessary to produce said delivery vehicle is absent from said delivery vehicle. In a preferred embodiment, the sequence of said gene necessary to produce said delivery vehicle has been replaced by a nucleic acid sequence of interest, in particular by a nucleic acid sequence encoding enzymes or systems for inducing genetic modifications, as defined above.

Alternatively, said gene necessary to produce said delivery vehicle is present in said delivery vehicle in a non-functional form, for example in a mutant non-functional form, or in a non-expressible form, for example with deleted or mutated non-functional regulators. In a preferred embodiment, said gene necessary to produce said delivery vehicle is present in said delivery vehicle in a mutated form which renders it non-functional in the target cell, while remaining functional in the donor cell.

In the context of the invention, genes necessary to produce said delivery vehicle encompass any coding or non-coding nucleic acid required for the production of said delivery vehicle.

Examples of genes necessary to produce said delivery vehicle include genes encoding phage structural proteins; phage genes involved in the control of genetic expression; phage genes involved in transcription and/or translation regulation; phage genes involved in phage DNA replication; phage genes involved in production of phage proteins; phage genes involved in phage proteins folding; phage genes involved in phage DNA packaging; and phage genes encoding proteins involved in bacterial cell lysis.

«Payload»

As used herein, the term «payload» refers to any nucleic acid sequence or amino acid sequence, or a combination of both (such as, without limitation, peptide nucleic acid or peptide-oligonucleotide conjugate) transferred into a bacterium with a delivery vehicle.

The term «payload» may also refer to a plasmid, a vector or a cargo.

The payload can be a phagemid or phasmid obtained from natural, evolved or engineered bacteriophage genome. The payload can also be composed only in part of phagemid or phasmid obtained from natural, evolved or engineered bacteriophage genome.

In some embodiment, the payload is the delivery vehicle as bacteria are naturally competent to take up a payload from the environment on their own.

«Nucleic Acid»

As used herein, the term "nucleic acid" refers to a sequence of at least two nucleotides covalently linked together which can be single-stranded or double-stranded or contains portion of both single-stranded and double-stranded sequence. Nucleic acids of the present invention can be naturally occurring, recombinant or synthetic. The nucleic acid can be in the form of a circular sequence or a linear sequence or a combination of both forms. The nucleic acid can be DNA, both genomic or cDNA, or RNA or a combination of both. The nucleic acid may contain any combination of deoxyribonucleotides and ribonucleotides, and any combination of bases, including uracil, adenine, thymine, cytosine, guanine, inosine, xanthine, hypoxanthine, isocytosine, 5-hydroxymethylcytosine and isoguanine. Other examples of modified bases that can be used in the present invention are detailed in Chemical Reviews 2016, 116 (20) 12655-12687. The term "nucleic acid" also encompasses any nucleic acid analogs which may contain other backbones comprising, without limitation, phosphoramide, phosphorothioate, phosphorodithioate, O-methylphosphoroamidite linkage and/or deoxyribonucleotides and ribonucleotides nucleic acids. Any combination of the above features of a nucleic acid is also encompassed by the present invention.

"Phagemid" and "Packaged Phagemid"

As used herein the term "phagemid" or "phasmid" are equivalent and refer to a recombinant DNA vector comprising at least one sequence of a bacteriophage genome and which is preferably not able of producing progeny, more particularly a vector that derives from both a plasmid and a bacteriophage genome. A phagemid of the disclosure comprises a phage packaging site and optionally an origin of replication (ori), in particular a bacterial and/or phage origin of replication. In one embodiment, the phagemid does not comprise a bacterial origin of replication and thus cannot replicate by itself once injected into a bacterium. Alternatively, the phagemid comprises a plasmid origin of replication, in particular a bacterial and/or phage origin of replication.

As used herein, the term "packaged phagemid" refers to a phagemid which is encapsidated in a bacteriophage scaffold, bacterial virus particle or capsid. Particularly, it refers to a bacteriophage scaffold, bacterial virus particle or capsid devoid of a bacteriophage genome. The packaged phagemid may be produced with a helper phage strategy, well known from the man skilled in the art. The helper phage comprises all the genes coding for the structural and functional proteins that are indispensable for the phagemid according to the invention to be encapsidated. The packaged phagemid may be produced with a satellite virus strategy, also known from the man skilled in the art. Satellite virus are subviral agent and are composed of nucleic acid that depends on the co-infection of a host cell with a helper virus for all the morphogenetic functions, whereas for all its episomal functions (integration and immunity, multicopy plasmid replication) the satellite is completely autonomous from the helper. In one embodiment, the satellite genes can encode proteins that promote capsid size reduction of the helper phage, as described for the P4 Sid protein that controls the P2 capsid size to fit its smaller genome.

«Peptide»

As used herein, the term "peptide" refers both to a short chain of at least 2 amino acids linked between each other and to a part of, a subset of, or a fragment of a protein which part, subset or fragment being not expressed independently from the rest of the protein. In some instances, a peptide is a protein. In some other instances, a peptide is not a protein and peptide only refers to a part, a subset or a fragment of a protein. Preferably, the peptide is from 4, 5, 6, 7, 8, 9, 10, 11, 12, 13, 14, 15 amino acids to 4, 5, 6, 7, 8, 9, 10, 11, 12, 13, 14, 15, 20, 25, 30, 40, 50, 100, 200 amino acids in size.

Example

Materials and Methods

Mice

MYH6-specific TCR transgenic mice (TCR-M) on the BALB/c background have been previously described (8). TCRM mice were maintained as heterozygous and transgene-negative littermates were used as controls. TCRM mice were re-derived to germ-free conditions by axenic 2-cell stage embryo transfer into pseudopregnant germ-free recipient females at the Clean Mouse Facility, University of Berne, Switzerland, and bred and maintained under germ-free conditions in flexible film isolators. Germ-free status was routinely monitored by culture-dependent (aerobic and anerobic) and -independent (Sytox DNA stain of cecal contents) methods and were additionally confirmed pathogen-free. In the indicated experiments, germ-free TCRM mice were transferred at 4 or 8 weeks of age to the SPF facility in the Institute of Immunobiology, Kantonsspital St. Gallen and co-housed with SPF TCRM mice and transgene-negative littermates. $Rag1^{-/-}$ and DO11.10 mice were obtained from the Jackson laboratories. Homozygous OVA-TCR transgenic mice (DO11.10) were mated with SPF BALB/c Thy1.1 mice from the TCRM colony of the St. Gallen facility and offspring were used for analysis. $Rag1^{-/-}$ mice were co-housed with TCRM mice 3 weeks before set-up of the breeding pairs. All mice were on the BALB/c genetic background and were maintained in individually ventilated cages. Experiments were performed in accordance with federal and cantonal guidelines (Tierschutzgesetz) under permission numbers SG15/06, SG16/07, SG17/07 and BE55/14 following review and approval by the respective Cantonal Veterinary Offices (St. Gallen and Berne, Switzerland).

Human Serum Samples and Clinical Data

Serum samples from patients enrolled in two different clinical studies were analyzed: (i) "Cardiac β1-adrenoceptor autoantibodies in human heart disease: rationale and design of the Etiology, Titre-Course, and Survival" (ETiCS, AMITIS arm) (27), EC permission No 186/07 (Table 2) and (ii) "Dissecting the role of cross-reactive antimicrobial T and B cell responses in myocarditis and heart failure—an exploratory research project Micro-DCM", EC permission No 2017-01853 (Table 3 and Table 4).

TABLE 2

Demographic details and HLA-DQB1* alleles of ETiCS-AMITIS myocarditis patients and healthy control group[1]

| Patient No. | Age (years)[2] | Sex[3] | HLA-DQB1* | | Diagnosis by EMB[4] |
|---|---|---|---|---|---|
| 1 | 21.3 | Male | 03:01 | 03:01 | Yes |
| 2 | 32.8 | Male | 03:01 | 06:02 | Yes |
| 3 | 58.3 | Female | 03:02 | 06:03 | Yes |
| 4 | 54.4 | Female | 02:02 | 06:04 | Yes |
| 5 | 52.8 | Male | 03:01 | 03:01 | Yes |
| 6 | 50.1 | Male | 03:02 | 06:02 | Yes |
| 7 | 35.2 | Male | 03:02 | 03:02 | Yes |
| 8 | 31.1 | Male | 02:01 | 03:01 | Yes |
| 9 | 64.7 | Male | 02:01 | 03:02 | Yes |
| 10 | 42.0 | Male | 03:02 | 04:02 | Yes |
| 11 | 24.1 | Male | 03:02 | 03:03 | Yes |
| 12 | 21.4 | Male | 02:02 | 03:01 | Yes |
| 13 | 23.8 | Male | 03:01 | 06:04 | Yes |
| 14 | 46.1 | Male | 03:01 | 03:03 | Yes |
| 15 | 20.1 | Male | 03:03 | 06:02 | Yes |
| 16 | 28.9 | Male | 05:01 | 06:02 | Yes |
| 17 | 39.5 | Male | 02:02 | 05:03 | Yes |
| 18 | 21.1 | Male | 04:02 | 06:02 | Yes |
| 19 | 25.3 | Male | 03:01 | 06:84 | Yes |
| 20 | 27.7 | Male | 02:02 | 04:02 | Yes |
| 21 | 18.5 | Male | 05:01 | 06:03 | Yes |
| 22 | 69.0 | Male | 03:01 | 05:03 | Yes |
| 23 | 18.6 | Male | 03:01 | 03:01 | Yes |
| 24 | 53.7 | Male | n.d.[5] | n.d.[5] | Yes |
| 25 | 32.0 | Male | n.d.[5] | n.d.[5] | Yes |

[1]Healthy controls sera were obtained at the base line visit of the interventional study registered as ISRCTN18360696. Female to male ratio of 1:0.38 (N = 18) and mean age of 35 ± 8.3 years.
[2]Mean age of is 36.5 ± 15.5 years in ETiCS/AMITIS.
[3]Female to male ratio of 1:11.5 in ETiCS/AMITIS.
[4]EMB: Endomyocardial biopsy.
[5]n.d. non-determined.

TABLE 3

Demographic details, HLA-DQB1* alleles and diagnosis of Micro-DCM patients.

| Patient No. | Age (years)[1] | Sex[2] | HLA-DQB1* | | Diagnosis[3] |
|---|---|---|---|---|---|
| 1 | 69.9 | Female | 03:01 | 03:01 | Heart failure |
| 2 | 23.6 | Male | 02:01 | 03:01 | Myocarditis |
| 3 | 19.2 | Male | 03:02 | 06:03 | Myocarditis |
| 4 | 25.8 | Male | 03:01 | 03:02 | Myocarditis |
| 5 | 23.9 | Female | 02:02 | 06:03 | Myocarditis |
| 6 | 40.9 | Female | 05:01 | 06:03 | Myocarditis |
| 7 | 37.0 | Male | 05:01 | 06:03 | Myocarditis |
| 8 | 54.9 | Male | 02:01 | 04:02 | Heart failure |
| 9 | 63.5 | Male | 02:01 | 02:02 | Myocarditis |
| 10 | 65.0 | Male | 03:02 | 06:02 | Myocarditis |
| 11 | 42.8 | Male | 02:01 | 03:03 | Myocarditis |
| 12 | 47.7 | Male | 02:01 | 06:03 | Heart failure |
| 13 | 20.0 | Male | 03:03 | 06:02 | Myocarditis |
| 14 | 39.1 | Female | 03:03 | 05:03 | Myocarditis |
| 15 | 26.0 | Male | 04:02 | 05:01 | Myocarditis |
| 16 | 51.2 | Male | 02:02 | 05:03 | Heart failure |
| 17 | 30.5 | Male | 03:01 | 05:03 | Myocarditis |

[1]Mean age in myocarditis patients is 35.8 ± 15.2 and 55.9 ± 9.7 years for heart failure patients.
[2]Female to male ratio for myocarditis patients of 1:3.3 and 1:3 for heart failure patients.
[3]Myocarditis: patients with typical late enhancement pattern in cardiac MRI and exclusion of coronary artery disease by angiography or computed tomography. Heart failure: patients with left ventricular ejection fraction ≤40%, no obvious mechanism underlying left ventricular dysfunction and no significant coronary artery by invasive angiography (no stenosis >50% in any main vessel).

TABLE 4

Demographic details and HLA-DQB1* alleles of healthy volunteers.

| Volunteer No. | Age (years)[1] | Sex[2] | HLA-DQB1* | |
|---|---|---|---|---|
| 1 | 31.5 | Female | 02:01 | 03:03 |
| 2 | 40.3 | Male | 03:01 | 05:03 |
| 3 | 33.2 | Male | 03:01 | 05:01 |
| 4 | 55.4 | Male | 03:01 | 03:01 |
| 5 | 27.7 | Female | 06:04 | 06:02 |
| 6 | 35.1 | Male | 03:01 | 05:01 |
| 7 | 26.7 | Female | 02:02 | 03:19 |
| 8 | 31.8 | Male | 03:01 | 05:01 |
| 9 | 31.1 | Male | 03:03 | 05:02 |
| 10 | 41.2 | Female | 03:05 | 03:01 |
| 11 | 46.5 | Female | 03:02 | 05:02 |
| 12 | 32.8 | Female | 02:02 | 06:04 |

[1]Mean age 36.1 ± 8.3 years.
[2]Female to male ratio 1:1.

All study Participants provided written informed consent in accordance with the Declaration of Helsinki and the International Conference on Harmonization Guidelines for Good Clinical Practice. All regulations were followed according to the German or Swiss authorities and according to the clinical protocols. The retrospective part of this study (AMITIS cohort) is a secondary investigation using patient samples collected from existing clinical trials. Therefore, the sample sizes in this report were determined by the original clinical trial designs and sample availability; no additional inclusion/exclusion criteria were applied. The sample size calculation for the Micro-DCM study has not been done because of the exploratory nature of the study design.

Histology and Myocarditis Scoring

Histological analysis was performed as previously described (8). Briefly, hearts were fixed in 4% formaldehyde (Formafix) for at least 12 h and embedded in paraffin. Histopathological changes were evaluated following hematoxylin/eosin (HE) and Elastica van Gieson (EVG) staining. Myocarditis severity was evaluated using a semiquantitative scoring system: 0, no inflammation; 1, <100 inflammatory cells involved, small inflammatory lesions; 2, >100 inflammatory cells involved, larger inflammatory lesions; 3, >10% of the heart section involved in inflammation; 4, >30% of the heart section involved in inflammation; 5, >30% of the heart section involved in inflammation with extensive fibrosis and dilation of ventricle. Images from heart sections were acquired using a Leica DMRA microscope.

Flow Cytometry and Cell Isolation

For the generation of single-cell suspensions, spleens and lymph nodes were collected in BSS and were mechanically disrupted on a metallic grid. To confirm the presence of heart-infiltrating cells, mice received 2 μg of anti-CD45.2 BV510 or anti-Thy1.1 PE i.v. 5 min before being euthanized in the indicated experiments. Euthanized animals were perfused with 20 ml PBS and small heart tissue pieces were placed into a 6-well dish filled with RPMI 1640 medium containing 2% FCS, 20 mM HEPES (Lonza), 1 mg/ml collagenase 0 (Sigma) and 25 μg/ml DNaseI (Applichem) and incubated at 37° C. under continuous stirring. The remaining tissue pieces were mechanically disrupted and mononuclear cells were purified by centrifugation (25 min at 800×g, 4° C.) on a 30-70% Percoll gradient (GE Healthcare). For isolation of colonic lamina propria cells, colons were flushed and tissue was harvested and incubated three times for 15 min at room temperature under constant agitation with BSS containing 5% FCS (Lonza), 5 mM EDTA (Sigma), 10 mM HEPES (Sigma) and 1 mM OTT in order to dissociate the epithelial layer. The tissue was subsequently washed with SS containing 10 mM HEPES and digested three times for 20 min at 37° C. with 120 μg/ml collagenase P (Roche), 25 μg/ml DNAse I (Applichem) and 5 μg/ml Dispase I (Roche) in RPMI-1640; after obtaining a single cell suspension, cells were purified by a 30-70% Percoll gradient. Single-cell suspensions were first stained with the fixable viability dye Zombie Aqua (Biolegend) and incubated for 30 min on ice; after washing, cells were incubated for 20 min at 4° C. in PBS containing 2% FCS and 10 mM EDTA with fluorochrome-labeled antibodies (Table 5). Cells were acquired with a BD LSRFortessa (BD Biosciences) and analyzed using FlowJo software (Treestar Inc) following stablished guidelines (32).

TABLE 5

Antibodies used in this study

| Clone | Reagent | Conjugate | Dilution | Source |
|---|---|---|---|---|
| IA8 | anti-Ly6G | PE | 1:200 | Pharmigen |
| AL-21 | anti-Ly6C | PerCP | 1:100 | Biolegend |
| 145-2C11 | anti-CD3e | PerCP | 1:100 | Biolegend |
| 30-F11 | anti-CD45 | APC-Cy7 | 1:100 | Biolegend |
| 30-F11 | anti-CD45 | PE | 1:100 | Biolegend |
| IM7 | anti-CD44 | APC-Cy7 | 1:100 | Biolegend |
| MEL-14 | anti-CD62L | BV-421 | 1:100 | Biolegend |
| MI/70 | anti-CD11b | BV-711 | 1:100 | Biolegend |
| FJK16S | anti-FoxP3 | PeCy7 | 1:100 | eBioscience |
| B20.1 | anti-Vα2 | APC | 1:100 | BDBioscience |
| MR5-2 | anti-Vβ8 | FITC | 1:100 | BDBioscience |
| RM4-5 | anti-CD4 | BV-605 | 1:100 | Biolegend |
| XMG-1.2 | anti-IFN © | APC | 1:100 | Biolegend |
| TC11-18H10.1 | anti-IL17 | PE | 1:100 | Biolegend |
| KJ1-26 | anti-TCR D011.10 | FITC | 1:100 | Biolegend |
| 2G9 | anti-IA/IE | FITC | 1:100 | BDBioscience |
| SA011F11 | anti-CX3CR1 | APC-Fire750 | 1:100 | Biolegend |
| 2B10C42 | anti-MERTK | APC | 1:100 | Biolegend |
| 104 | anti-CD45.2 | BV-605 | 1:100 | Biolegend |
| SA203G11 | anti-CCR2 | BV-421 | 1:100 | Biolegend |

TABLE 5-continued

Antibodies used in this study

| Clone | Reagent | Conjugate | Dilution | Source |
|---|---|---|---|---|
| X54-5/7.1 | anti-CD64 | PeCy7 | 1:250 | Biolegend |
| DATK32 | anti-α4β7 | APC | 1:100 | Biolegend |
| 29-2L17 | anti-CCR6 | PE | 1:100 | Biolegend |
| 11-44-2 | anti-IgA | PE | 1:50 | eBiosciences |

Immunofluorescence

Murine colonic tissue and lymph nodes were fixed overnight at 4° C. in freshly prepared 4% paraformaldehyde (Merck Millipore) under agitation. Tissues were embedded and oriented in 4% low melting agarose (Invitrogen) in PBS and serially sectioned with a vibratome (Leica VT-1200). 30-40 μm thick sections were blocked in PBS containing 10% FCS, 1 mg/ml anti-Fcγ receptor (BD Biosciences) and 0.1% Triton X-100 (Sigma). Tissues were incubated overnight at 4° C. with the following antibodies: anti-mouse CD4, anti-mouse E-Cadherin (Biolegend). Microscopy was performed using a confocal microscope (LSM-710, Carl Zeiss). Microscopy data were recorded with ZEN 2010 software (Carl Zeiss, Inc.) and processed in Imaris Versions 7 (Bitplane).

Ex Vivo Restimulation and Cytokine Production of Murine T Cells

For assessment of ex vivo production of IFN-γ and IL-17, $10^6$ lymphocytes were incubated for 3.5 h at 37° C. in 96-well round-bottom plates in 200 μL of RPMI per 5% FCS supplemented with 10 μg/mL brefeldin A (Sigma). Cells were stimulated with 0.25 μg of the different peptides (see below), or phorbol myristate acetate (50 ng/ml; Sigma)/ionomycin (500 ng/ml; Sigma) (PMA/I) as positive control, or were left untreated. After surface molecule labelling, cells were stained with the fixable viability dye Zombie Aqua (Biolegend). Cells were fixed with cytofix-cytoperm (BD Biosciences) for 20 min. Fixed cells were incubated at 4° C. for 40 min with permeabilization buffer (2% FCS, 0.5% saponin in PBS) containing antibodies to CD3, CD4, IFN-γ and IL-17A. Samples were measured using a BD LSR Fortessa (BD Biosciences). Data were analyzed using FlowJo software (Tree Star, Inc.).

Generation of B. thetaiotaomicron ΔBT1626 Mutant Strain

Deletion of the B. thetaiotaomicron β-galactosidase (BT1626) was done using a counterselection system described in (33). A strain with a clean deletion of tdk (BT2275) in the VPI-5482 background, resistant to the toxic nucleotide analog 5-fluoro-2'-deoxyuridine (5FUdR) was used as a starting point. Genomic regions 1 kb upstream and downstream of BT1626, respectively, were amplified via colony pcr, with primers including overhangs for Gibson assembly into the plasmid pExchange-tdk (33), digested with the enzymes XbaI and SalI. All primers are listed in Table 6.

TABLE 6

Primers used for the deletion of B. thetaiotaomicron BT1626

| Name | Sequence | Purpose |
|---|---|---|
| Bt_bgal_ko_1 | AAG ATA ACA TTC GAG TCG ACT ATT TCG GCA ATA ATA CGC TGA AAG (SEQ ID NO: 3) | Forward primer 1 kb upstream of BT1626, with Gibson overhang homologous to pExchange-tdk. |
| Bt_bgal_ko_2 | CAA ATG CAA TCA GTT TCA GGC ATT ATT ATA TTG TTT TTT GGT GAC TGG T (SEQ ID NO: 4) | Reverse primer immediately upstream of BT1626, with Gibson overhang homologous to the downstream region of BT1626. |
| Bt_bgal_ko_3 | CCT GAA ACT GAT TGC ATT TGG (SEQ ID NO: 5) | Forward primer immediately downstream of BT1626 |
| Bt_bgal_ko_4 | GCG GTG GCG GCC GCT CTA GAA GTC GTT TGT TGT TTT CTT CG (SEQ ID NO: 6) | Reverse primer 1 kb downstream of BT1626, with Gibson overhang homologous to pExchange-tdk. |
| 1626_250us_f | CAC ATA GTA GTT TTC TTT CGT C (SEQ ID NO: 7) | Control primer 250 bp upstream of BT1626. |
| 1626_264inside_r | GCG AAA CTG ACG GAT CAG (SEQ ID NO: 8) | Control primer 264 bp inside the BT1626 coding sequence. |
| 1626_250ds_r | TCG GAC GAT AAT GCG ACT T (SEQ ID NO: 9) | Control primer 250 bp downstream of BT1626. |

Figure 7A:
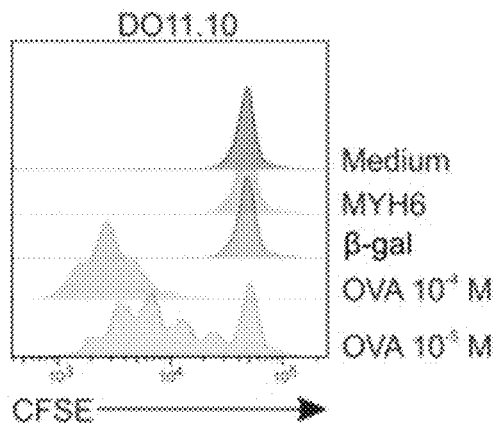
FIGS. 7A-I. Specificity and immune interaction of *Bacteroides* mimic peptide-specific CD4$^+$ T cells.
Figure 7C:
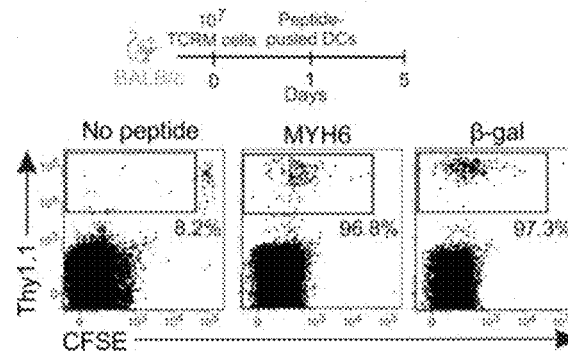
Figure 7B:
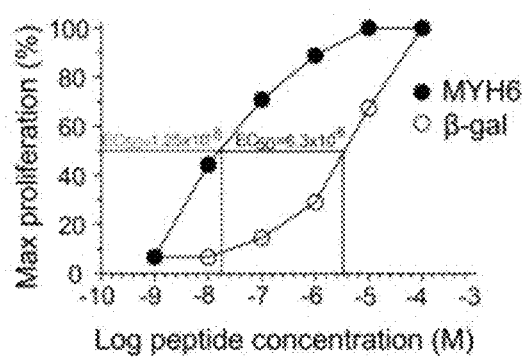
Figure 7D:
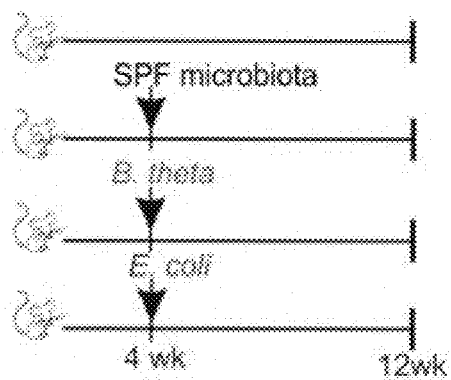
Figure 7E:
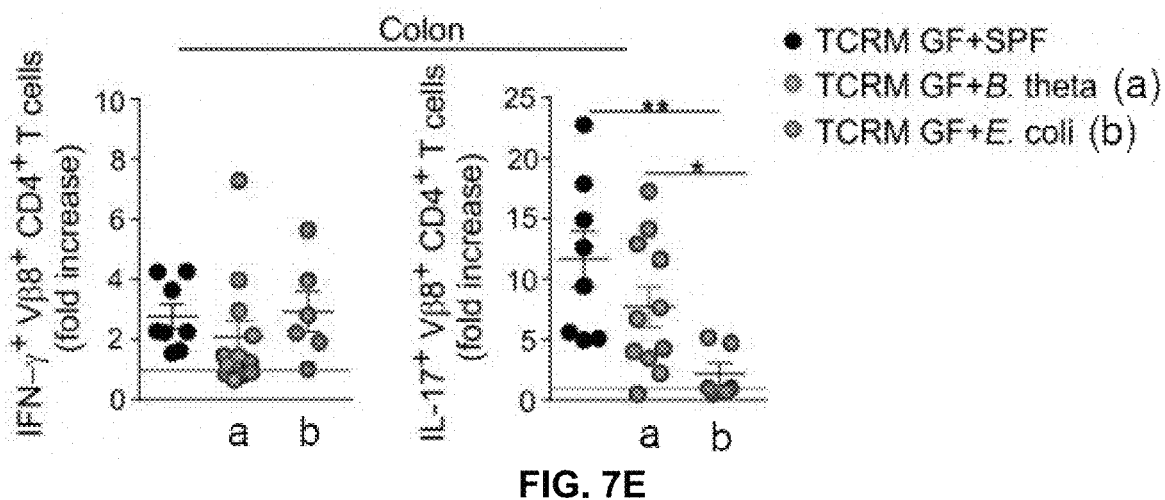
Figure 7F:
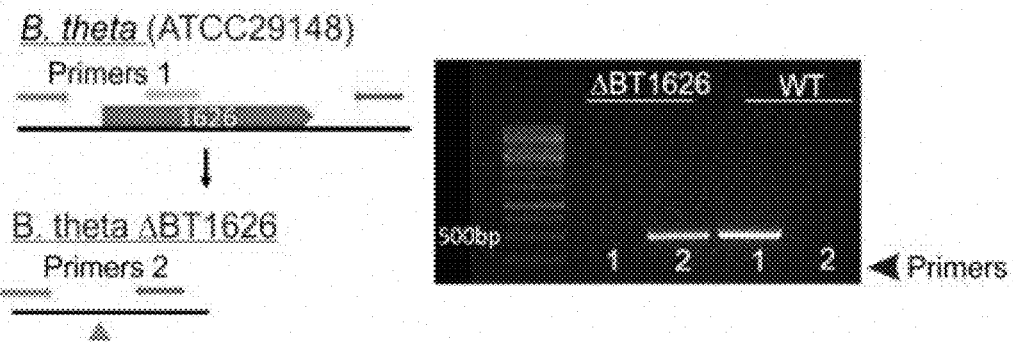

The plasmid was then transformed into the conjugative E. coli strain SM10 and conjugated into the B. thetaiotaomicron Δtdk. The resulting colonies are resistant to erythromycin and have the complete plasmid inserted into the chromosome resulting from a single homologous recombination event. Counterselection on plates containing 200 μg/ml 5FUdR led to a second recombination event, and either to a reversion to the wild type state or to the deletion of BT1626. Successful deletion was tested using PCR with control primers, and clones with a clean deletion of the gene were further used (FIG. 7F and Table 6). All plates used for generating mutants were Brain Heart Infusion (Oxoid), supplemented with 2% agar (Sigma), 10% defibrinated sheep blood (Sigma), 1 μg/ml Hemin (Sigma). 200 μg/ml FUdR (Sigma), 25 µg/ml erythromycin (Sigma), and 200 µg/ml gentamicin (Sigma) were added before pouring the plates when needed.

Bacterial Culture and Monocolonized Mice

The different *Bacteroides thetaiotaomicron* strains (ATCC29148, ATCC29148$^{\Delta tdk}$ or ATCC29148$^{\Delta tdk}$ΔBT1626) were grown anaerobically overnight at 37° C. in Brain Heart Infusion (BHI, CM1135, Oxoid) with the addition of hemin (1 µg/ml, Sigma) and menadione (0.5 µg/ml, Sigma). *E. coli* BL21(DE3) was grown in LB medium at 37° C. Overnight broth culture of *B. thetaiotaomicron* or *E. coli* was washed once in PBS and gavaged intra-gastrically (500 µl/mouse corresponding to $10^9$ bacteria/mouse) to germ-free mice (at least 3-4 week old). Germ-free and monocolonized animals were kept in flexible film isolators until the end of the experiments and monitored regularly for excluding any contaminations using Sytox staining on fecal pellets for GF animals, Gram staining and 16S rRNA sequencing on fecal pellets for monocolonized animals (34). The effects of mono-colonization in TCRM mice were analyzed 8 weeks post colonization.

Myocarditis Induction in Rag1$^{-/-}$ Mice

Spleens were collected from TCRM mice and disrupted on a 70-µm cell strainer. Red blood cells were lysed by osmotic shock and $10^6$ splenocytes were injected intravenously in 4 wk mice in the lateral tail vein of Rag1$^{-/-}$ mice. Seven days after adoptive transfer, mice were bled to confirm CD4$^+$ T cell expansion. Disease activity scores and analysis of T cell activation in the heart and colonic lamina propria were performed at day 28 post adoptive transfer.

Antibiotics Treatment

Mice were treated for 4 or 16 weeks with the following antibiotics in the drinking water (i) a broad spectrum antibiotic mixture; Sulfadoxine 400 mg/l and Trimethoprim 80 mg/l (Borgal; Veterinaria) or (ii) Streptomycin 200 mg/l (Sigma-Aldrich) to reduce the proportion of Bacteroidetes (35) or iii) Vancomycin 100 mg/l. Metronidazole (Sigma-Aldrich) was administered by gavage at a dose of 2 mg every 3 days to Sulfadoxine and Trimethoprim-treated mice or a separate group of mice for exclusive Metronidazole treatment.

Ex Vivo Proliferation Assay and Peptides Used in the Study

Spleen cells were labelled with 10 µl of 5 mM carboxyfluorescein succinimidyl ester (CSFE, dissolved in DMSO) (Molecular Probes) in 10 ml of PBS for 10 min at 37° C. The staining reaction was stopped with 1 mL FCS (Lonza), followed by washing with PBS. A total of $2\times10^5$ splenocytes/well were seeded in 96-well round-bottom plate and MYH6$_{614-629}$ (RSLKLMATLFSTYASADR, SEQ ID NO: 10) or *Bacteroides* β-galactosidase$_{11-25}$ (TFLILMAAL-TATFASAQK, SEQ ID NO: 11), *Enterobacter* cysteine hydrolase$_{10-27}$ (LLIGMMSTFSTYASAQET, SEQ ID NO: 12) or OVA$_{323-339}$ (ISQAVHAAHAEINEAGR, SEQ ID NO: 13) peptide was added at the indicated concentrations. CSFE dilution was assessed by flow cytometry after 3 days of incubation at 37° C. All peptides were synthetized by Genscript with >80% of purity.

In Vivo Proliferation of TCRM Cells

Spleen cells were labelled with CFSE as described above and $5\times10^6$ cells were i.v. transferred in to Rag$^{-/-}$ mice. Mice were culled at days 2, 3, 4, or 7 after adoptive transfer and the presence of myosin specific (CD4$^+$Vα2$^+$Vβ8$^+$) cells as well as CFSE dilution was assessed by flow cytometry in single cell suspensions from the mediastinal lymph node, colonic lymph node, colonic lamina propria and heart.

Detection of Bacteria-Specific IgG

High-binding 96-well polystyrene plates (Corning) were coated with $10^7$ CFU of the following bacterial strains *B. theta* ATCC29148, *B. distasionis, B. vulgatus, E. cloacae* ATCC 13047 or *E. coli* K12 in 0.1 M carbonate-bicarbonate buffer, pH 9.5. Plates were incubated for 1 h at 37° C. and then overnight at 4° C. Before use, plates were washed three times with PBS containing 0.05% Tween-20 (PBS-T) (Sigma-Aldrich). Non-specific binding was blocked with 5% non-fat dry milk diluted in PBS (PBS-M) for 1 h at 37° C. After washing, sera were diluted 1:20 in PBS-M and two fold serial dilutions were added to the wells. Plates were incubated for 1 h at 37° C., followed by four washes with PBS-T and then incubated for 1 h of at 37° C. with peroxidase-conjugated rabbit anti-human IgG (1:2500) or rabbit-anti-mouse IgG (1:1000) antibody (in PBS-M, Jackson Immuno Research). After four washes with PBS-T, ortho-phenylenediamine (0.5 mg/ml; Sigma) in 0.1 M citrate buffer, pH 5.6, containing 0.08% $H_2O_2$ was used to develop the reaction. Optical density was measured at 492 nm using an automated ELISA plate reader (Tecan). Absorbance values at 1:160 dilutions are presented in the figures. In human samples high and low responders to *B. thetaiotaomicron* were defined as high responders were patients that had an IgG at diagnosis of A>mean of healthy controls+2 SD.

Bacterial IgA Binding Detected by Flow Cytometry

Fecal-bound IgA was assessed using bacterial flow cytometry for IgA-bound bacteria performed as previously described (36). In brief, fecal pellets were homogenized in 1 ml of staining buffer (PBS+1% (w/v) bovine serum albumin (BSA, Sigma). Tubes were centrifuged at 400 g for 5 minutes to pellet large debris and the supernatant was filtered through a sterile 70 µm cell strainer and transferred to a new tube. Samples were centrifuged at 8000×g for 5 minutes to pellet bacteria and pellets were re-suspended in PBS with SYTO BC (1:1000, Life Technologies) for 15 minutes on ice. Samples were washed with PBS and stained in 100 µl staining buffer containing PE-conjugated anti-mouse IgA (1:75) for 30 minutes on ice. Samples were washed 3 times with PBS and re-suspended for flow cytometry analysis in a FACS CANTO (BD). Bacteria were gated based on forward and side scatter and the gating strategy was verified by SYTO-BC staining. Fecal samples from Rag1$^{-/-}$ mice were used as negative controls to define the threshold for IgA$^-$ and IgA$^+$ populations. Analysis of IgA binding was done using FlowJo (v0.1).

Microbiota Analysis

For microbial composition analysis, the feces from TCRM SPF mice, Tg$^-$ littermates and TCRM GF co-housed with TCRM SPF and Tg$^-$ littermates were used. Microbial composition was assessed by a 16S high-throughput amplicon analysis as described previously (37). The 16S rRNA gene segments spanning the variable V5 and V6 regions were amplified from DNA from the samples, using a multiplex approach with the barcoded forward fusion primer 5'-CCATCTCATCCCTGCGTGTCTCCGACTCAG (SEQ ID NO:14) BARCODE ATTAGATACCCYGGTAGTCC-3' (SEQ ID NO: 23) in combination with the reverse fusion primer 5'-CCTCTCTATGGGCAGTCGGTGA-TACGAGCTGACGACARCCATG-3' (SEQ ID NO: 15). The PCR-amplified 16S V5-V6 amplicons were purified and prepared for sequencing on the Ion torrent PGM system according to the manufacturer's instructions (Life Technologies). Samples with over 10'000 reads were accepted for analysis. Data analysis was performed using the QIIME pipeline version 1.8.0 (38). Operational taxonomic units were picked using UCLUST with a 97% sequence identity threshold, followed by taxonomy assignment using either the latest Greengenes database. For estimation of species diversity within samples (α-diversity), the Shannon index was calculated using the R phyloseq package after rarefaction to even depth to the sample with the lowest number of sequences (34).

Fecal Bacterial DNA Extraction and Quantitative *B. thetaiotaomicron* PCR

Bacterial genomic DNA was extracted using a commercial kit (QIAamp DNA Stool Mini Kit) with minor modifications. Glass beads (Sigma, G4649-10G) were used for an optimal disruption of fecal content and an additional extraction step was introduced after incubation of bacteria with a lysis buffer (20 mg/ml lysozyme—Sigma 62970-5G-F, 2 mM EDTA, 1.2% Triton, 20 mM Tris-HCl). Extracted genomic DNA was used as a template for *B. thetaiotaomicron* PCR amplification and quantification using a real-time PCR machine (Quant Studio 5) and SYBR Green PCR technology (Applied Biosystems, Thermo Fisher Scientific). *B. thetaiotaomicron* was quantified using species specific primers that have been established and validated before (39) (atcgcaaaaataagatgggcaaa and cacaacagccatagcgttcca) with a cycling protocol of denaturation at 95° C. (2 min), 40 cycles of 95° C. (20 sec), 58° C. (20 sec) and 72° C. (30 sec). Each 17 μl qPCR mixture consisted of 8.5 μl of 2×SYBR Green MasterMix (Applied Biosystems, Thermo Fisher Scientific), 1.7 μl of BSA (100 μg/ml), 0.6 μl of each primer (10 μM), 3.60 μl PCR-grade water and 2 μl of extracted genomic DNA. DNA extracted from *B. theta* ATCC29148 was used to construct a standard curve with 10-fold dilutions of DNA templates of known concentrations. Concentrations of DNA used in the standard curves ranged from 33.75 ng/μl equivalent to $10^7$ bacteria to 0.035 pg/μl equivalent to $10^1$ bacteria. The PCR amplifications were performed in duplicates and the detection limit was 0.34 pg/μl ($10^2$ bacteria). Bacterial qPCR signals were normalized to 1 μg of total bacterial DNA.

Bioinformatics Analysis of Peptide Homology and MHC Class II Binding

Proteins encoded in cultured and uncultured bacteria of the NCBI microbial protein database were searched for 15 amino acid sequences similar to $MYH6_{614-629}$ with BLAST p2.3.1 (blast.ncbi.nlm.nih.gov). Predicted binding of the candidate bacterial peptides to the BALB/c mouse $IA^d$ MHC class II was evaluated using the immune epitope database and analysis resource IEDB from the National Institute of Allergy and Infectious diseases online prediction tool (tools.iedb.org/mhcii/). The binding threshold was set at 10, and peptides with percentile ranks lower than the threshold value were predicted to be good MHC II haplotype binders (Table 1).

TABLE 1

Sequences and properties of microbial peptide mimics of $MYH6_{614-629}$.

| Description | Organism | Accession number | Protein length (amino acids) | Amino acid sequence[2] | $IA^d$ binding (percentile)[3] | Murine MYH6 identity (%) |
|---|---|---|---|---|---|---|
| Myosin heavy chain 6 (MYH6) | *Mus musculus* | NP_034986.1 | 1938 | SLKLMATLFSTYASAD (SEQ ID NO: 16) | 2.12 | |
| Myosin heavy chain 6 (MYH6) | *Homo sapiens* | NP_002462.2 | 1939 | SLKLMATLFSSYATAD (SEQ ID NO: 17) | 8.39 | 87.50 |
| β-galactosidase | *Bacteroides faecis*[1] | WP_109116112.1 | 1022 | FLILMAALTATFASAQ (SEQ ID NO: 18) | 2.71 | 56.25 |
| β-galactosidase | *Bacteroides thetaiotaomicron*[1] | SQA30530.1 | 1023 | FLILMAALTATFASAQ (SEQ ID NO: 19) | 2.71 | 56.25 |
| Cysteine hydrolase | *Enterobacter cloacae*[1] | KJX05885.1 | 238 | LIGMMSTFSTYASAQE (SEQ ID NO: 20) | 16.78 | 50.00 |
| MFS transporter | *Enterococcus faecalis*[1] | AW1VI66597.1 | 475 | GMTLMGLSTLFLSTYA (SEQ ID NO: 21) | 14.00 | 37.50 |
| Outer membrane protein 2 | *Chlamydia pneumoniae* | CAA39396.1 | 547 | LETSMAEFTSTNVISL (SEQ ID NO: 22) | 21.87 | 25.00 |

[1] Commensal in human intestinal microbiome.
[2] Amino acids matching to murine $MYH6_{614-628}$ are highlighted by underlining.
[3] MHC class II Iad binding prediction algorithm: IEDB analysis resource (low percentile rank indicates better binding to MHC II molecule).

The predicted binding of human $MYH6_{614-629}$ and *Bacteroides* β-$gal_{11-25}$ peptides to HLA-DQ alleles was performed using the full HLA reference set, which provides >99% of coverage of the HLA allele usage (40). Input sequences from full human myosin heavy chain alpha (myosin heavy chain 6, MYH6) protein (accession number: NP_002462.2) and *B. thetaiotaomicron* β-galactosidase (accession number: SQA30530.1) were used for the prediction in IEDB.

HLA Analysis of Myocarditis Patients

The HLA-genotyping for the AMITIS patients was performed by the Institut für Klinische Transfusionsmedizin und Hämotherapie from the Universitätsklinikum Würzburg. Briefly, genomic DNA was obtained from PBMCs and analyzed by a sequence based typing (SBT) by Sanger sequencing using forward and reverse primers for sequencing the exons 2 and 3 (HLA class II) in a Applied Biosystems Genetic analyzer 3130 xl, instrument (ThermoFisher Scientific), using SBTexcellerator kits (Gendx) and the analysis software SBTengine. The Micro-DCM cohort HLA typing was performed by Illumina sequencing (Histogenetics, USA).

Detection of Anti-β1 Antibodies in the Sera of Patients

To detect anti-β1 antibodies in the sera of patients we used Dynabeads® M-270 Epoxy (Life Technologies) coated for 72 h according to the manufacturer's instructions with 100, 80, 60, 40, 20, 10, 5 or 2.5 µg/ml β1-ECII peptide. Control beads were coated with 10 µg/ml of a scramble peptide comprising the same amino acids of the β1-ECII peptide. After the coating the beads were washed using phosphate-buffered saline (PBS)/0.1% Bovine Serum Albumin (BSA) and stored in PBS/0.1% BSA/0.02% NaN3 until further use. For antibody detection $10^4$ beads of every fraction were seeded into a 96-well-V-bottom plate. After blocking the beads with phosphate-buffered saline (PBS)/10% Bovine Serum Albumin (BSA) (15 min, on ice), a 1:100 dilution in PBS/0.1% BSA/0.02% NaN3 of patient serum, or as negative control pooled human AB serum (Sigma), was incubated with the beads in a total volume of 50 µl (15 min, on ice). As a positive control the rat anti-β1-ECII monoclonal antibody 13F6 was used (10 µg/ml in PBS/0.1% BSA/0.02% NaN3/AB serum 1:100). The beads were washed four times using PBS/0.1% BSA/0.02% NaN3 and transferred to fresh wells before incubation with a 1:100 dilution of the secondary antibody F(ab)2 donkey-anti-human IgG (H+L) FITC (Dianova) in PBS/0.1% BSA/0.02% NaN3 (total volume: 50 µl, 15 min, on ice). 13F6 was detected using F(ab)2 donkey-anti-rat IgG (H+L) PE (Dianova; 1:1000 dilution in PBS/0.1% BSA/0.02% NaN3). After a final washing step the samples were measured on a FACScan flow cytometer and the data analyzed using FlowJo (Treestar). Half maximal binding was determined using GraphPad Prism. When a half maximal binding value was calculable, the serum was defined as antibody-positive.

Human T Cell Stimulation

IFN-γ ELISPOT was performed as described by Lv et. al. with minor modifications (7), Briefly, PBMCs from patients and healthy volunteers were isolated on density gradients. PBMCs were adjusted to $2 \times 10^6$ cells/ml in 0.5 ml of complete IVS medium supplemented with 8% of human serum. Cells were stimulated for 48 h with 0.25 µg/ml of the indicated peptide or left untreated as medium control. After incubation, cells were washed and re-suspended in 0.3 ml of RPMI/10% FOS and approximately $5 \times 10^5$ cells/0.1 ml were dispensed in duplicates into previously coated and blocked ELISPOT plates (IFN-γ base kit, MABTECH). After 24 h of incubation at 37° C. the ELISPOT plates were washed and developed as indicated by the manufacturer. Plates were counted using an ELISPOT reader and analyzed with the software ELISPOT 3.1SR (AID). Number of specific IFN-γ positive cells was calculated as the mean of the duplicates minus the mean of the medium control.

Human Fecal Microbiota Transplantation

Fecal microbiota transplantation was performed as previously reported by Gopalakrishnan et, al (41). Briefly, germ free TCRM and transgene-negative littermates received FMT from myocarditis patients which were previously confirmed to be positive for *B. thetaiotaomicron* and the DQB1*03:02 HLA allele; each patient sample was administered to 4 mice. 200 µl cleared supernatant from 0.1 g/µl human fecal suspension was obtained using a 100 µm strainer and gavaged into mice 3 times over 1 week, *B. thetaiotaomicron* colonization was assessed by qPCR at 14 and 21 days after the first administration.

Statistical Analysis

Statistical analyses were performed with Graphpad Prism 7.0 using unpaired two-tailed Student's t-test or Mann-Whitney U tests. Longitudinal comparison between different groups was performed by one-way ANOVA with Tukey's post-test or two-way ANOVA with Bonferroni's post-test. For allele comparison, the Fisher's exact test was used. Statistical significance was defined as $p<0.05$.

Results

Microbiome-Dependent Inflammatory Cardiomyopathy

Figure 1A:
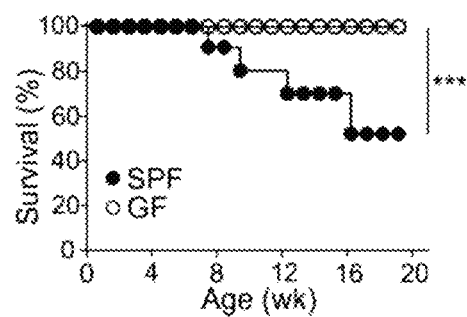
FIGS. 1A-R. Microbiome-dependent transition of autoimmune myocarditis to dilated cardiomyopathy.
Figure 1B:
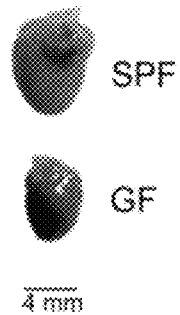
(FIG. 1B) Gross pathology of hearts from 12 week old SPF TCRM and age-matched GF TCRM mice.
Figure 1C:
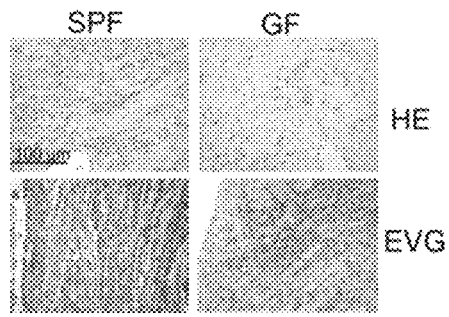
(FIG. 1C) Histological analysis of hearts of 12 week old TCRM mice kept under SPF or GF conditions using hematoxylin-eosin (HE) and elastica-van Gieson (EVG) staining.
Figure 1D:
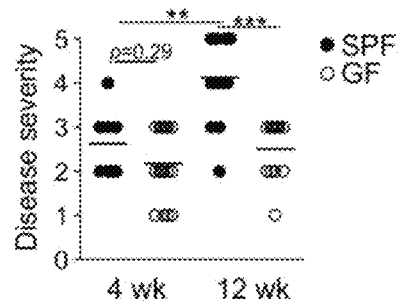
(FIG. 1D) Histopathological disease severity in TCRM mice under SPF and GF conditions. Dots represent values of individual mice; bar indicates mean disease severity.
Figure 1E:
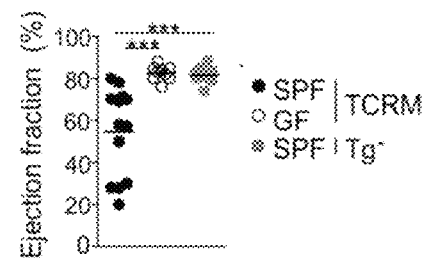
(FIG. 1E-G) Echocardiographic parameters in TCRM mice kept under SPF or GF conditions and in transgene-negative littermate of controls with (FIG. 1E) ejection fraction, (FIG. 1F) fractional shortening and (FIG. 1G) systolic left ventricular internal diameter (LVID) determined in individual mice.
Figure 1F:
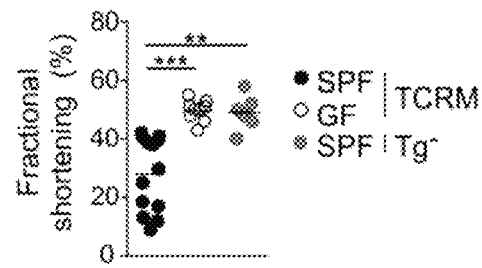
Figure 1G:
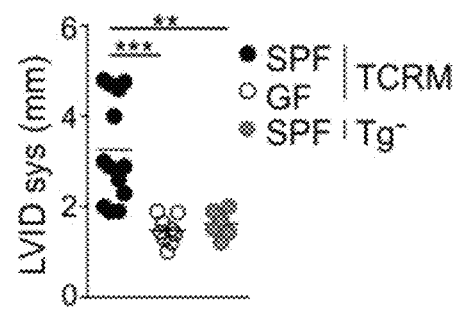

The link between infection with pathogens and the development of autoimmune diseases is well-documented (17, 18), while the impact of commensal bacteria on dysregulated self-reactivity has only recently been uncovered (19-23). Importantly, commensal bacteria such as *Bacteroides* can also dampen autoimmune reactivity both in mice and humans (24, 25). To assess whether the intestinal environment and the vast repertoire of antigens present in the microbiota shape heart-specific autoimmunity, we used transgenic mice that express a MYH6-specific T cell receptor on more than 95% of their CD4$^+$ T cells (TCRM) (8). As described previously (8), all TCRM mice developed spontaneous autoimmune myocarditis and approximately 50% of the animals progressed from autoimmune myocarditis to lethal DCM under specific pathogen free (SPF) housing conditions (FIG. 1A-D). In stark contrast, the lack of a commensal microbiome under germ-free (GF) conditions rescued TCRM mice from progression to the lethal disease (FIG. 1A), abrogated cardiac dilatation (FIG. 1B) and substantially reduced fibrotic remodeling of the cardiac tissue in 12 week old animals (FIG. 1C). Histopathological assessment of disease severity revealed that myocarditis in GF TCRM mice was significantly reduced at 12 weeks when compared to age-matched TCRM mice raised under SPF conditions (FIG. 1D). Echocardiographic analysis of heart functions with recording of the ejection fraction (FIG. 1E), fractional shortening (FIG. 1F) and systolic left ventricle internal diameter (LVID) (FIG. 1G) revealed that hearts of 12 week old GF TCRM mice functioned normally despite the low level cardiac inflammation. The small difference in disease severity at 4 weeks of age and the lack of progressive myocarditis in GF TCRM mice (FIG. 1D) suggested that post-weaning processes such as microbial colonization critically impact disease aggravation in TCRM mice.

Figure 1H:
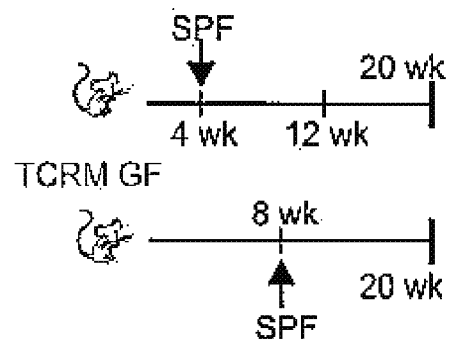
(FIG. 1H-J) Co-housing of GF TCRM mice with SPF TCRM mice at the age of 4 and 8 weeks.
Figure 1I:
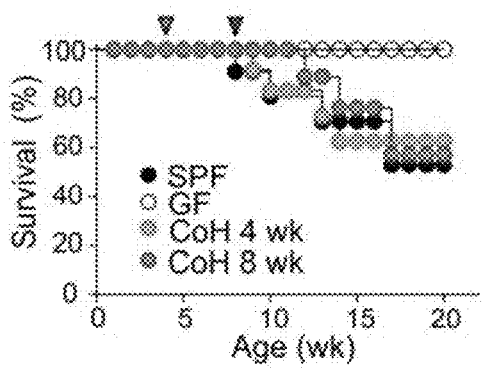
Figure 1J:
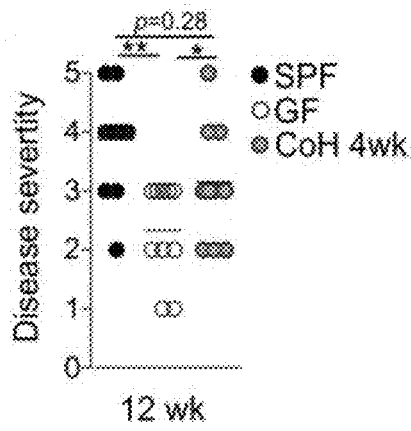
Figure 1K:
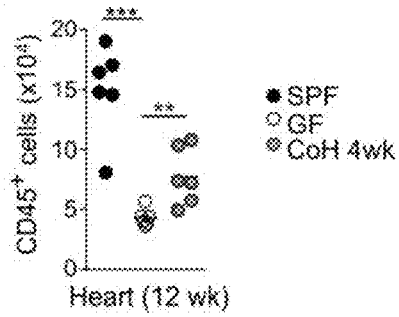
(FIGS. 1K and L) Enumeration of heart-infiltrating cells of 12 week old TCRM mice under SPF and GF conditions or GF TCRM mice co-housed (CoH) for 4 weeks in SPF conditions with (FIG. 1K) CD45$^+$ cells and (FIG. 1L) myosin-specific (Vβ8$^+$ CD4$^+$) cells.
Figure 1L:
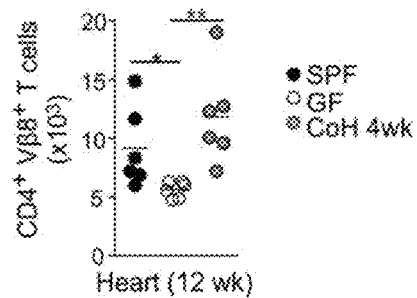
Figure 1M:
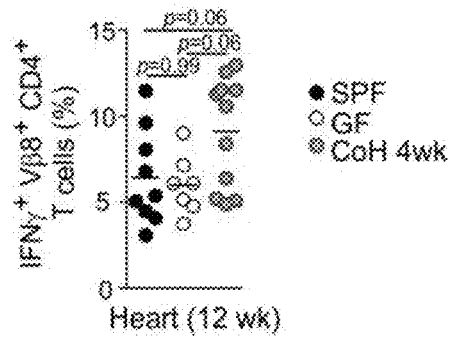
(FIG. 1M) IFN-γ- and (FIG. 1N) IL-17-producing heart-infiltrating MYH6-specific CD4$^+$ T cells (Vβ8$^+$ CD4$^+$).
Figure 1N:
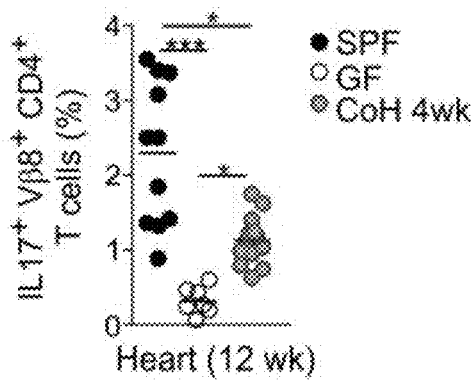
Figure 1O:
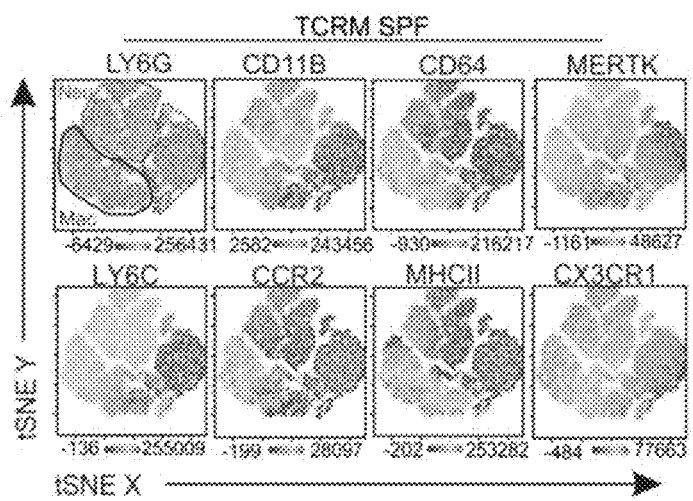
Figure 1P:
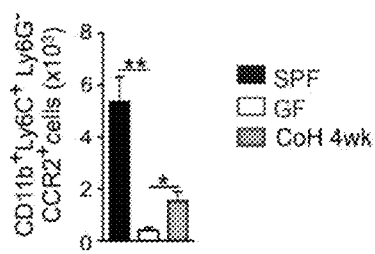
Figure 1Q:
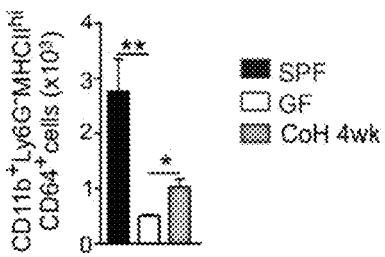
Figure 1R:
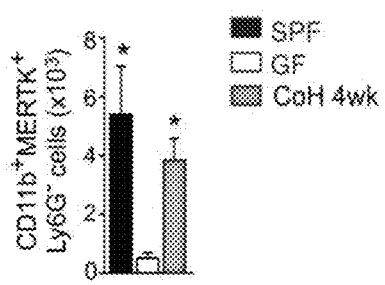
Figure 5A:
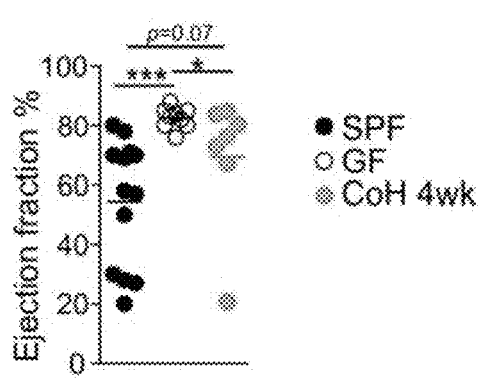
FIGS. 5A-F. Impact of microbial colonization on heart function and inflammation in TCRM mice.
Figure 5C:
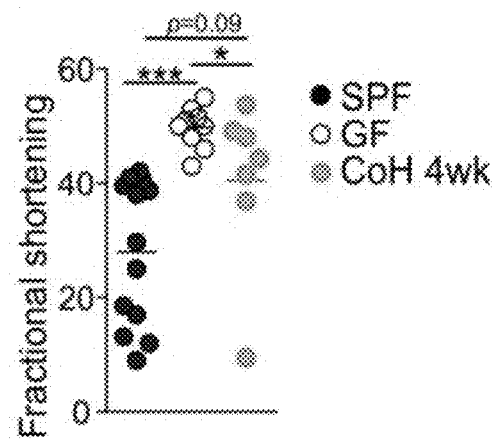
Figure 5B:
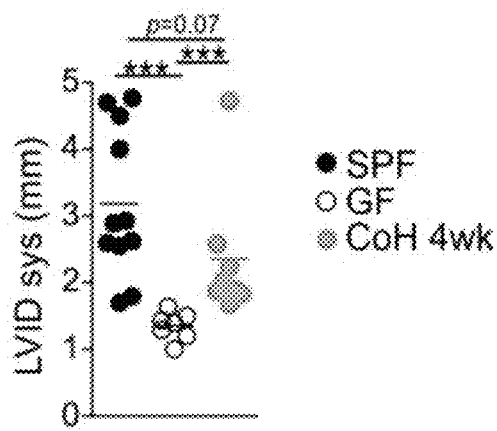
Figure 5D:
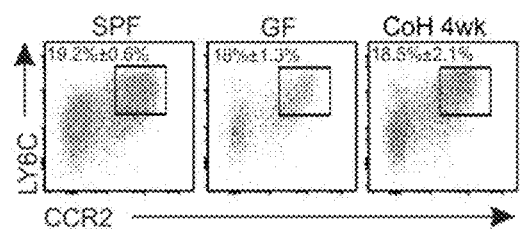
Figure 5E:
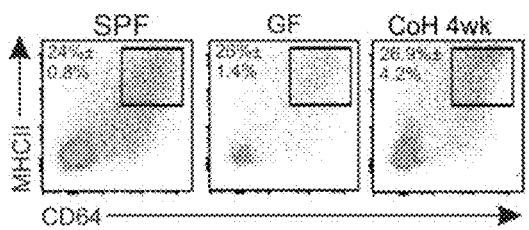
Figure 5F:
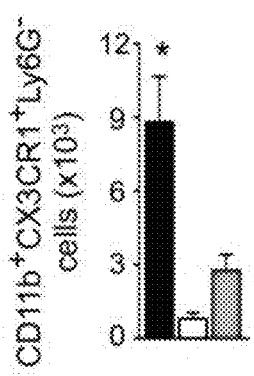
Figure 5F:
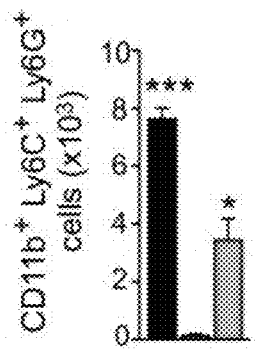
Figure 5F:
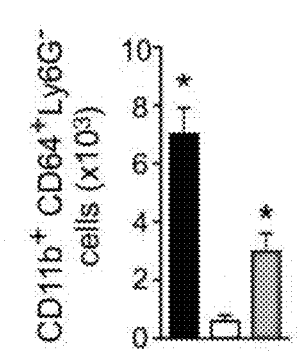

To determine to which extent microbial colonization affected the activation of heart-specific CD4$^+$ T cells, TCRM mice were transferred from GF to the SPF environment at 4 and 8 weeks of age and co-housed (CoH) with SPF TCRM mice (FIG. 1H). Colonization with the SPF microbiome precipitated progression to lethal disease in ex-GF mice within 6-12 weeks (FIG. 1I), significantly exacerbated cardiac inflammation (FIG. 1J) and impaired cardiac function (FIG. 5A-C). Moreover, microbial colonization of GF TCRM mice led to rapid infiltration of the heart with CD45$^+$ immune cells (FIG. 1K) and an overshooting accumulation of MYH6-specific CD4$^+$ T cells that expressed the transgenic Vβ8 chain (FIG. 1L). While IFN-γ production of heart-infiltrating TCRM Th cells did not differ between SPF and GF mice (FIG. 1M), the expression of IL-17 was dependent on the microbial status (FIG. 1N). Co-housing increased the fraction of both IFN-γ- (FIG. 1M) and IL-17-secreting heart-specific CD4$^+$ T cells (FIG. 1N) and promoted the accumulation of inflammatory myeloid cells in the heart tissue (FIG. 1O-R and FIG. 5D-F) including inflammatory monocytes expressing CCR2 (FIG. 1P), MHCII$^{high}$ macrophages (FIG. 1Q) and MERTK$^+$ macrophages (FIG. 1R). These data suggest that the presence of microbiota fosters the imprinting of a Th17 phenotype in heart-specific CD4+ T cells and favors the accumulation of inflammatory monocytes/macrophages in the myocardium of TCRM mice.

Intestinal Peptide Mimics Activate Heart-Specific Th Cells

Figure 2A:
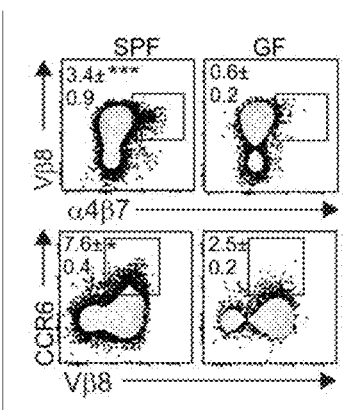
FIGS. 2A-M. Interaction of MYH6-specific CD4$^+$ T cells with the intestinal microbiome.
Figure 2E:
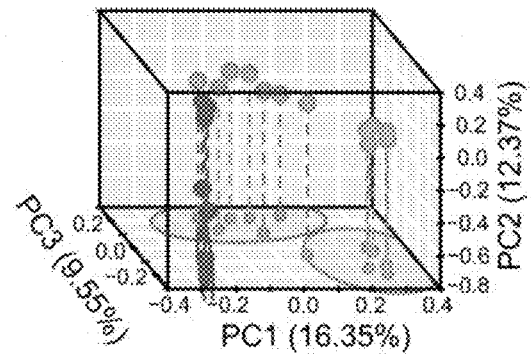
Figure 2B:
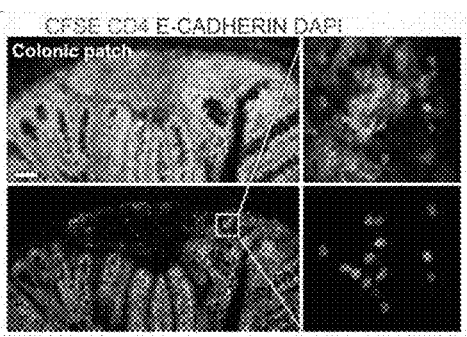
Figure 2F:
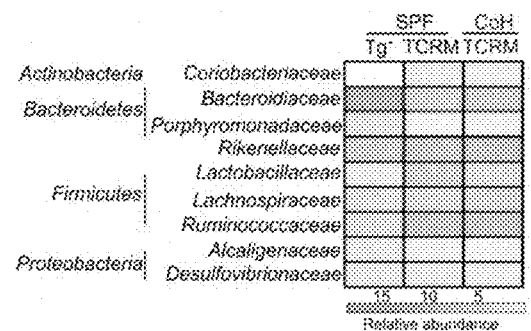
Figure 2C:
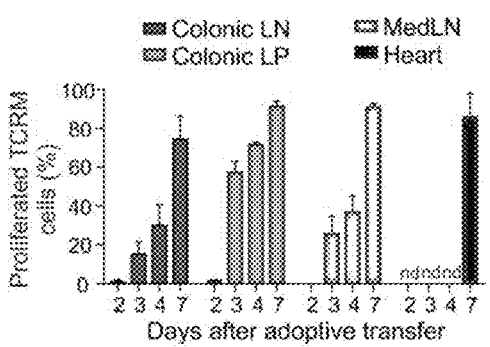
Figure 6A:
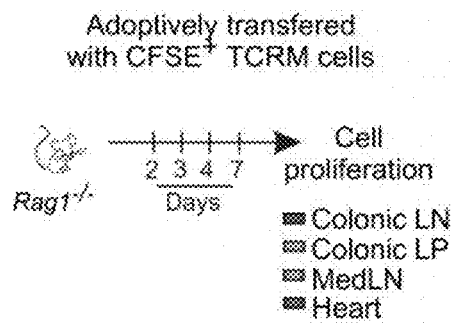
FIGS. 6A-I. Activation TCRM CD4+ cells and interaction with the intestinal microbiome.
Figure 6D:
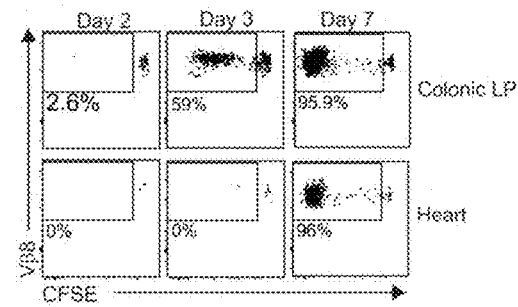
Figure 6B:
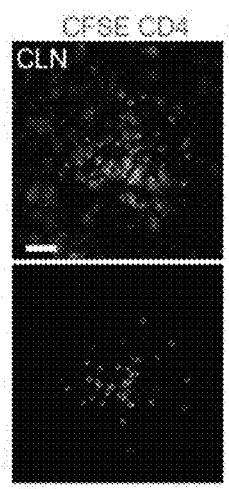
Figure 6E:
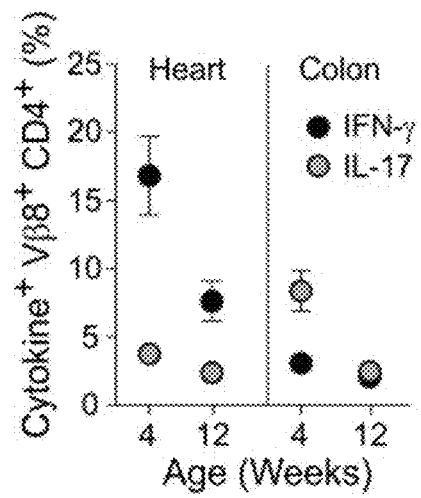
Figure 6C:
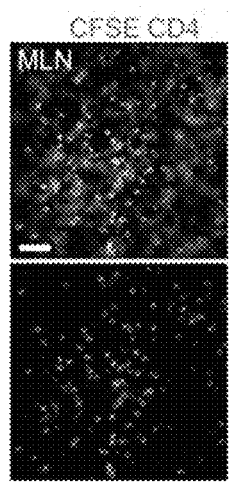
Figure 6F:
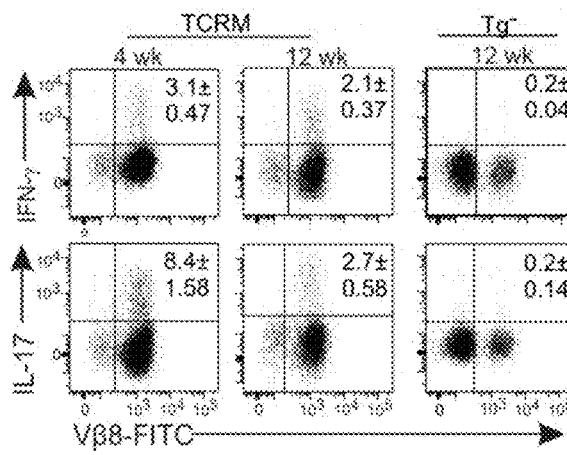
Figure 6G:
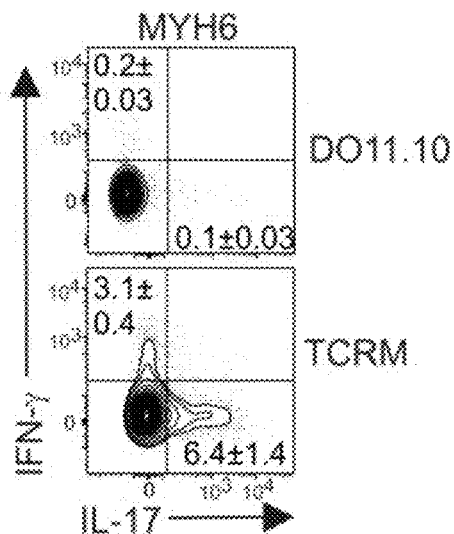

IL-17 determines the severity of experimental myocarditis in mice (6, 8) and appears to promote heart failure in human myocarditis patients (9). Since balancing of Th17 cell activity is crucial for the integrity and immune homeostasis of the intestinal lamina propria (26), we hypothesized that MYH6-specific CD4+ T cells in TCRM mice receive remote activation signals from the intestinal microbiota. Indeed, assessment of mucosal homing molecule expression on heart-infiltrating CD4+ TCRM cells revealed significantly elevated integrin α4β7 and chemokine receptor CCR6 expression under SPF compared to GF conditions (FIG. 2A). Adoptive transfer of dye-labeled TCRM cells into Rag1-deficient BALB/c mice (FIG. 6A) revealed homing of CD4+ cells to the T cell zones of colonic patches (FIG. 2B), colonic lymph nodes (FIG. 6B) and mesenteric lymph nodes (FIG. 6C). The adoptively transferred Vβ8+ CD4+ T cells showed detectable proliferation on day 3 in the lamina propria, the colonic lymph node and the mediastinal lymph node, while heart-infiltrating TCRM cells could only be detected on day 7 (FIG. 2C and FIG. 6D). The CD4+ T cell response in the hearts of 4 week old TCRM mice was dominated by IFN-γ-producing Th cells (FIG. 6E), whereas the colonic lamina propria environment fostered the differentiation of IL-17-producing CD4+ T cells (FIGS. 6E and F). Importantly, only MYH6-specific CD4+ T cells, but not ovalbumin-specific CD4+ T cells from the colonic lamina propria were able to secrete IFN-γ or IL-17 upon ex-vivo re-stimulation with the MYH6 peptide (FIG. 6G). These data indicate that heart-specific Th cells can be activated in the colonic lamina propria and/or the associated lymphoid organs prior to receiving further antigenic stimulation in the heart.

Figure 2G:
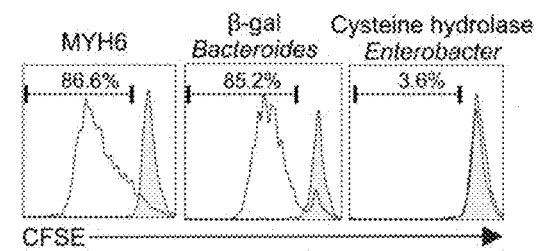
Figure 2D:
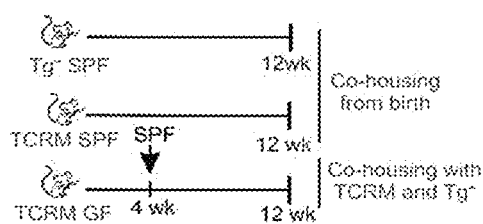
Figure 2H:
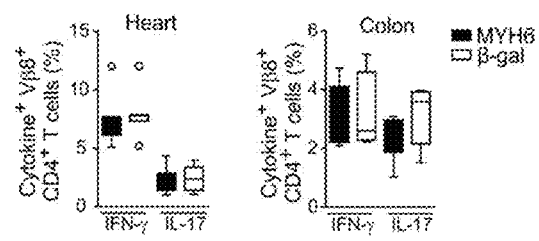
Figure 2I:
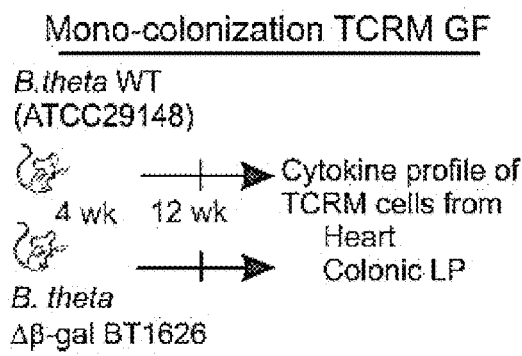
Figure 2K:
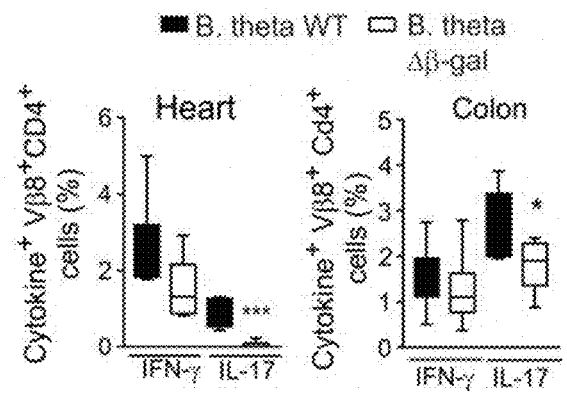
Figure 2J:
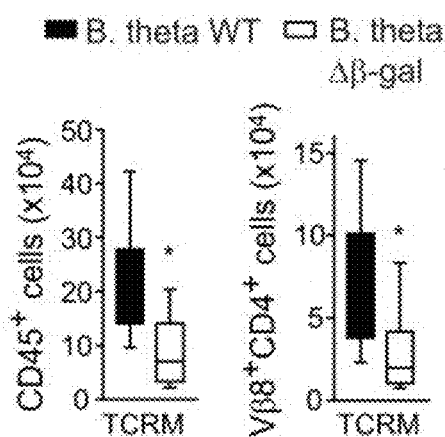
Figure 2L:
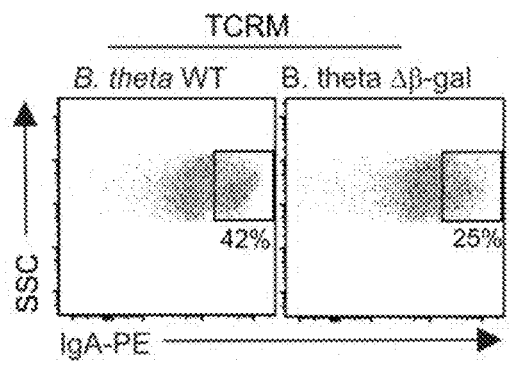
Figure 2M:
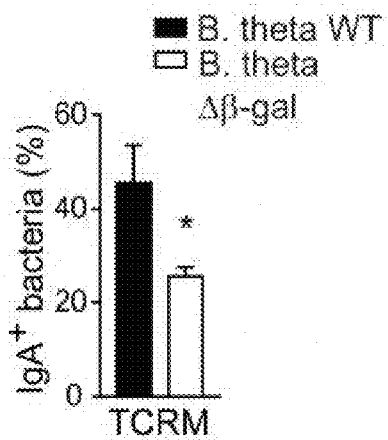
Figure 6H:
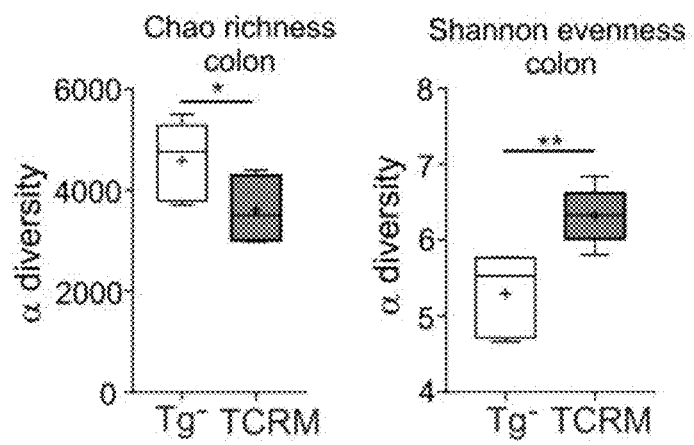
Figure 6I:
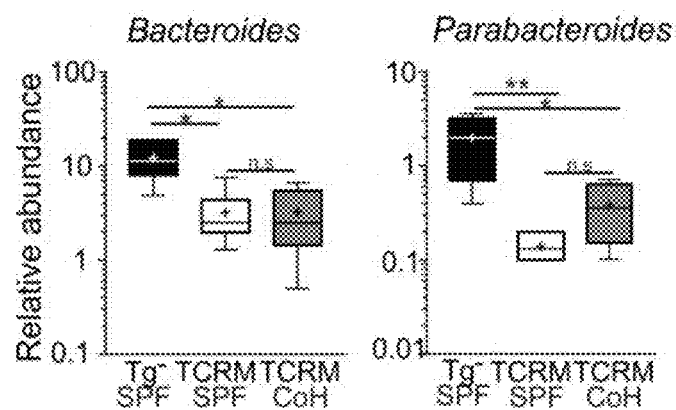
Figure 7G:
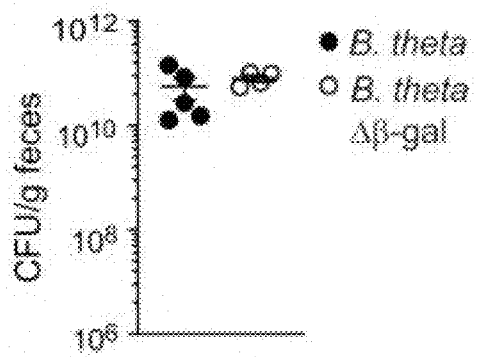
Figure 7H:
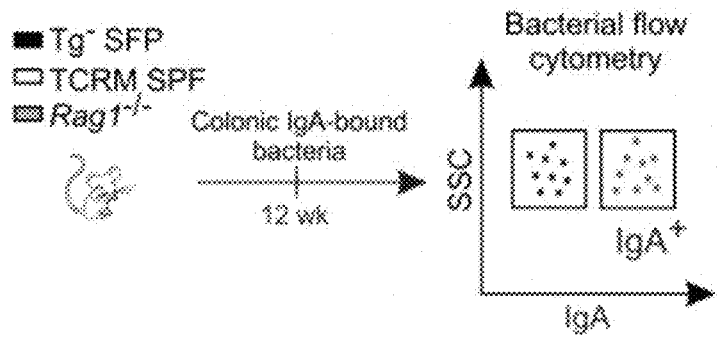
Figure 7I:
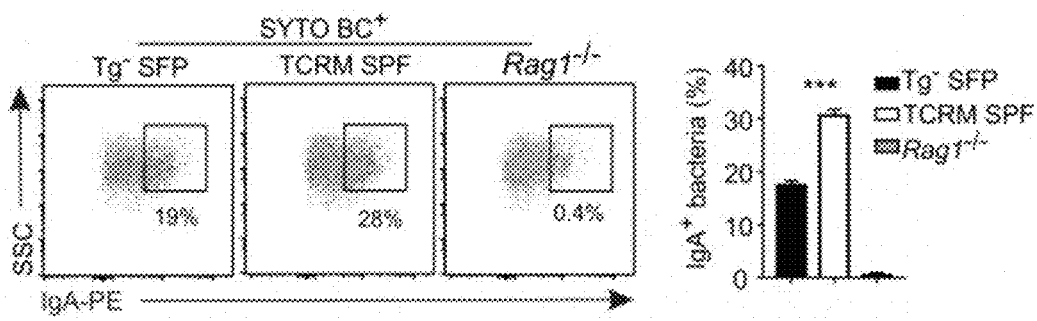

To further explore the interaction of heart-specific Th cells and the intestinal microbiome, 4 week old GF TCRM mice were co-housed with SPF transgene-negative (Tg−) and SPF TCRM littermates (FIG. 2D). Next generation sequencing of 16S rRNA genes amplified from feces revealed that co-housed Tg− and TCRM mice possess disparate microbiomes (FIG. 6H) and that the microbiome of co-housed ex-GF TCRM mice appears to be more similar to the SPF TCRM microbiome (FIG. 2E). More detailed analyses confirmed that GF TCRM mice acquired the microbiome of SPF TCRM mice (FIG. 2F) with particularly high changes in the genera *Bacteroides* and *Parabacteroides* (FIG. 6I). These data suggested that MYH6-specific CD4+ T cells in the TCRM mice impact the composition of the microbiome through antigen-specific interactions. Indeed, an in silico search for potentially cross-reactive epitopes identified two mimic peptides with high similarity to MYH6 in the β-galactosidase (β-gal) of *Bacteroides thetaiotaomicron* (*B. theta*) and *B. faecis* that possesses a homology of 56%, and cysteine hydrolase peptide of *Enterobacter cloacae* with 50% homology (Table 1). The *B. theta* β-gal peptide but not the *Enterobacter cloacae* peptide, induced in vitro proliferation of CD4+ T cells from TCRM mice (FIG. 2G), while ovalbumin-specific CD4+ T cells were not activated by the microbial peptides (FIG. 7A). TCRM CD4+ T cells exhibit a functional avidity of $6.3 \times 10^{-6}$ M for the cross-reactive *B. theta* peptide (FIG. 7B) that facilitated efficient activation of TCRM T cells in vivo by *B. theta* peptide-pulsed dendritic cells (FIG. 6C) and ex vivo re-stimulation of transgenic CD4+ T cells from heart and colon (FIG. 2H) of 12 week old TCRM mice. To elucidate the role of *B. theta* for the activation of TCRM Th cells in the colonic lamina propria, we mono-colonized GF TCRM mice with *B. theta* or *Escherichia* (*E.*). *coli*, or colonized them with our SPF microbiota (FIG. 7D). These analyses showed that only *B. theta* mono-colonization specifically fostered the induction of IL-17 production as seen following SPF colonization (FIG. 7E). The differentiation towards IFN-γ-producing CD4+ T cells was not significantly affected by any of the re-colonization conditions (FIG. 7E). Next, we generated a *B. theta* mutant lacking the β-gal BT1626 gene encoding for the MYH6 peptide mimic (*B. theta* β-gal) (FIG. 7F). Mono-colonization of GF TCRM mice with *B. theta* β-gal or the parental strain (FIG. 2I) resulted in efficient seeding of the intestinal microenvironments with both strains (FIG. 7G), but precipitated significantly reduced accumulation of CD45+ immune cells and Vβ8+ CD4+ T cells in the myocardium (FIG. 2J). Moreover, IL-17 production of myosin-specific CD4+ T cells in heart and colon was significantly reduced when TCRM mice were re-colonized with *B. theta* β-gal (FIG. 2K). Assessment of IgA binding to intestinal bacteria using bacterial flow cytometry (FIG. 7H) indicated that the presence of TCRM cells substantially increases the production of IgA against commensal microbiota under SPF conditions (FIG. 7I). To determine to which extent such increased intestinal IgA production depends on specific antigenic stimulation by the MYH6 mimic peptide, we assessed *B. theta*-specific IgA binding in GF TCRM mice that were mono-colonized with *B. theta* β-gal. Indeed, the absence of the cross-reactive epitope in *B. theta* β-gal led to a significantly reduced IgA response when compared to re-colonization with the parental *B. theta* strain (FIGS. 2L and M). In sum, these data reveal that organ-specific, genuinely autoreactive CD4+ T cells can shape the colonic microbiome and that distinct bacterial communities, here *Bacteroides*, represent a source of mimic peptides that can activate MYH6-specific CD4+ T cells.

Antibiotics Treatment Mitigates Inflammatory Cardiomyopathy

Figure 3A:
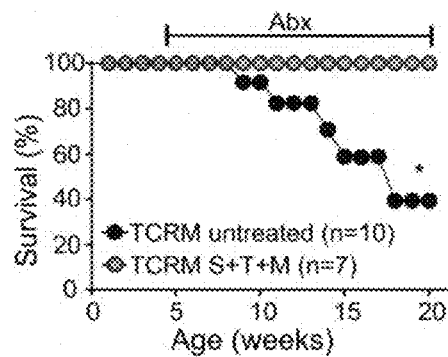
FIGS. 3A-K. Impact of antibiotics treatment on lethal heart disease and immune reactivity in the TCRM model.
Figure 3B:
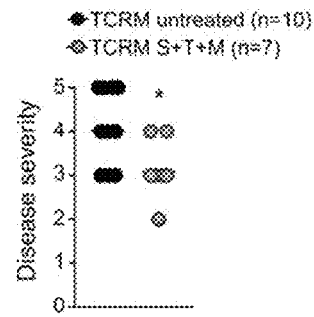
Figure 3C:
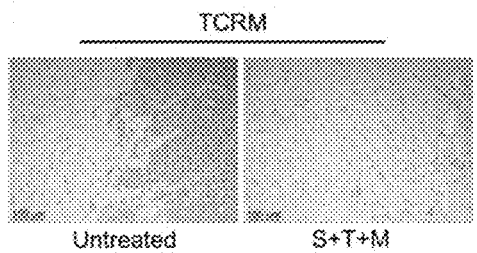
Figure 3D:
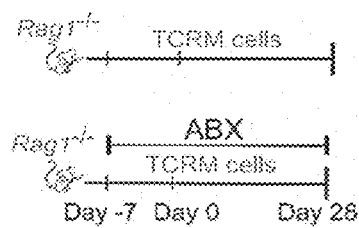
Figure 3E:
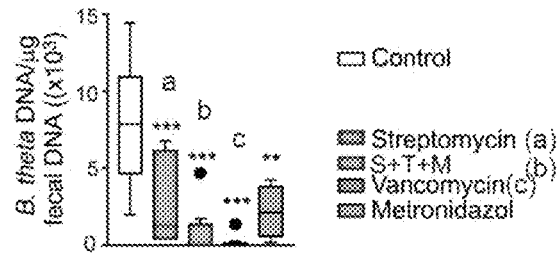
Figure 3F:
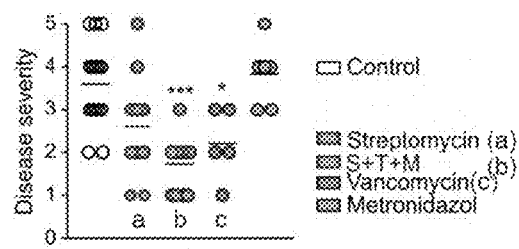
Figure 3G:
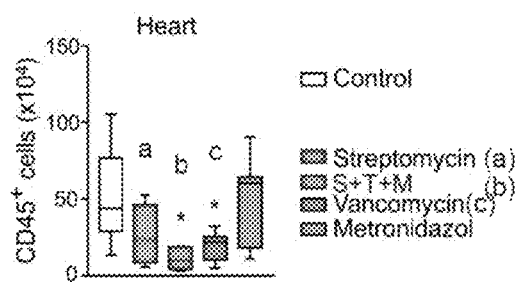
Figure 3H:
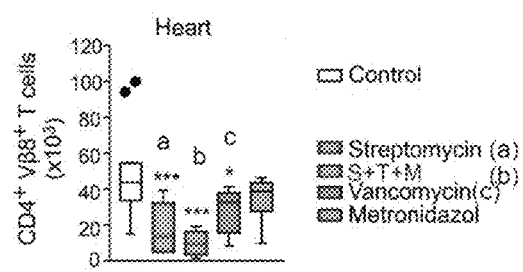
Figure 3I:
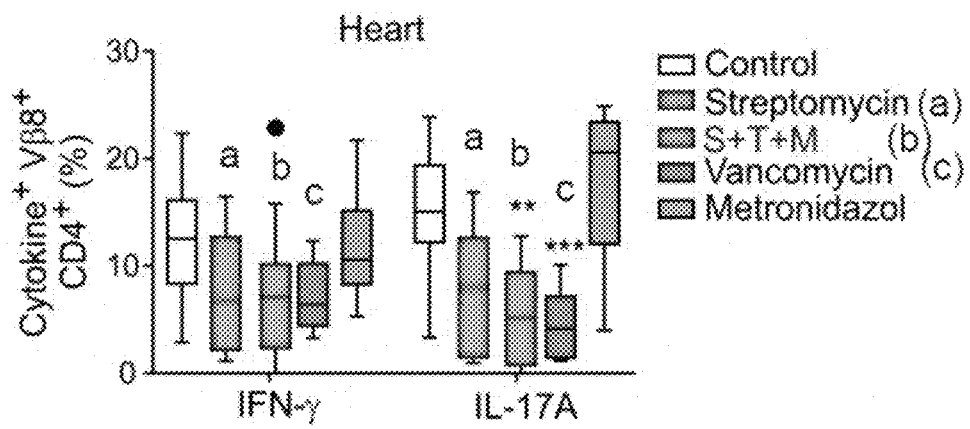
Figure 3J:
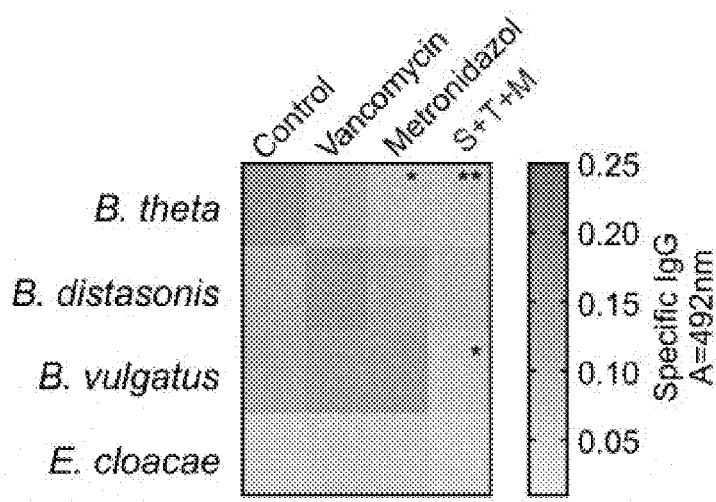
Figure 3K:
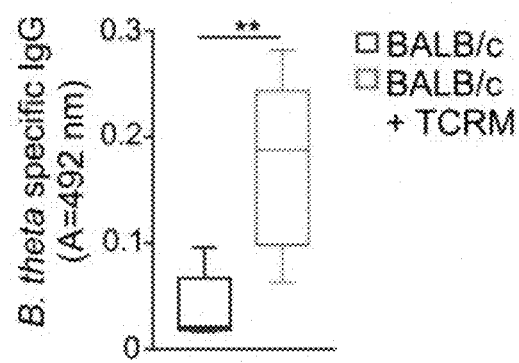
Figure 8A:
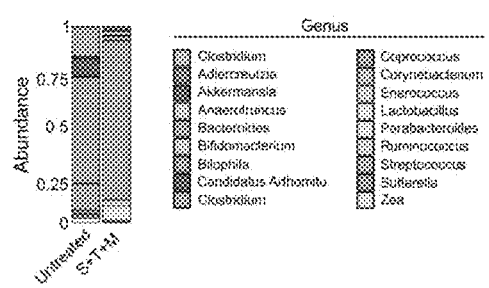
FIGS. 8A-F. Effect of antibiotics treatment on splenic and colonic CD4$^+$ T cells.
Figure 8D:
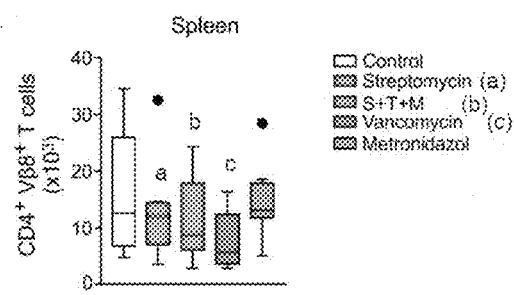
Figure 8B:
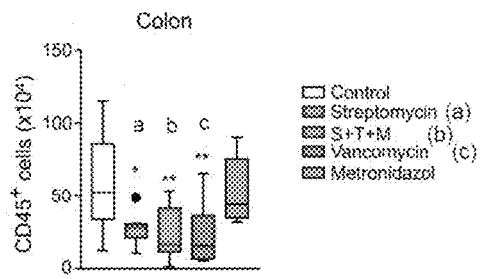
Figure 8E:
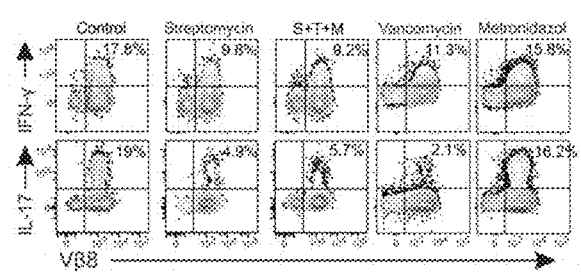
Figure 8C:
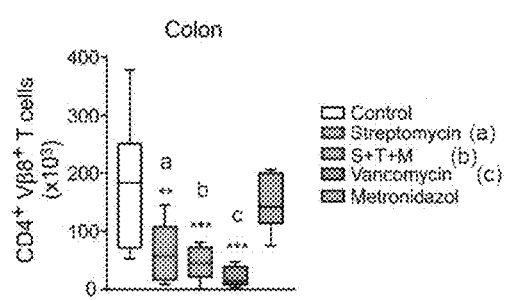
Figure 8F:
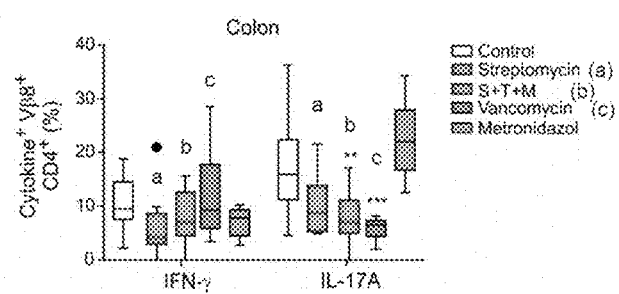

Since the microbiome can be manipulated through the utilization of antibiotics, we assessed whether reduction of *Bacteroides* communities by broad-spectrum antibiotics combination (Sulfadoxine, Trimethoprim and Metronidazol; S+T+M) affects disease progression in TCRM mice. We found that antibiotics treatment resulted in a substantial shift in the microbiome composition including the reduced abundance of *Bacteroides* (FIG. 8A). None of the treated TCRM mice succumbed to lethal inflammatory cardiomyopathy (FIG. 3A), which was most likely due to significantly reduced cardiac inflammation under antibiotic treatment (FIGS. 3B and C). To corroborate these findings and to dissect the activation patterns of cardiac myosin-specific T cells, we utilized the adoptive transfer model of TCRM splenocytes into Rag1−/− mice with antibiotics treatment starting one week before the splenocyte transfer (FIG. 3D). As expected, treatment with broad-spectrum antibiotics such as Vancomycin reduced not only *B. theta* levels in fecal samples (FIG. 3E), but significantly ameliorated the cardiac disease at day 28 post adoptive transfer (FIG. 3F). Flow cytometric analysis confirmed the profound reduction of the cardiac inflammation (FIG. 3G) with significantly reduced accumulation of TCR-transgenic CD4+ T cells in hearts of Rag1−/− recipients treated with Streptomycin, S+T+M or Vancomycin (FIG. 3H). Likewise, these three antibiotic regimens reduced CD45+ immune cell (FIG. 8B) and Vβ8+ CD4+ T cell accumulation in the colon (FIG. 8C), but not in the spleen of Rag1−/− recipients (FIG. 8D). Vancomycin and S+T+M antibiotics treatment had a pronounced impact on the activation of heart-infiltrating and colonic Th17 cells, while the activity of Th1 cells was reduced to a lesser extent (FIG. 3I and FIG. 8E-F). The adoptively transferred B cells from TCRM spleens generated *B. theta*-specific IgG antibodies that could be detected in the serum of Rag1$^{-/-}$ recipients on day 28 post transfer (FIG. 3J). Antibiotics treatment reduced *B. theta*-specific IgG antibodies, but had variable effects on IgG antibody responses against *B. distasonis, B. vulgatus* or *Enterobacter cloacae* (FIG. 3J) indicating that antibiotics treatment did not negatively impact global immune reactivity in the Rag1$^{-/-}$ recipients. These results and the finding that adoptive transfer of heart-specific TCRM cells to BALB/c mice significantly enhanced anti-*B. theta* antibody responses (FIG. 3K) further support the notion that heart-specific CD4$^+$ T cells specifically interact with microbial components in the intestine and thereby impact systemic immune reactivity.

T and B Cell Reactivity Against *Bacteroides* in Human Myocarditis Patients

Figure 4A:
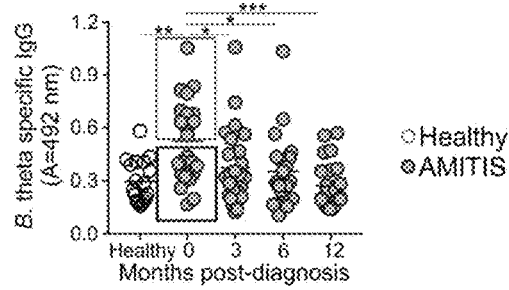
FIGS. 4A-M. Immune reactivity against *Bacteroides* and cardiac myosin antigens in human myocarditis patients.
Figure 4B:
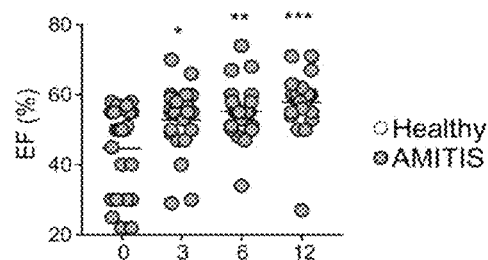
Figure 4C:
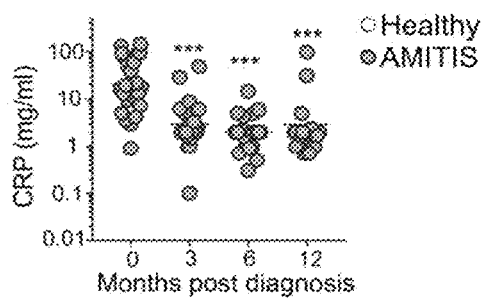
Figure 4D:
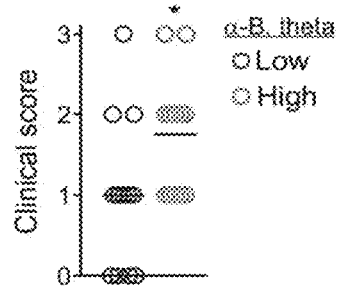

To establish translational relevance of the link between microbial molecular mimicry and inflammatory cardiomyopathy, we assessed anti-*Bacteroides* IgG responses in sera from patients with endomyocardial biopsy-proven myocarditis (Etics/AMITIS study, Table 2) (27). Patients with acute myocarditis showed significantly elevated *B. theta*-specific IgG responses compared to a healthy control group (FIG. 4A). Clinical improvement of the myocarditis patients with gain of heart function (FIG. 4B) and reduced inflammatory status (FIG. 4C) was accompanied by a reduction in seroreactivity against *B. theta* (FIG. 4A). Based on anti-*B. theta* IgG reactivity in patients with acute myocarditis, we grouped the patients into high (>mean, red box in FIG. 4A) and low (<mean, black box in FIG. 4A) responders and correlated their antibody status with the available clinical parameters: positivity for anti-beta 1 adrenergic receptor autoantibodies (FIG. 9A), C-reactive protein (CRP) levels (FIG. 9B) and an ejection fraction cut-off of 40% (FIG. 9C). Acute myocarditis patients with low anti-*B. theta* reactivity showed a combined clinical score that was significantly lower compared to the high responder group (FIG. 4D) indicating that systemic anti-*Bacteroides* immune reactivity is linked to myocardial inflammation in humans.

Figure 4E:
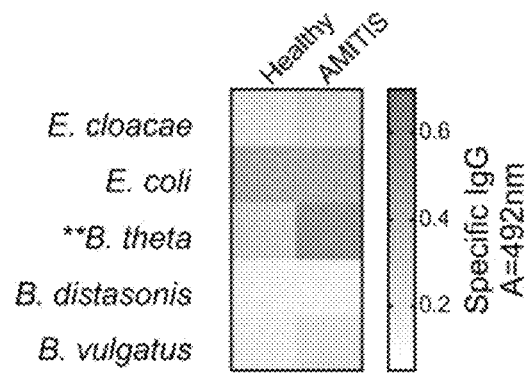
Figure 4F:
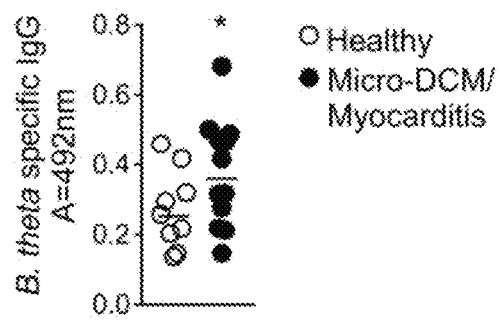
Figure 4G:
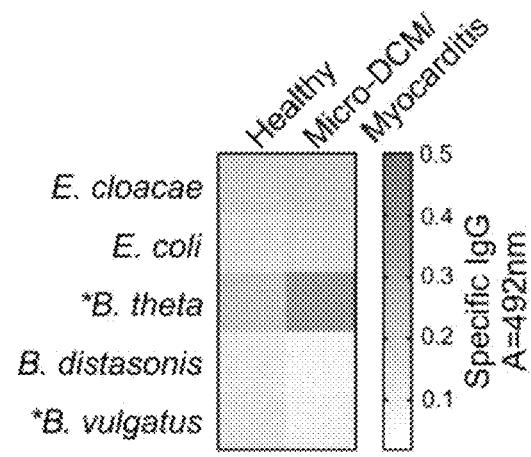

While IgG antibodies against *B. theta* in the AMITIS cohort were diminished at subsequent visits (FIG. 4A), anti-*Enterobacter cloacae* (FIG. 9D), anti-*Escherichia coli* antibodies (FIG. 9E) and total serum IgG concentrations (FIG. 9F) did not change significantly. Moreover, IgG antibody reactivity against other *Bacteroides* species (*B. distasonis* and *B. vulgatus*) was not different in AMITIS myocarditis patients and healthy controls (FIG. 4E). To corroborate these results, we established a prospective clinical study and included thirteen acute myocarditis patients showing typical late enhancement pattern in cardiac magnetic resonance imaging and four acute heart failure patients with left ventricular ejection fraction 540% (Micro-DCM study; Table 3). A cohort of age-matched healthy volunteers served as controls (Table 4). Importantly, myocarditis patients of the Micro-DCM study showed significantly elevated anti-*B. theta* IgG antibodies (FIG. 4F), while seroreactivity against other bacteria—except reduced reactivity against *B. vulgatus*—were not different when compared to healthy controls (FIG. 4G).

Figure 4H:
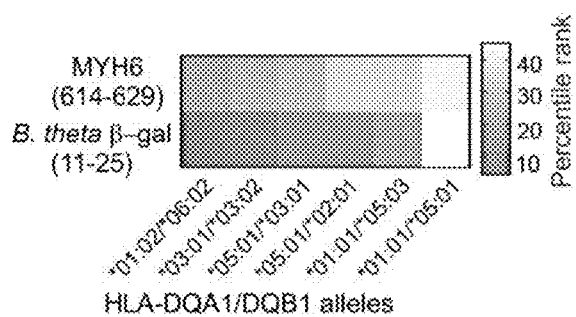
Figure 4K:
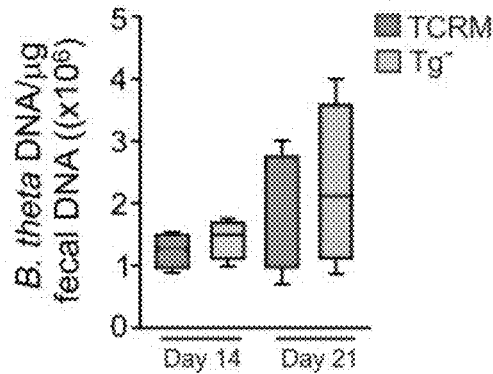
Figure 4I:
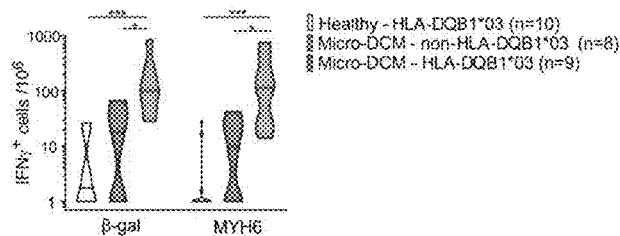
Figure 4L:
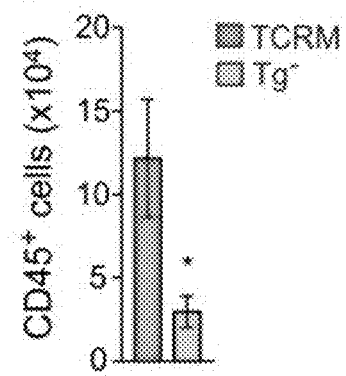
Figure 4J:
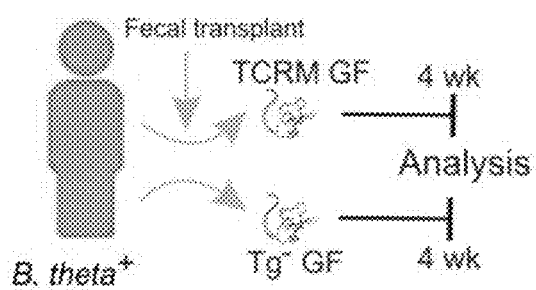
Figure 4M:
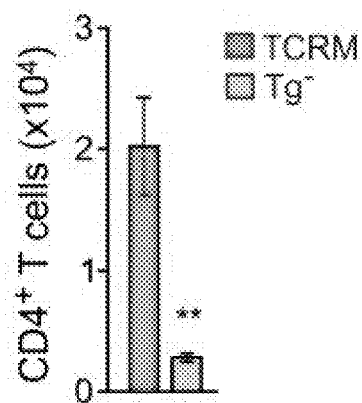

Preclinical studies in mice have established that MYH6 is the dominant autoantigen in the heart tissue (5, 28) and that susceptibility to experimental autoimmune myocarditis depends mainly on the MHC haplotype, whereby MYH6 epitopes appear to be presented by different MHC class II molecules (29). Bioinformatics analysis of binding affinities of the *B. theta* β-gal$_{11-25}$ peptide mimic indicated several HLA-DQA1*/HLA-DQB1* combinations, including HLA-DQ8, that are also predicted to bind human MYH6$_{614-629}$ (FIG. 4H). Assessment of T cell reactivity against the MYH6 and β-gal peptides in peripheral blood mononuclear cells Micro-DCM patients revealed that patients exhibit significantly higher IFN-γ reactivity against both peptides when compared to healthy controls (FIG. 4I). Moreover, the frequency of IFN-γ-producing T cells in Micro-DCM patients that possess alleles other than HLA-DQB1*03 was also reduced in comparison to the HLA-DQB1*03-positive group (FIG. 4I). When we focused the analysis on Micro-DCM myocarditis patients and individuals showing a T cell response >0 in the ELISpot assay for at least one of the peptides, we found a highly significant correlation between MYH6 and β-gal$_{11-25}$ peptide reactivity (FIG. 9K) suggesting that heart-specific CD4$^+$ T cells cross-react with the bacterial peptide in human myocarditis patients. Finally, to provide evidence that the presence of *B. theta* in the human intestinal microbiome is causally linked to myocarditis development, we performed fecal transplants from *B. theta*-positive myocarditis patients into GF TCRM and transgene-negative mice (FIG. 4J). Both groups of mice were equally well colonized by *B. theta* (FIG. 4K). Increased accumulation of CD45$^+$ immune cells (FIG. 4L) and CD4$^+$ T cells (FIG. 4M) in TCRM hearts after four weeks of re-colonization indicates that the microbiome of human myocarditis patients contains the pathological principle that drives myocardial inflammation in TCRM mice. In sum, the causal evidence provided by the preclinical studies in TCRM mice and the significant correlation of systemic anti-*Bacteroides* immune reactivity with disease severity in human myocarditis patients indicate that inflammatory cardiomyopathy in humans is driven—at least partially—through the activation of heart-specific Th cells by bacterial peptide mimics that are derived from the intestinal microbiota.

REFERENCES

1. J. Buggey, C. A. ElAmm, Myocarditis and cardiomyopathy. *Curr Opin Cardiol* 33, 341-346 (2018).
2. R. G. Weintraub, C. Semsarian, P. Macdonald, Dilated cardiomyopathy. *Lancet* 390, 400-414 (2017).
3. N. R. Rose, Learning from myocarditis: mimicry, chaos and black holes. *F1000Prime Rep* 6, 25 (2014).
4. B. H. Trachtenberg, J. M. Hare, Inflammatory Cardiomyopathic Syndromes. *Circ Res* 121, 803-818 (2017).
5. P. Krebs et al., Molecular mapping of autoimmune B cell responses in experimental myocarditis. *J. Autoimmun* 28, 224-233 (2007).
6. M. Rangachari et al., T-bet negatively regulates autoimmune myocarditis by suppressing local production of interleukin 17. *J. Exp. Med* 203, 2009-2019 (2006).
7. H. Lv et al., Impaired thymic tolerance to alpha-myosin directs autoimmunity to the heart in mice and humans. *J. Clin. Invest* 121, 1561-1573 (2011).
8. V. Nindl et al., Cooperation of Th1 and Th17 cells determines transition from autoimmune myocarditis to dilated cardiomyopathy. *Eur J Immunol* 42, 2311-2321 (2012).
9. J. M. Myers et al., Cardiac myosin-Th17 responses promote heart failure in human myocarditis. *JCI Insight* 1, (2016).

10. B. Maisch, P. Alter, Treatment options in myocarditis and inflammatory cardiomyopathy: Focus on i.v. immunoglobulins. *Herz*, (2018).
11. S. Heymans, U. Eriksson, J. Lehtonen, L. T. Cooper, Jr., The Quest for New Approaches in Myocarditis and Inflammatory Cardiomyopathy. *J Am Coll Cardiol* 68, 2348-2364 (2016).
12. E. Generali, A. Ceribelli, M. A. Stazi, C. Selmi, Lessons learned from twins in autoimmune and chronic inflammatory diseases. *J Autoimmun* 83, 51-61 (2017).
13. A. Davidson, B. Diamond, Autoimmune diseases. *N Engl J Med* 345, 340-350 (2001).
14. W. Liu, W. M. Li, N. L. Sun, HLA-DQA1, -DQB1 polymorphism and genetic susceptibility to idiopathic dilated cardiomyopathy in Hans of northern China. *Ann Hum Genet* 69, 382-388 (2005).
15. I. Portig, A. Sandmoeller, S. Kreilinger, B. Maisch, HLA-DQB1* polymorphism and associations with dilated cardiomyopathy, inflammatory dilated cardiomyopathy and myocarditis. *Autoimmunity* 42, 33-40 (2009).
16. J. A. Taylor et al., A spontaneous model for autoimmune myocarditis using the human MHC molecule HLA-DQ8. *J. Immunol* 172, 2651-2658 (2004).
17. C. L. Vanderlugt, S. D. Miller, Epitope spreading in immune-mediated diseases: implications for immunotherapy. *Nat. Rev. Immunol* 2, 85-95 (2002).
18. M. B. Oldstone, Molecular mimicry and autoimmune disease. *Cell* 50, 819-820 (1987).
19. F. Teng et al., Gut Microbiota Drive Autoimmune Arthritis by Promoting Differentiation and Migration of Peyer's Patch T Follicular Helper Cells. *Immunity* 44, 875-888 (2016).
20. R. Horai et al., Microbiota-Dependent Activation of an Autoreactive T Cell Receptor Provokes Autoimmunity in an Immunologically Privileged Site. *Immunity* 43, 343-353 (2015).
21. Y. K. Lee, J. S. Menezes, Y. Umesaki, S. K. Mazmanian, Proinflammatory T-cell responses to gut microbiota promote experimental autoimmune encephalomyelitis. *Proc Natl Acad Sci USA* 108 Suppl 1, 4615-4622 (2011).
22. Y. E. Chen, M. A. Fischbach, Y. Belkaid, Skin microbiota-host interactions. *Nature* 553, 427-436 (2018).
23. N. Tai et al., Microbial antigen mimics activate diabetogenic CD8 T cells in NOD mice. *J Exp Med* 213, 2129-2146 (2016).
24. T. Vatanen et al., Variation in Microbiome LPS Immunogenicity Contributes to Autoimmunity in Humans. *Cell* 165, 842-853 (2016).
25. R. Hebbandi Nanjundappa et al., A Gut Microbial Mimic that Hijacks Diabetogenic Autoreactivity to Suppress Colitis. *Cell* 171, 655-667 e617 (2017).
26. K. Honda, D. R. Littman, The microbiota in adaptive immune homeostasis and disease. *Nature* 535, 75-84 (2016).
27. N. Deubner et al., Cardiac beta1-adrenoceptor autoantibodies in human heart disease: rationale and design of the Etiology, Titre-Course, and Survival (ETiCS) Study. *Eur J Heart Fail* 12, 753-762 (2010).
28. C. L. Pummerer et al., Identification of cardiac myosin peptides capable of inducing autoimmune myocarditis in BALB/c mice. *J. Clin. Invest* 97, 2057-2062 (1996).
29. J. G. Barin, D. Cihakova, Control of inflammatory heart disease by CD4+ T cells. *Ann N Y Acad Sci* 1285, 80-96 (2013).
30. L. Zhang et al., Cardiotoxicity of Immune Checkpoint Inhibitors. *Curr Treat Options Cardiovasc Med* 21, 32 (2019).
31. D. B. Johnson et al., Fulminant Myocarditis with Combination Immune Checkpoint Blockade. *N Engl J Med* 375, 1749-1755 (2016).
32. A. Cossarizza et al., Guidelines for the use of flow cytometry and cell sorting in immunological studies. *Eur J Immunol* 47, 1584-1797 (2017).
33. N. M. Koropatkin, E. C. Martens, J. I. Gordon, T. J. Smith, Starch catabolism by a prominent human gut symbiont is directed by the recognition of amylose helices. *Structure* 16, 1105-1115 (2008).
34. M. Mamantopoulos et al., Nlrp6- and ASC-Dependent Inflammasomes Do Not Shape the Commensal Gut Microbiota Composition. *Immunity* 47, 339-348 e334 (2017).
35. T. Miki, R. Goto, M. Fujimoto, N. Okada, W. D. Hardt, The Bactericidal Lectin RegIIIbeta Prolongs Gut Colonization and Enteropathy in the Streptomycin Mouse Model for *Salmonella* Diarrhea. *Cell Host Microbe* 21, 195-207 (2017).
36. J. J. Bunker et al., Innate and Adaptive Humoral Responses Coat Distinct Commensal Bacteria with Immunoglobulin A. *Immunity* 43, 541-553 (2015).
37. C. Gil-Cruz et al., Fibroblastic reticular cells regulate intestinal inflammation via IL-15-mediated control of group 1 ILCs. *Nat Immunol* 17, 1388-1396 (2016).
38. J. G. Caporaso et al., QIIME allows analysis of high-throughput community sequencing data. *Nat Methods* 7, 335-336 (2010).
39. C. A. Hickey et al., Colitogenic *Bacteroides* thetaiotaomicron Antigens Access Host Immune Cells in a Sulfatase-Dependent Manner via Outer Membrane Vesicles. *Cell Host Microbe* 17, 672-680 (2015).
40. J. Greenbaum et al., Functional classification of class II human leukocyte antigen (HLA) molecules reveals seven different supertypes and a surprising degree of repertoire sharing across supertypes. *Immunogenetics* 63, 325-335 (2011).
41. V. Gopalakrishnan et al., Gut microbiome modulates response to anti-PD-1 immunotherapy in melanoma patients. *Science* 359, 97-103 (2018).

We claim:

1. A method of limiting progression of myocarditis toward dilated cardiomyopathy (DCM) in a subject in need thereof, comprising reducing the amount of B. thetaiotaomicron and/or B. faecis in the subject by orally or enterally administering to the subject an effective amount of a recombinant phage or packaged phagemid that targets the B. thetaiotaomicron and/or B. faecis and encodes a Clustered Regularly Interspaced Short Palindromic Repeats (CRISPR)-Cas nuclease and a guide RNA that are designed to specifically cleave the genome of the B. thetaiotaomicron and/or B. faecis to reduce the amount of the B. thetaiotaomicron and/or B. faecis in the intestine of the subject.

2. The method of claim 1, wherein the CRISPR-Cas nuclease is Cas9.

3. The method of claim 1, wherein the CRISPR-Cas nuclease is Cpf1 (Cas12a).

4. The method of claim 1, wherein the CRISPR-Cas nuclease is Cas 3.

5. The method of claim 1, wherein the recombinant phage or packaged phagemid is enterally administered to the subject.

6. The method of claim 1, wherein the recombinant phage or packaged phagemid is orally administered to the subject.

7. The method of claim 1, wherein the recombinant phage or packaged phagemid targets the B. thetaiotaomicron.

* * * * *

SEQUENCE LISTING

<160> NUMBER OF SEQ ID NOS: 23

<210> SEQ ID NO 1
<211> LENGTH: 1022
<212> TYPE: PRT
<213> ORGANISM: Bacteroides thetaiotaomicron

<400> SEQUENCE: 1

-continued

```
Met Lys Leu Lys Lys Arg Thr Phe Leu Ile Leu Met Ala Ala Leu Thr
1               5                   10                  15

Ala Thr Phe Ala Ser Ala Gln Lys Gln Pro Leu Pro Glu Trp Gln Ser
            20                  25                  30

Gln Tyr Ala Val Gly Leu Asn Lys Leu Ala Pro His Thr Tyr Val Trp
        35                  40                  45

Pro Tyr Ala Asp Ala Ser Asp Ile Gly Lys Pro Gly Gly Tyr Glu Gln
    50                  55                  60

Ser Pro Tyr Tyr Met Ser Leu Asn Gly Lys Trp Lys Phe Asn Trp Val
65                  70                  75                  80

Lys Asn Pro Asp Asn Arg Pro Lys Asp Phe Tyr Gln Pro Ser Tyr Tyr
                85                  90                  95

Thr Gly Gly Trp Ala Asp Ile Asn Val Pro Gly Asn Trp Glu Arg Gln
            100                 105                 110

Gly Tyr Gly Thr Ala Ile Tyr Val Asn Glu Thr Tyr Glu Phe Asp Asp
        115                 120                 125

Lys Met Phe Asn Phe Lys Lys Asn Pro Pro Leu Val Pro Phe Ala Glu
    130                 135                 140

Asn Glu Val Gly Ser Tyr Arg Arg Thr Phe Lys Val Pro Ala Asp Trp
145                 150                 155                 160

Lys Gly Arg Arg Val Val Leu Cys Cys Glu Gly Val Ile Ser Phe Tyr
                165                 170                 175

Tyr Val Trp Val Asn Gly Lys Leu Leu Gly Tyr Asn Gln Gly Ser Lys
            180                 185                 190

Thr Ala Ala Glu Trp Asp Ile Thr Asp Val Leu Ser Glu Gly Glu Asn
        195                 200                 205

Val Val Ala Leu Glu Val Tyr Arg Trp Ser Ser Gly Ala Tyr Leu Glu
    210                 215                 220

Cys Gln Asp Met Trp Arg Leu Ser Gly Ile Glu Arg Asp Val Tyr Leu
225                 230                 235                 240

Tyr Ser Thr Pro Lys Gln Tyr Ile Ala Asp Tyr Lys Val Ser Ala Ser
                245                 250                 255

Leu Asp Lys Glu Lys Tyr Lys Glu Gly Ile Phe Asn Leu Glu Val Thr
            260                 265                 270

Val Glu Gly Pro Ser Ala Thr Ala Ser Ser Ile Ala Tyr Thr Leu Lys
        275                 280                 285

Asp Ala Ser Gly Lys Ala Val Leu Gln Asp Ala Ile Asn Ile Lys Ser
    290                 295                 300

Arg Gly Leu Ser Asn Phe Ile Ala Phe Asp Glu Lys Lys Ile Ala Glu
305                 310                 315                 320

Val Lys Ala Trp Asn Ala Glu His Pro Asn Leu Tyr Thr Leu Val Leu
                325                 330                 335

Glu Leu Lys Asp Ala Gln Gly Lys Val Thr Glu Leu Thr Gly Cys Glu
            340                 345                 350

Val Gly Phe Arg Thr Ser Glu Ile Lys Asp Gly Arg Phe Cys Ile Asn
        355                 360                 365

Gly Val Pro Val Leu Val Lys Gly Thr Asn Arg His Glu His Ser Gln
    370                 375                 380

Leu Gly Arg Thr Val Ser Lys Glu Leu Met Glu Gln Asp Ile Arg Leu
385                 390                 395                 400

Met Lys Gln His Asn Ile Asn Met Val Arg Asn Ser His Tyr Pro Thr
                405                 410                 415
```

```
His Pro Tyr Trp Tyr Gln Leu Cys Asp Arg Tyr Gly Leu Tyr Met Ile
            420                 425                 430

Asp Glu Ala Asn Ile Glu Ser His Gly Met Gly Tyr Gly Pro Ala Ser
        435                 440                 445

Leu Ala Lys Asp Ser Thr Trp Leu Thr Ala His Met Asp Arg Thr His
    450                 455                 460

Arg Met Tyr Glu Arg Ser Lys Asn His Pro Ala Ile Val Ile Trp Ser
465                 470                 475                 480

Gln Gly Asn Glu Ala Gly Asn Gly Ile Asn Phe Glu Arg Thr Tyr Asp
                485                 490                 495

Trp Leu Lys Ser Val Glu Lys Gly Arg Pro Val Gln Tyr Glu Arg Ala
            500                 505                 510

Glu Leu Asn Tyr Asn Thr Asp Ile Tyr Cys Arg Met Tyr Arg Ser Val
        515                 520                 525

Asp Glu Ile Lys Ala Tyr Val Gly Lys Lys Asp Ile Tyr Arg Pro Phe
    530                 535                 540

Ile Leu Cys Glu Tyr Leu His Ala Met Gly Asn Ser Cys Gly Gly Met
545                 550                 555                 560

Lys Glu Tyr Trp Glu Val Phe Glu Asn Glu Pro Met Ala Gln Gly Gly
                565                 570                 575

Cys Ile Trp Asp Trp Val Asp Gln Asn Phe Arg Glu Ile Asp Lys Asp
            580                 585                 590

Gly Lys Trp Tyr Trp Thr Tyr Gly Gly Asp Tyr Gly Pro Glu Gly Ile
        595                 600                 605

Pro Ser Phe Gly Asn Phe Cys Gly Asn Gly Leu Val Asn Ala Val Arg
610                 615                 620

Glu Pro His Pro His Leu Leu Glu Val Lys Lys Ile Tyr Gln Asn Ile
625                 630                 635                 640

Lys Ala Thr Leu Ser Asp Arg Lys Asn Leu Lys Val Cys Ile Lys Asn
                645                 650                 655

Trp Tyr Asp Phe Ser Asn Leu Asn Glu Tyr Ile Leu Arg Trp Asn Val
            660                 665                 670

Lys Gly Glu Asp Gly Thr Val Leu Ala Glu Gly Thr Lys Glu Val Asp
        675                 680                 685

Cys Glu Pro His Ala Thr Val Asp Val Thr Leu Gly Ala Val Lys Leu
690                 695                 700

Pro Asn Thr Val Arg Glu Ala Tyr Leu Asn Leu Ser Trp Ser Arg Lys
705                 710                 715                 720

Glu Ala Thr Pro Leu Val Asp Thr Asp Trp Glu Val Ala Tyr Asp Gln
                725                 730                 735

Phe Val Leu Ala Gly Asn Lys Asn Thr Thr Ala Tyr Arg Pro Gln Lys
            740                 745                 750

Ala Gly Glu Thr Ala Phe Val Val Asp Lys Asn Thr Gly Ala Leu Ser
        755                 760                 765

Ser Leu Thr Leu Asp Gly Lys Glu Leu Leu Ala Pro Ile Thr Leu
    770                 775                 780

Ser Leu Phe Arg Pro Ala Thr Asp Asn Asp Asn Arg Asp Arg Asn Gly
785                 790                 795                 800

Ala Arg Leu Trp Arg Lys Ala Gly Leu Asn Asn Leu Thr Gln Lys Val
                805                 810                 815

Val Ser Leu Lys Glu Lys Thr Ser Ala Thr Val Arg Ala Glu Ile
            820                 825                 830

Leu Asn Gly Lys Gly Gln Lys Val Gly Met Ala Asp Phe Val Tyr Ala
```

```
                    835                    840                    845
Leu Asp Lys Asn Gly Ala Leu Lys Val Arg Thr Thr Phe Gln Pro Asp
    850                    855                    860

Thr Ala Ile Val Lys Ser Met Ala Arg Leu Gly Leu Thr Phe Arg Met
865                    870                    875                    880

Ala Asp Ala Tyr Asn Gln Val Ser Tyr Leu Gly Arg Gly Asp His Glu
                    885                    890                    895

Thr Tyr Ile Asp Arg Asn Gln Ser Gly Arg Ile Gly Leu Tyr Asp Thr
                900                    905                    910

Thr Val Glu Arg Met Phe His Tyr Tyr Ala Thr Pro Gln Ser Thr Ala
                915                    920                    925

Asn Arg Thr Asp Val Arg Trp Ala Lys Leu Thr Asp Gln Ala Gly Glu
            930                    935                    940

Gly Val Phe Met Glu Ser Asn Arg Pro Phe Gln Phe Ser Ile Ile Pro
945                    950                    955                    960

Phe Ser Asp Val Leu Leu Glu Lys Ala His His Ile Asn Glu Leu Glu
                965                    970                    975

Arg Asp Gly Met Ile Thr Ile His Leu Asp Ala Glu Gln Ala Gly Val
            980                    985                    990

Gly Thr Ala Thr Cys Gly Pro Gly  Val Leu Pro Gln Tyr  Leu Val Pro
            995                    1000                   1005

Val Lys  Lys Gln Ser Phe Glu  Phe Thr Leu Tyr Pro  Val Lys
   1010                    1015                    1020

<210> SEQ ID NO 2
<211> LENGTH: 3069
<212> TYPE: DNA
<213> ORGANISM: Bacteroides thetaiotaomicron

<400> SEQUENCE: 2
atgaaattaa agaaacgaac gttttaatc ttgatggcag cactgactgc taccttcgct      60
tcggctcaga acagcctttt gccggagtgg cagagccagt atgcggtagg actgaataaa    120
ctcgctcctc ataccttatgt atggccttac gccgacgctt ccgatattgg aaagccggga   180
ggatatgaac agtctcctta ttatatgagt ctgaacggga agtggaaatt taactgggtg    240
aagaacccgg acaaccgtcc gaaggacttt taccagccct cttattatac cggagggtgg    300
gcggatatta atgttcccgg caactgggaa cggcaaggct acggaacagc tatctatgtc    360
aacgaaactt atgagtttga cgacaagatg ttcaacttca gaagaatccc gccattggtt    420
ccatttgctg agaatgaagt aggttcttat cgtcgcacgt ttaaggtgcc tgccgactgg    480
aaaggacgtc gggtagtgct ctgctgcgaa ggagtgatct ctttctatta tgtatgggtg    540
aacggaaagt tgcttggcta atcagggga tcgaagacgg ctgccgaatg ggacattacc     600
gatgtactga gtgaaggaga gaatgtggta gctctggaag tatatcgctg gagttcgggt    660
gcttatctgg aatgtcagga tatgtggcgt ctgagtggca tcgaacggga tgtttatctg    720
tatagcactc ccaaacagta tattgctgac ataaagtaa gtgcttccct tgataaagag     780
aaatacaaag aaggtatctt caatctggaa gtgacggtgg aaggcccttc tgctactgcc    840
agctctatcg cttatacact gaaggatgct tccggaaagg cagtattgca ggatgccatt    900
aacatcaagt cccgtggact gagtaacttt atcgctttcg atgagaagaa gattgcagaa    960
gtaaaagcat ggaatgcgga gcatcctaac ctttataccct tggtactcga attaaaagat  1020
gcgcaaggaa aagtaaccga actgaccggt tgtgaagtcg gtttccgtac ttcggaaatc  1080
```

-continued

```
aaggacggac gtttctgtat taacggtgtt ccggtgctgg tgaaagggac gaaccgtcac    1140
gaacattcgc aactgggacg taccgtaagc aaagaactga tggaacagga tatccgcctg    1200
atgaaacagc ataatatcaa catggtgcgt aactcacatt atccgactca tccgtactgg    1260
tatcagcttt gcgaccgcta cgggctgtat atgattgatg aggcgaatat cgaatcgcat    1320
ggcatgggat acgggcctgc ctcccttgcc aaagacagta cttggctgac cgctcacatg    1380
gaccgtacac accgtatgta cgaacgttcc aagaatcatc cggctatcgt gatctggtca    1440
cagggcaatg aagccggcaa cggcatcaac ttcgaacgta cttacgactg gctgaaatcg    1500
gtagagaaag gccgtcccgt gcaatatgaa cgtgctgaac tgaattacaa cacggacatc    1560
tattgccgta tgtaccgcag tgtggacgaa attaaggcat acgtgggtaa gaaggatatt    1620
taccgtcctt tcattctttg cgaatatctg cacgctatgg gtaacagttg cggtggaatg    1680
aaagaatact gggaagtctt tgaaaatgag ccgatggcac aaggggggctg catttgggac    1740 tgggtggatc agaacttccg tgaaatagac aaagacggaa aatggtactg gacttatgga    1800
ggcgattacg gaccggaagg aatccccagc ttcggtaatt tctgtggcaa cggtctggtg    1860
aatgctgttc gtgaaccgca tccgcatcta ctcgaagtga agaaaatata tcagaacatc    1920
aaagcgactt tgtcagaccg gaagaatctg aaagtctgca taagaactg gtatgacttt    1980 tctaatctga tgaatatat cctgcgttgg aatgtgaaag gggaggatgg aaccgtactt    2040
gccgaaggca cgaaggaagt agactgcgag ccgcacgcta cggtagatgt cactttgggt    2100
gccgtcaaac ttccgaatac cgttcgggaa gcctatctga acctaagctg gagccgtaaa    2160
gaggccactc cgctagtgga taccgactgg gaagtggcat acgaccagtt tgtacttgcc    2220
ggtaataaga atacgacggc ttatcgtccg cagaaggcgg gagaaacagc ttttgttgtg    2280
gacaagaata ccggggcact tcttcccctg actttggatg gaaaggaatt gctggctgca    2340
ccaatcactt tgagcctgtt ccgtccggct acggataatg ataaccggga taggaacgga    2400
gcccgtctgt ggcgcaaggc aggtttgaac aatctgacac agaaagtggt gtcactgaaa    2460
gaagaaaaga catcggcaac ggtccgtgct gagattctta atgggaaagg acagaaagta    2520
ggaatggcgg attttgttta tgcactcgac aagaacgggg cattgaaggt tcgcaccacc    2580
ttccagccgg atacggcgat tgtgaagtcg atggctcgtc tggggctgac cttccgcatg    2640
gcagatgctt ataatcaagt atcttatctg gacgtggcg atcatgaaac gtatatcgac    2700
cgcaaccagt ccggtaggat aggactgtat gatacgacgg tagaacggat gttccactat    2760
tacgctaccc cacaatctac agctaaccgg acagatgtac gctgggcgaa actgacggat    2820
caggcaggcg aaggtgtctt tatggaatcg aatcgtcctt tccagtttag tatcattcct    2880
ttctcggatg tattattaga gaaggcgcac cacattaatg aactggagcg tgacggaatg    2940
ataactatac atctggatgc cgaacaggca ggagtaggta cggctacctg cggaccgggt    3000
gtattgccgc aatatctggt accggtgaaa aagcagagtt ttgaatttac gctttatccg    3060
gtaaaatag                                                           3069
```

<210> SEQ ID NO 3
<211> LENGTH: 45
<212> TYPE: DNA
<213> ORGANISM: Artificial Sequence
<220> FEATURE:
<223> OTHER INFORMATION: Bt_bgal_ko_1 primer

<400> SEQUENCE: 3
aagataacat tcgagtcgac tatttcggca ataatacgct gaaag    45

<210> SEQ ID NO 4
<211> LENGTH: 49
<212> TYPE: DNA
<213> ORGANISM: Artificial Sequence
<220> FEATURE:
<223> OTHER INFORMATION: Bt_bgal_ko_2 primer

<400> SEQUENCE: 4
caaatgcaat cagtttcagg cattattata ttgttttttg gtgactggt                49

<210> SEQ ID NO 5
<211> LENGTH: 21
<212> TYPE: DNA
<213> ORGANISM: Artificial Sequence
<220> FEATURE:
<223> OTHER INFORMATION: Bt_bgal_ko_3 primer

<400> SEQUENCE: 5
cctgaaactg attgcatttg g                                              21

<210> SEQ ID NO 6
<211> LENGTH: 41
<212> TYPE: DNA
<213> ORGANISM: Artificial Sequence
<220> FEATURE:
<223> OTHER INFORMATION: Bt_bgal_ko_4 primer

<400> SEQUENCE: 6
gcggtggcgg ccgctctaga agtcgtttgt tgttttcttc g                        41

<210> SEQ ID NO 7
<211> LENGTH: 22
<212> TYPE: DNA
<213> ORGANISM: Artificial Sequence
<220> FEATURE:
<223> OTHER INFORMATION: 1626_250us_f primer

<400> SEQUENCE: 7
cacatagtag ttttctttcg tc                                             22

<210> SEQ ID NO 8
<211> LENGTH: 18
<212> TYPE: DNA
<213> ORGANISM: Artificial Sequence
<220> FEATURE:
<223> OTHER INFORMATION: 1626_264inside_r primer

<400> SEQUENCE: 8
gcgaaactga cggatcag                                                  18

<210> SEQ ID NO 9
<211> LENGTH: 19
<212> TYPE: DNA
<213> ORGANISM: Artificial Sequence
<220> FEATURE:
<223> OTHER INFORMATION: 1626_250ds_r primer

<400> SEQUENCE: 9
tcggacgata atgcgactt                                                 19

<210> SEQ ID NO 10
<211> LENGTH: 18
<212> TYPE: PRT
<213> ORGANISM: Artificial Sequence
<220> FEATURE:

<223> OTHER INFORMATION: MYH6 614-629

<400> SEQUENCE: 10

Arg Ser Leu Lys Leu Met Ala Thr Leu Phe Ser Thr Tyr Ala Ser Ala
1               5                   10                  15

Asp Arg

<210> SEQ ID NO 11
<211> LENGTH: 18
<212> TYPE: PRT
<213> ORGANISM: Artificial Sequence
<220> FEATURE:
<223> OTHER INFORMATION: Bacteroides -galactosidase 11-25

<400> SEQUENCE: 11

Thr Phe Leu Ile Leu Met Ala Ala Leu Thr Ala Thr Phe Ala Ser Ala
1               5                   10                  15

Gln Lys

<210> SEQ ID NO 12
<211> LENGTH: 18
<212> TYPE: PRT
<213> ORGANISM: Artificial Sequence
<220> FEATURE:
<223> OTHER INFORMATION: Enterobacter cysteine hydrolase 10-27

<400> SEQUENCE: 12

Leu Leu Ile Gly Met Met Ser Thr Phe Ser Thr Tyr Ala Ser Ala Gln
1               5                   10                  15

Glu Thr

<210> SEQ ID NO 13
<211> LENGTH: 17
<212> TYPE: PRT
<213> ORGANISM: Artificial Sequence
<220> FEATURE:
<223> OTHER INFORMATION: OVA 323-339

<400> SEQUENCE: 13

Ile Ser Gln Ala Val His Ala Ala His Ala Glu Ile Asn Glu Ala Gly
1               5                   10                  15

Arg

<210> SEQ ID NO 14
<211> LENGTH: 30
<212> TYPE: DNA
<213> ORGANISM: Artificial Sequence
<220> FEATURE:
<223> OTHER INFORMATION: barcoded forward fusion primer

<400> SEQUENCE: 14
ccatctcatc cctgcgtgtc tccgactcag                                    30

<210> SEQ ID NO 15
<211> LENGTH: 43
<212> TYPE: DNA
<213> ORGANISM: Artificial Sequence
<220> FEATURE:
<223> OTHER INFORMATION: reverse fusion primer

<400> SEQUENCE: 15
cctctctatg ggcagtcggt gatacgagct gacgacarcc atg                     43

```
<210> SEQ ID NO 16
<211> LENGTH: 16
<212> TYPE: PRT
<213> ORGANISM: Mus musculus

<400> SEQUENCE: 16

Ser Leu Lys Leu Met Ala Thr Leu Phe Ser Thr Tyr Ala Ser Ala Asp
1               5                   10                  15

<210> SEQ ID NO 17
<211> LENGTH: 16
<212> TYPE: PRT
<213> ORGANISM: Homo sapiens

<400> SEQUENCE: 17

Ser Leu Lys Leu Met Ala Thr Leu Phe Ser Ser Tyr Ala Thr Ala Asp
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: peptide from Bacteroides faecis

<400> SEQUENCE: 18

Phe Leu Ile Leu Met Ala Ala Leu Thr Ala Thr Phe Ala Ser Ala Gln
1               5                   10                  15

<210> SEQ ID NO 19
<211> LENGTH: 16
<212> TYPE: PRT
<213> ORGANISM: Bacteroides thetaiotaomicron

<400> SEQUENCE: 19

Phe Leu Ile Leu Met Ala Ala Leu Thr Ala Thr Phe Ala Ser Ala Gln
1               5                   10                  15

<210> SEQ ID NO 20
<211> LENGTH: 16
<212> TYPE: PRT
<213> ORGANISM: Enterobacter cloacae

<400> SEQUENCE: 20

Leu Ile Gly Met Met Ser Thr Phe Ser Thr Tyr Ala Ser Ala Gln Glu
1               5                   10                  15

<210> SEQ ID NO 21
<211> LENGTH: 16
<212> TYPE: PRT
<213> ORGANISM: Enterococcus faecalis

<400> SEQUENCE: 21

Gly Met Thr Leu Met Gly Leu Ser Thr Leu Phe Leu Ser Thr Tyr Ala
1               5                   10                  15

<210> SEQ ID NO 22
<211> LENGTH: 16
<212> TYPE: PRT
<213> ORGANISM: Chlamydia pneumoniae

<400> SEQUENCE: 22

Leu Glu Thr Ser Met Ala Glu Phe Thr Ser Thr Asn Val Ile Ser Leu
1               5                   10                  15
```

```
<210> SEQ ID NO 23
<211> LENGTH: 20
<212> TYPE: DNA
<213> ORGANISM: Artificial Sequence
<220> FEATURE:
<223> OTHER INFORMATION: barcoded forward fusion primer

<400> SEQUENCE: 23
attagatacc cyggtagtcc                                              20
```